(12) United States Patent
Lang et al.

(10) Patent No.: US 12,144,851 B2
(45) Date of Patent: Nov. 19, 2024

(54) VACCINAL STRATEGY

(71) Applicants: INSERM (INSTITUT NATIONAL DE LA SANTÉ ET DE LA RECHERCHE MÉDICALE), Paris (FR); UNIVERSITÉ DE NANTES, Nantes (FR)

(72) Inventors: François Lang, Nantes (FR); Catherine Rabu, Nantes (FR)

(73) Assignees: INSTITUT NATIONAL DE LA SANTE ET DE LA RECHERCHE MEDICALE (INSERM), Paris (FR); UNIVERSITE DE NANTES, Nantes (FR)

( * ) Notice: Subject to any disclaimer, the term of this patent is extended or adjusted under 35 U.S.C. 154(b) by 754 days.

(21) Appl. No.: 17/046,816

(22) PCT Filed: Apr. 12, 2019

(86) PCT No.: PCT/EP2019/059421
§ 371 (c)(1),
(2) Date: Oct. 12, 2020

(87) PCT Pub. No.: WO2019/197610
PCT Pub. Date: Oct. 17, 2019

(65) Prior Publication Data
US 2021/0154282 A1 May 27, 2021

(30) Foreign Application Priority Data
Apr. 13, 2018 (EP) .................. 18305456

(51) Int. Cl.
*C07K 16/00* (2006.01)
*A61K 39/00* (2006.01)
*A61K 47/65* (2017.01)
*C07K 14/705* (2006.01)
*C07K 14/73* (2006.01)

(52) U.S. Cl.
CPC .......... *A61K 39/0011* (2013.01); *A61K 47/65* (2017.08); *C07K 14/70514* (2013.01); *C07K 14/70517* (2013.01); *A61K 2039/55516* (2013.01); *A61K 2039/876* (2018.08)

(58) Field of Classification Search
CPC ............. A61K 39/0011; A61K 47/65; A61K 2039/55516; A61K 2039/876; C07K 14/70514; C07K 14/70517
See application file for complete search history.

(56) References Cited

U.S. PATENT DOCUMENTS

| 6,464,975 | B2 * | 10/2002 | Millis | A61K 38/1709 |
| | | | | 424/139.1 |
| 9,475,841 | B2 * | 10/2016 | Labarriere | C07K 7/08 |
| 9,573,975 | B2 * | 2/2017 | Labarriere | A61K 39/00119 |
| 9,981,004 | B2 * | 5/2018 | Sigalov | A61P 19/02 |
| 2002/0155106 | A1 * | 10/2002 | Hammond | C07K 7/06 |
| | | | | 435/7.1 |
| 2014/0154291 | A1 * | 6/2014 | Sigalov | A61K 35/00 |
| | | | | 514/19.3 |
| 2016/0137730 | A1 * | 5/2016 | Abrams | C07K 16/28 |
| | | | | 435/69.6 |

FOREIGN PATENT DOCUMENTS

| WO | 2010/026165 A1 | 3/2010 | |
| WO | WO-2016123200 A1 * | 8/2016 | .......... C07K 14/755 |
| WO | WO-2017087827 A1 * | 5/2017 | ....... C07K 14/43518 |

OTHER PUBLICATIONS

Balmana et al. Ann Oncol 2009; 20(supp 4):iv19-20 (Year: 2009).*
Kataja et al., Ann Oncol 2009; 20(sup 4): iv10-14 (Year: 2009).*
Nelson et al., Ann. Intern Med. 2009; 151:727-737 (Year: 2009).*
Engelhard, Current Opinion in Immunology vol. 6 p. 13 (1994) (Year: 1994).*
Guo, et al Nature vol. 360 p. 384 (1992) (Year: 1992).*
Rammensee et al, Immunogenetics vol. 41 p. 178 (1995), (Year: 1995).*
Shastri et al J. Immunol. 1995 vol. 155 p. 4339 (Year: 1995).*

(Continued)

*Primary Examiner* — Sheela J. Huff
(74) *Attorney, Agent, or Firm* — WC&F IP

(57) ABSTRACT

The present invention relates to the prevention and treatment of disease like cancer. The inventors have previously characterized MELOE-1 antigen as an IRES dependent, melanoma specific translation product from a lncRNA mainly transcribed in the melanocytic lineage. MELOE-1 contains numerous class II epitopes and one HLA-A*0201-restricted CD8 epitope eliciting a frequent repertoire of high avidity T cells. They designed various synthetic long peptide (SLPs) comprising a CD4 epitope coupled to the CD8 epitope by a serie of linkers of 4 to 6 aa and studied the efficacy of T cell clone activation by SLP-loaded DC in vitro. Particularly, they evaluated the ability of a few selected SLPs to stimulate specific T cells proliferation of PBL from healthy donors in vitro and finally, they explored the vaccination potential of their best SLP candidate in vivo in an HLA*A0201/HLA-DRB0101 transgenic mouse. Thus, the present invention relates a SLP comprising a CD4 class II peptide linked to a CD8 class I peptide by a specific linker and its use in the treatment of disease like cancers.

Figure 1B:
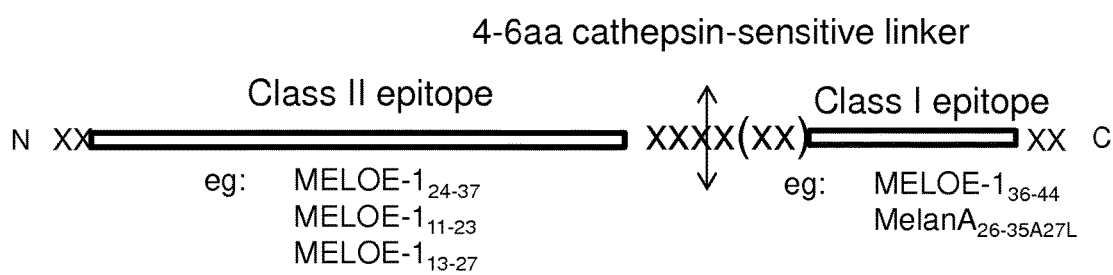

12 Claims, 10 Drawing Sheets
Specification includes a Sequence Listing.

(56) References Cited

OTHER PUBLICATIONS

Kazutaka Masuko et al.: "Artificially synthesized helper/killer-hybrid epitope long peptide (H/K-HELP): Preparation and immunological analysis of vaccine efficacy", Immunology Letters, vol. 163, No. 1, Jan. 1, 2015, pp. 102-112.

Norihiko Takahashi et al.: "First clinical trial of cancer vaccine therapy with artificially synthesized helper/ killer-hybrid epitope long peptide of MAGE-A4 cancer antigen", Cancer Science, vol. 103, No. 1, Jan. 1, 2012, pp. 150-153.

* cited by examiner

A.

```
  2        10        20        30        36      46
SCVGYPDEATSREQFLPSEGAACPPWHPSERISSTLNDECWPASL  (SEQ ID NO:12)
```

HLA restriction 36-44 TLNDECWPA       A*0201        (Godet; JEM 2008)
(SEQ ID NO:31)

24-37 CPPWHPSERISSTL   DRB1*1101    (Rogel, CII 2010)
(SEQ ID NO:26)

13-27 REQFLPSEGAACPPW (SEQ ID NO:21)  DRB1*0101 (unpublished results)

11-23 TSREQFLPSEGAA    DRB1*0101    (Bobinet, PlosO 2012)
(SEQ ID NO:24)

Figure 1A

B.

A.

A.

B.

VACCINAL STRATEGY

SEQUENCE LISTING

This application includes as the Sequence Listing the complete contents of the accompanying text file "Sequence.txt", created Oct. 12, 2020, containing 53 kilobytes, hereby incorporated by reference.

FIELD OF THE INVENTION

The present invention relates to a specific linker and a synthetic long peptide (SLP) comprising a CD4 class II peptide linked to a CD8 class I peptide by the specific linker. Particularly, the invention relates to the use of the SLP in the treatment of cancers, infectious diseases, inflammatory diseases or auto-immune diseases in a patient in need thereof.

BACKGROUND OF THE INVENTION

It is now established that cancer vaccines triggering T cell activation against tumor antigens can be beneficial to cancer patients (1) although many improvements in the vaccination strategies are still necessary to achieve long-term survival of patients. (2). Various immunogens have been tested, ranging from minimal CTL epitope to the full length recombinant protein. Minimal CTL epitope, usually 9-10 amino acids in length led to limited induction of effector T cells associated with disappointing clinical efficacy. This was likely due to the generation of anergic CD8 T cells as a result of a lack of CD4 T cell help. This anergy probably resulted from exogenous loading of the short epitope and direct presentation to CD8 T cells, thus bypassing intracellular processing of the antigen by DC and co-signaling by matured DC (3) On the other hand, vaccination with full length recombinant proteins does not seem to be the best alternative. Indeed, in vivo mouse studies showed that intracellular routes of cross presentation were more efficient with synthetic long peptide (SLP) than with full length antigen (4). Therefore nowadays, SLP, usually defined as 25-35 aa-long peptides encompassing a well-defined CD8 epitope extended to include putative CD4 epitopes are regarded as the most efficient immunogens. However, no rationale for designing optimal linker is already presented.

SLP are usually administered as a mix of up to a dozen units to cover either a wide range of HLA haplotype and/or a wide range of epitopes (5). Notably, synthetic long peptides have shown clinical efficiency against HPV induced cervical and vulvar neoplasia (6) and recently they have been used in melanoma patients to vaccinate them with neoepitopes (7). In most cases reported, the choice of the SLP relied primarily on a defined CD8 epitope and assumed the presence of a CD4 helper epitope in the vicinity. Alternative strategies for designing SLP vaccines rely on a careful selection of well-defined CD8 and CD4 epitopes, for which a wide repertoire exists and/or elicits strong immune responses (8). Selection of both CD4 and CD8 epitopes offers a wide range of opportunities: separation of naturally overlapping epitopes, linking epitopes that are otherwise far apart on the natural antigen. It also allows the creation of chimeric epitopes containing for example a CD4 epitope from one antigen (9) coupled to a CD8 epitope from another tumor antigen. In line with this, universal CD4 helper epitopes, capable of binding to a broad range of HLA haplotypes, and thus eliciting responses in a large population of patients have been described (10).

SUMMARY OF THE INVENTION

The inventors have previously characterized MELOE-1 antigen as an IRES dependent, melanoma specific translation product from a lncRNA mainly transcribed in the melanocytic lineage (11-13). MELOE-1 contains numerous class II epitopes (14,15) and one HLA-A*0201-restricted CD8 epitope eliciting a frequent repertoire of high avidity T cells (16). Their previous studies allowed them to produce CD4 and CD8 T cells clones against these various epitopes which constitute valuable tools to study SLP processing and presentation by DC in vitro. Therefore, as a first step, using the MELOE-1 antigen as a model, they designed various SLPs comprising a CD4 epitope coupled to the CD8 epitope by a serie of linkers of 4 to 6 aa and studied the efficacy of T cell clone activation by SLP-loaded DC in vitro. More, considering the natural positioning of class II and class I epitopes in MELOE-1 (i.e. class II epitopes upstream of the class I epitope) and considering that processing of class I epitopes involves trimming of the NH2 terminus by ERAP enzymes in the reticulum to allow loading into class I, they chose to design their SLP with the class II epitope first then the linker and then the class I epitope whereas other teams designed their SLP in the other way (8,17). In addition, they selected the most efficient linker sequences for processing and presentation of the MELOE-1 epitopes. They then replaced the HLA*A0201-restricted MELOE-1 epitope by a HLA*A0201 Melan-A/MART-1 epitope with the same linkers and re-assessed cross-presentation by DC. They next evaluated the ability of a few selected SLPs to stimulate specific T cells proliferation of PBL from healthy donors in vitro. Finally, they explored the vaccination potential of their best SLP candidate in vivo in an HLA*A0201/HLA-DRB0101 transgenic mouse (18).

Thus, the present invention relates to a specific linker and a synthetic long peptide (SLP) comprising a CD4 class II peptide linked to a CD8 class I peptide by the specific linker. Particularly, the invention relates to the use of the SLP in the treatment of cancers, infectious diseases, inflammatory diseases or auto-immune diseases in a patient in need thereof. More particularly, the invention is defined by its claims.

DETAILED DESCRIPTION OF THE INVENTION

The inventors tested linkers to select SLP efficiently processed by antigen presenting cells (APC). After investigations, they concluded that a good sequence for the linker should contain the LSV motif as a core and that a good linker may contain the Xaa1-LSVXaa5-Xaa6 (SEQ ID NO: 1) motif with Xaa1 which can be an amino acid selected in the group consisting in alanine, leucine, valine, serine or Glycine and Xaa5 and Xaa6 which can be an optional amino acids selected in the group consisting in alanine, leucine, valine or Glycine. Such a designed linker allows a cleavage by proteases like cathepsins and thus a good processing of the CD4 class II peptide and the CD8 class I peptide by APC. Moreover, such a linker avoids the formation of neo-antigen which is a really important aspect in the context of a vaccine strategy.

Thus, a first aspect of the invention relates to a peptidic linker comprising the amino acids sequence: Xaa1-LSV-Xaa5-Xaa6 (SEQ ID NO:1) wherein Xaa1 is an amino acid selected in the group consisting in alanine (ala or A), leucine (leu or L), valine (val or V), serine (Ser or S) or Glycine (Gly or G) and Xaa5 and Xaa6 are optional amino acids selected in the group consisting in alanine (ala or A), leucine (leu or L), valine (val or V), Glycine (Gly or G) or no amino acid.

In other word, the peptidic linker may also have a sequence Xaa1-LSV (SEQ ID NO:2) wherein Xaa1 is an amino acid selected in the group consisting in alanine (ala or A), leucine (leu or L), valine (val or V), serine (Ser or S) or Glycine (Gly or G) or Xaa1-LSV-Xaa5 (SEQ ID NO:3) wherein Xaa1 is an amino acid selected in the group consisting in alanine (ala or A), leucine (leu or L), valine (val or V), serine (Ser or S) or Glycine (Gly or G) and Xaa5 is an amino acid selected in the group consisting in alanine (ala or A), leucine (leu or L), valine (val or V) or Glycine (Gly or G).

In a particular embodiment, the peptidic linker consists in the amino acids sequence: Xaa1-LSV-Xaa5-Xaa6 (SEQ ID NO:1) wherein Xaa1 is an amino acid selected in the group consisting in alanine (ala or A), leucine (leu or L), valine (val or V), serine (Ser or S) or Glycine (Gly or G) and Xaa5 and Xaa6 are optional amino acids selected in the group consisting in alanine (ala or A), leucine (leu or L), valine (val or V), Glycine (Gly or G) or no amino acid.

In a particular embodiment, the peptidic linker consists in the amino acids sequences LLSV (SEQ ID NO:4), VLSV (SEQ ID NO:5), SLSV (SEQ ID NO:6) or GLSV (SEQ ID NO:7).

In another particular embodiment, the peptidic linker consists in the amino acids sequences LLSVG (SEQ ID NO:8), LLSVGG (SEQ ID NO:9), VLSVG (SEQ ID NO:10), VLSVGG (SEQ ID NO:11), GLSVGG (SEQ ID NO:176), GLSVVV (SEQ ID NO:177), SLSVAA (SEQ ID NO:178), SLSVGG (SEQ ID NO:179), ALSVGG (SEQ ID NO:180) or LLSVGA (SEQ ID NO:191).

A second aspect of the invention relates to a synthetic long peptide (SLP) comprising a CD4 class II peptide linked to a CD8 class I peptide by a peptidic linker comprising the amino acids sequence Xaa1-LSVXaa5-Xaa6 (SEQ ID NO:1) wherein the CD4 class II peptide is linked at its C-terminal position to the peptidic linker and the CD8 class I peptide is linked at its N-terminal position to the peptidic linker and wherein Xaa1 is an amino acid selected in the group consisting in alanine (ala or A), leucine (leu or L), valine (val or V), serine (Ser or S) or Glycine (Gly or G) and Xaa5 and Xaa6 are optional amino acids selected in the group consisting in alanine (ala or A), leucine (leu or L), valine (val or V), Glycine (Gly or G) or no amino acid or a function-conservative variant thereof.

In a particular embodiment, the invention relates to a synthetic long peptide (SLP) consisting in a CD4 class II peptide linked to a CD8 class I peptide by a peptidic linker comprising or consisting in the amino acids sequence Xaa1-LSVXaa5-Xaa6 (SEQ ID NO:1) wherein the CD4 class II peptide is linked at its C-terminal position to the peptidic linker and the CD8 class I peptide is linked at its N-terminal position to the peptidic linker and wherein Xaa1 is an amino acid selected in the group consisting in alanine (ala or A), leucine (leu or L), valine (val or V), serine (Ser or S) or Glycine (Gly or G) and Xaa5 and Xaa6 are optional amino acids selected in the group consisting in alanine (ala or A), leucine (leu or L), valine (val or V), Glycine (Gly or G) or no amino acid or a function-conservative variant thereof.

As used herein, the term "CD4 class II peptide" denotes a part of a peptide that is specifically recognized by the CD4 T lymphocytes of the immune system.

As used herein, the term "CD8 class I peptide" denotes a peptide that is specifically recognized by the CD8 T lymphocytes of the immune system.

According to the invention, "CD4 class II peptide" or CD4 class II antigen peptide" or CD4 class II epitope" have the same meaning.

According to the invention, "CD8 class I peptide" or CD8 class I antigen peptide" or CD8 class I epitope" have the same meaning.

According to the invention, the terms "antigen peptide", "epitope", "class I epitope", "class II epitope" or "epitope peptide" have the same meaning and denote peptides that is specifically recognized by the CD4 or CD8 T lymphocytes of the immune system.

As used herein, the term "function-conservative variants" refers to those in which a given amino acid residue in a protein or enzyme has been changed (inserted, deleted or substituted) without altering the overall conformation and function of the polypeptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, particularly at least 75%, more particularly at least 85%, still particularly at least 90%, and even more particularly at least 95%, and which has the same or substantially similar properties or functions as the native or parent protein to which it is compared. Two amino acid sequences are "substantially homologous" or "substantially similar" when greater than 80%, particularly greater than 85%, particularly greater than 90% of the amino acids are identical, or greater than about 90%, particularly greater than 95%, are similar (functionally identical) over the whole length of the shorter sequence. Particularly, the similar or homologous sequences are identified by alignment using, for example, the GCG (Genetics Computer Group, Program Manual for the GCG Package, Version 7, Madison, Wisconsin) pileup program, or any of sequence comparison algorithms such as BLAST, FASTA, etc.

As used herein, the term "synthetic long peptide" or "SLP" refers to an amino acid sequence having less than 50 amino acids or than less than 45 amino acids or less than 40 amino acids or less than 35 amino acids or less than 34 amino acids or less than 33 amino acids or less than 32 amino acids or less than 31 amino acids or less than 30 amino acids or less than 29 amino acids or less than 28 amino acids or less than 27 amino acids or less than 26 amino acids or less than 25 amino acids.

In a particular embodiment, the SLP of the invention may contain one or two more amino acids at their C and N-terminal parts.

As used herein, the term "CD4 class II peptide" or "CD8 class I peptide" encompasses amino acid sequences having less than 25 amino acids or less than 20 amino acids or less than 15 amino acids or less than 14 amino acids or less than 13 amino acids or less than 12 amino acids or less than 11 amino acids or less than 10 amino acids or less than 9 amino acids or less than 8 amino acids or less than 7 amino acids or less than 6 amino acids or less than 5 amino acids.

According to the invention, the SLP of the invention can be obtained by synthesizing the peptides according to methods for peptide synthesis known in the art.

Antigens and SLP Used in a Melanoma Context

The inventors worked particularly on melanoma and use CD8 class I and CD4 class II peptides derived from MELOE-1, MELOE-2 and Melan-A antigens as proof of concept.

Sequence of MELOE-1 (SEQ ID NO: 12):
MSCVGYPDEATSREQFLPSEGAACPPWHPSERISSTLNDECWPASL Sequence of MELOE-2 (SEQ ID NO: 13):
MSENAGGAVARTATAFCALVSPTPQPRCPPKPPLAALCQ Sequence of Melan-A (SEQ ID NO: 14):
MPREDAHFIYGYPKKGHGHSYTTAEEAAGIGILTVILGVLLLIGCWYCR
RRNGYRALMDKSLHVGTQCALTRRCPQEGFDHRDSKVSLQEKNCEPVVP
NAPPAYEKLSAEQSPPPYSP More particularly, the CD8 class I or CD4 class II peptides of the invention may comprise or consist of the amino acids motif derived from Melan-A:
E-Xaa2-AGIGILTV (SEQ ID NO:15)
  wherein Xaa2 is leucine (Leu or L), alanine (Ala or A), methionine (Met or M), valine (Val or V), isoleucine (Ile or I) or glutamine (Gln or Q).

In another embodiment, the CD8 class I or CD4 class II peptides comprise or consist of the amino acids motif derived from MELOE-1:
T-Xaa2-NDECWP-Xaa9 (SEQ ID NO:16)
  wherein Xaa2 is leucine (Leu or L), methionine (Met or M), valine (Val or V), isoleucine (Ile or I) or glutamine (Gln or Q) and X9 is alanine (Ala or A), valine (Val or V) or leucine (Leu or L).

In another embodiment, the CD8 class I or CD4 class II peptides comprise or consist of the amino acids motif derived from MELOE-2:
R-Xaa2-PPKPPL-Xaa9 (SEQ ID NO:17)
  wherein Xaa2 is cysteine (Cys or C), leucine (Leu or L), methionine (Met or M), valine (Val or V), isoleucine (Ile or I) or glutamine (Gln or Q) and Xaa9 is alanine (Ala or A), valine (Val or V) or leucine (Leu or L).

Particularly, the CD8 class I and CD4 class II peptides of the invention can be the peptides described in tables A and B.

TABLE A

CD4 class II peptides used as example

| SEQ ID number | Sequences | CD4 class II peptides |
|---|---|---|
| MELOE-1 SEQ ID NO: 18 | RISSTLNDECWPA | DQB1*0603 |
| MELOE-1 SEQ ID NO: 19 | ERISSTLNDECWPA | DQB1*0201 |
| MELOE-1 SEQ ID NO: 20 | PDEATSREQFL | DQB1*0202 |
| MELOE-1 SEQ ID NO: 21 | REQFLPSEGAACPPW | DRB1*0101 |
| MELOE-1 SEQ ID NO: 22 | EQFLPSEGAACPPW | DRB1*0505 |
| MELOE-1 SEQ ID NO: 23 | QFLPSEGAACPPW | DRB1*1101 |

TABLE A-continued

CD4 class II peptides used as example

| SEQ ID number | Sequences | CD4 class II peptides |
|---|---|---|
| MELOE-1 SEQ ID NO: 24 | TSREQFLPSEGAA | DRB1*0101 |
| MELOE-1 SEQ ID NO: 25 | SREQFLPSEGAAC | DRB1*0101 |
| MELOE-1 SEQ ID NO: 26 | CPPWHPSERISSTL | DRB1*1101 |
| MELOE-1 SEQ ID NO: 27 | CPPWHPSERISST | DRB1*1101 |
| Melan-A SEQ ID NO: 28 | EELAGIGILTVI | DRB1*0301/ DQB1*0601 |
| Melan-A SEQ ID NO: 29 | ELAGIGILTVILGVL | DRB1*0101 |
| Melan-A SEQ ID NO: 30 | MPREDAHFIYGYPKKGHGHS | DRB1*1101 |

TABLE B

CD8 class I peptides used as example

| SEQ ID number | Sequences | CD8 class I peptides |
|---|---|---|
| MELOE-1 SEQ ID NO: 31 | TLNDECWPA | HLA-A*0201 |
| MELOE-1 SEQ ID NO: 32 | TMNDECWPA | HLA-A*0201 |
| MELOE-1 SEQ ID NO: 33 | TVNDECWPA | HLA-A*0201 |
| MELOE-1 SEQ ID NO: 34 | TINDECWPA | HLA-A*0201 |
| MELOE-1 SEQ ID NO: 35 | TQNDECWPA | HLA-A*0201 |
| MELOE-1 SEQ ID NO: 36 | TLNDECWPV | HLA-A*0201 |
| MELOE-1 SEQ ID NO: 37 | TMNDECWPV | HLA-A*0201 |
| MELOE-1 SEQ ID NO: 38 | TVNDECWPV | HLA-A*0201 |
| MELOE-1 SEQ ID NO: 39 | TINDECWPV | HLA-A*0201 |
| MELOE-1 SEQ ID NO: 40 | TQNDECWPV | HLA-A*0201 |
| MELOE-1 SEQ ID NO: 41 | TLNDECWPL | HLA-A*0201 |
| MELOE-1 SEQ ID NO: 42 | TMNDECWPL | HLA-A*0201 |
| MELOE-1 SEQ ID NO: 43 | TVNDECWPL | HLA-A*0201 |
| MELOE-1 SEQ ID NO: 44 | TINDECWPL | HLA-A*0201 |
| MELOE-1 SEQ ID NO: 45 | TQNDECWPL | HLA-A*0201 |
| MELOE-2 SEQ ID NO: 46 | RCPPKPPLA | HLA-A*0201 |
| MELOE-2 SEQ ID NO: 47 | RLPPKPPLA | HLA-A*0201 |
| MELOE-2 SEQ ID NO: 48 | RMPPKPPLA | HLA-A*0201 |
| MELOE-2 SEQ ID NO: 49 | RVPPKPPLA | HLA-A*0201 |
| MELOE-2 SEQ ID NO: 50 | RIPPKPPLA | HLA-A*0201 |
| MELOE-2 SEQ ID NO: 51 | RQPPKPPLA | HLA-A*0201 |
| MELOE-2 SEQ ID NO: 52 | RCPPKPPLV | HLA-A*0201 |
| MELOE-2 SEQ ID NO: 53 | RLPPKPPLV | HLA-A*0201 |
| MELOE-2 SEQ ID NO: 54 | RMPPKPPLV | HLA-A*0201 |

TABLE B-continued

CD8 class I peptides used as example

| SEQ ID number | Sequences | CD8 class I peptides |
|---|---|---|
| MELOE-2 SEQ ID NO: 55 | RVPPKPPLV | HLA-A*0201 |
| MELOE-2 SEQ ID NO: 56 | RIPPKPPLV | HLA-A*0201 |
| MELOE-2 SEQ ID NO: 57 | RQPPKPPLV | HLA-A*0201 |
| MELOE-2 SEQ ID NO: 58 | RCPPKPPLL | HLA-A*0201 |
| MELOE-2 SEQ ID NO: 59 | RLPPKPPLL | HLA-A*0201 |
| MELOE-2 SEQ ID NO: 60 | RMPPKPPLL | HLA-A*0201 |
| MELOE-2 SEQ ID NO: 61 | RVPPKPPLL | HLA-A*0201 |
| MELOE-2 SEQ ID NO: 62 | RIPPKPPLL | HLA-A*0201 |
| MELOE-2 SEQ ID NO: 63 | RQPPKPPLL | HLA-A*0201 |
| Melan-A SEQ ID NO: 64 | ELAGIGILTV | HLA-A*0201 |

In a particular embodiment the SLP of the invention can comprises the CD8 class I peptide 36-44 of MELOE-1 (SEQ ID NO:31). Thus, the SLP of the invention may consist in the SLP of sequences:

(SEQ ID NO: 65)
TSREQFLPSEGAACPPWLLSVTLNDECWPASL;

(SEQ ID NO: 66)
REQFLPSEGAACPPWLLSVTLNDECWP;

(SEQ ID NO: 67)
REQFLPSEGAACPPWVLSVGGTLNDECWPA;

(SEQ ID NO: 68)
REQFLPSEGAACPPWLLSVGGTLNDECWPA;

(SEQ ID NO: 69)
TSREQFLPSEGAACPPWVLSVGGTLNDECWPASL;

(SEQ ID NO: 70)
REQFLPSEGAACPPWVLSVGATLNDECWPA;

(SEQ ID NO: 71)
TSREQFLPSEGAACPPWVLSVGTLNDECWPASL;

(SEQ ID NO: 72)
REQFLPSEGAACPPWVLSVGTLNDECWPA;

(SEQ ID NO: 73)
TSREQFLPSEGAACPPWSLSVAATLNDECWPASL;

(SEQ ID NO: 74)
REQFLPSEGAACPPWSLSVAATLNDECWPA;

(SEQ ID NO: 75)
TSREQFLPSEGAACPPWSLSVGGTLNDECWPASL;

(SEQ ID NO: 76)
REQFLPSEGAACPPWSLSVGGTLNDECWPA;

(SEQ ID NO: 77)
TSREQFLPSEGAACPPWALSVGGTLNDECWPASL;

(SEQ ID NO: 78)
REQFLPSEGAACPPWALSVGGTLNDECWPA;

(SEQ ID NO: 79)
TSREQFLPSEGAACPPWPLSVIITLNDECWPASL;

(SEQ ID NO: 80)
REQFLPSEGAACPPWPLSVIITLNDECWPA;

(SEQ ID NO: 81)
TSREQFLPSEGAACPPWGLSVGGTLNDECWPASL;

(SEQ ID NO: 82)
REQFLPSEGAACPPWGLSVGGTLNDECWPA;

(SEQ ID NO: 83)
TSREQFLPSEGAACPPWLSVTLNDECWPASL;

(SEQ ID NO: 84)
REQFLPSEGAACPPWLSVTLNDECWPA;

(SEQ ID NO: 85)
TSREQFLPSEGAACPPWGLSVVVTLNDECWPASL;

(SEQ ID NO: 86)
REQFLPSEGAACPPWGLSVVVTLNDECWPA;

(SEQ ID NO: 87)
TSREQFLPSEGAACPPWLLSVGGTLNDECWPASL;

(SEQ ID NO: 88)
REQFLPSEGAACPPWLLSVGATLNDECWPA;

(SEQ ID NO: 89)
TSREQFLPSEGAACPPWLLSVGTLNDECWPASL;

(SEQ ID NO: 90)
REQFLPSEGAACPPWLLSVGTLNDECWPA;

(SEQ ID NO: 91)
YRKSVWSKLQSIGIRQHSLSVAATLNDECWPASL;

(SEQ ID NO: 92)
KSVWSKLQSIGIRQHSLSVAATLNDECWPA.

In a particular embodiment the SLP of the invention can comprise the CD8 class I peptide 26-(A27L)-35 from Melan-A (SEQ ID NO:64). Thus, the SLP of the invention may consist in the SLP of sequences:

(SEQ ID NO: 93)
TSREQFLPSEGAACPPWLLSVELAGIGILTVIL;

(SEQ ID NO: 94)
REQFLPSEGAACPPWLLSVELAGIGILTV;

(SEQ ID NO: 95)
REQFLPSEGAACPPWLLSVGGELAGIGILTV;

(SEQ ID NO: 96)
TSREQFLPSEGAACPPWLLSVGGELAGIGILTVIL;

(SEQ ID NO: 97)
REQFLPSEGAACPPWLLSVGAELAGIGILTV;

(SEQ ID NO: 98)
TSREQFLPSEGAACPPWVLSVGGELAGIGILTV;

(SEQ ID NO: 99)
REQFLPSEGAACPPWVLSVGGELAGIGIL;

(SEQ ID NO: 100)
TSREQFLPSEGAACPPWLSVELAGIGILTVIL;

(SEQ ID NO: 101)
REQFLPSEGAACPPWLSVELAGIGILTV;

(SEQ ID NO: 102)
TSREQFLPSEGAACPPWLLSVGELAGIGILTVIL;

(SEQ ID NO: 103)
TSREQFLPSEGAACPPWVLSVGELAGIGILTVIL;

```
REQFLPSEGAACPPWVLSVGELAGIGILTV;                    (SEQ ID NO: 104)

TSREQFLPSEGAACPPWSLSVAAELAGIGILTVIL;               (SEQ ID NO: 105)

REQFLPSEGAACPPWSLSVAAELAGIGILTV;                   (SEQ ID NO: 106)

TSREQFLPSEGAACPPWSLSVGGELAGIGILTVIL;               (SEQ ID NO: 107)

REQFLPSEGAACPPWSLSVGGELAGIGILTV;                   (SEQ ID NO: 108)

TSREQFLPSEGAACPPWALSVGGELAGIGILTVIL;               (SEQ ID NO: 109)

REQFLPSEGAACPPWALSVGGELAGIGILTV;                   (SEQ ID NO: 110)

TSREQFLPSEGAACPPWPLSVIIELAGIGILTVIL;               (SEQ ID NO: 111)

REQFLPSEGAACPPWPLSVIIELAGIGILTV;                   (SEQ ID NO: 112)

TSREQFLPSEGAACPPWGLSVGGELAGIGILTVIL;               (SEQ ID NO: 113)

REQFLPSEGAACPPWGLSVGGELAGIGILTV;                   (SEQ ID NO: 114)

TSREQFLPSEGAACPPWGLSVVVELAGIGILTVIL;               (SEQ ID NO: 115)

REQFLPSEGAACPPWGLSVVVELAGIGILTV;                   (SEQ ID NO: 116)

TSREQFLPSEGAACPPWLLSVGAELAGIGILTVIL;               (SEQ ID NO: 117)

REQFLPSEGAACPPWLLSVGELAGIGILTV;                    (SEQ ID NO: 118)

YRKSVWSKLQSIGIRQHSLSVAAELAGIGILTVIL;               (SEQ ID NO: 119)

KSVWSKLQSIGIRQHSLSVAAELAGIGILTV.                   (SEQ ID NO: 120)
```

Others Kind of Antigens and SLP Used in a Cancer Context

The inventors work also on other cancer contexts and use CD8 class I and CD4 class II peptides as proof of concept. Particularly, the inventors used peptides derived from HTERT, NY-ESO-1 and GP100 proteins. These peptides derives from these proteins may be used particularly in colon, lung, kidney cancers context and also in melanoma.

Peptides Derived from the HTERT Protein:

CD8 class I and CD4 class II peptides derived from the protein hTERT can be used to generate SLP and can be used in a tumoral context.

In a particular embodiment, CD8 class I and CD4 class II peptides derived from the protein HTERT may be selected in the group consisting of: KSVWSKLQSIGIRQH (SEQ ID NO:121), GTAFVQMPAHGLFPW (SEQ ID NO:122), SLCYSILKAKNAGMS (SEQ ID NO:123), PAAFRALVAQCLVCV (SEQ ID NO:124), MPRAPRCRA (SEQ ID NO:125), APRCRAVRSL (SEQ ID NO:126), APSFRQVSCL (SEQ ID NO:127), RPAEEATSL (SEQ ID NO:128), RPSFLLSSL (SEQ ID NO:129), RPSLTGARRL (SEQ ID NO:130), DPRRLVQLL (SEQ ID NO:131), FVRACLRRL (SEQ ID NO:132), AGRNMRRKL (SEQ ID NO:133), LPGTTLTAL (SEQ ID NO:134), LPSPKFTIL (SEQ ID NO:135), RPSLTGARRL (SEQ ID NO:136), APSFRQVSCL (SEQ ID NO:137), APRCRAVRSL (SEQ ID NO:138), DPRRLVQLL (SEQ ID NO:139), FVRACLRRL (SEQ ID NO:140), AGRNMRRKL (SEQ ID NO:141), LPGTTLTAL (SEQ ID NO:142), and LPSPKFTIL (SEQ ID NO:143) (see for example the patent applications WO2013135553 and WO2007014740).

According to the invention, some SLP using hTERT peptides in combination with MELOE-1 peptides can be generated.

For example, these SLP may be selected in the group consisting of:

```
YRKSVWSKLQSIGIRQHSLSVAATLNDECWPASL,                (SEQ ID NO: 159)

KSVWSKLQSIGIRQHSLSVAATLNDECWPA,                    (SEQ ID NO: 168)

YRKSVWSKLQSIGIRQHLLSVGGTLNDECWPASL,                (SEQ ID NO: 181)

KSVWSKLQSIGIRQHLLSVGGTLNDECWPA,                    (SEQ ID NO: 182)

YRKSVWSKLQSIGIRQHLLSVGATLNDECWPASL,                (SEQ ID NO: 183)

KSVWSKLQSIGIRQHLLSVGATLNDECWPA.                    (SEQ ID NO. 184)
```

According to the invention, some SLP using hTERT peptides in combination with Melan-A peptides can be generated.

For example, these SLP may be selected in the group consisting of:

```
YRKSVWSKLQSIGIRQHSLSVAAELAGIGILTVIL,               (SEQ ID NO: 185)

KSVWSKLQSIGIRQHSLSVAAELAGIGILTV,                   (SEQ ID NO: 186)

YRKSVWSKLQSIGIRQHLLSVGGELAGIGILTVIL,               (SEQ ID NO: 187)

KSVWSKLQSIGIRQHLLSVGGELAGIGILTV,                   (SEQ ID NO: 188)

YRKSVWSKLQSIGIRQHLLSVGAELAGIGILTVIL,               (SEQ ID NO: 189)

KSVWSKLQSIGIRQHLLSVGAELAGIGILTV.                   (SEQ ID NO: 190)
```

Peptides Derived from the NY-ESO-1 Protein:

CD8 class I and CD4 class II peptides derived from the protein NY-ESO-1 can be used to generate SLP and can be used in a tumoral context.

In a particular embodiment, CD8 class I and CD4 class II peptides derived from the protein NY-ESO-1 may be the peptide SLLMWITQC (SEQ ID NO:144) or peptides selected in the patent application WO2007017686.

According to the invention, some SLP using hTERT peptides in combination with NY-ESO-1 peptides can be generated.

For example, these SLP may be selected in the group consisting of:

```
                                          (SEQ ID NO: 145)
KSVWSKLQSIGIRQHGLSVGGSLLMWITQC, (SEQ ID NO: 146)
KSVWSKLQSIGIRQHSLSVAASLLMWITQC,
and (SEQ ID NO: 147)
KSVWSKLQSIGIRQHLLSVGGSLLMWITQC.
```

Peptides Derived from the GP100 Protein:

CD8 class I and CD4 class II peptides derived from the protein GP100 can be used to generate SLP and can be used in a tumoral context.

In a particular embodiment, CD8 class I and CD4 class II peptides derived from the protein GP100 may be used. For example, these peptides can be the peptides of the table C.

TABLE C

CD4 class II and CD8 class I peptides derived from the GP100 protein used as example

| SEQ ID number | Sequences | Class of the peptide |
|---|---|---|
| | | CD8 class I peptide |
| GP100 SEQ ID NO: 148 | KTWGQYWQV | HLA-A*0201 |
| GP100 SEQ ID NO: 149 | MLGTHTMEV | HLA-A*0201 |
| GP100 SEQ ID NO: 150 | YLEPGPVTA | HLA-A*0201 |
| GP100 SEQ ID NO: 151 | ALLAVGATK | HLA-A*0301 |
| GP100 SEQ ID NO: 152 | RSYVPLAHR | HLA-A*0301 |
| GP100 SEQ ID NO: 153 | ALNFPGSQK | HLA-A*1101 |
| GP100 SEQ ID NO: 154 | VPLDCVLYRY | HLA-B*3501 |
| GP100 SEQ ID NO: 155 | SREQFLPSEGAAC | DRB1*0101 |
| | | CD4 class II peptide |
| GP100 SEQ ID NO: 156 | WNRQLYPEWTEAQRLD | DRB1*0401 |
| GP100 SEQ ID NO: 157 | TTEWVETTARELPIPEPE | DRB1*0701 |
| GP100 SEQ ID NO: 158 | GRAMLGTHTMEVTVY | DQB1*0601 |

In one embodiment, the SLP according to the invention comprises at least 70% identity over the SLP of the invention described in the invention, even more particularly at least 80%, 81%, 82%, 83%, 84%, 85%, 86%, 87%, 88%, 89%, 90%, 91%, 92%, 93%, 94%, 95%, 96%, 97%, 98%, 99% and is still able to be efficiently processed by antigen presenting cells.

In another embodiment, the SLP according to the invention consists in an amino acid sequence as set forth in SEQ ID NO:65 to 120, SEQ ID NO:145 to 147, SEQ ID NO:159, SEQ ID NO:168 or SEQ ID NO:181 to 189 or a variant thereof.

The invention also encompasses SLP that are function-conservative variants of SLP comprising SEQ ID NO:65 to 120 and SEQ ID NO:145 to 147 SEQ ID NO:159, SEQ ID NO:168 or SEQ ID NO:181 to 189 as described in the present invention.

Typically, the invention encompasses peptides substantially identical to CD8 class I and CD4 class II peptides comprising an amino acid sequence as set forth in SEQ ID NO:15 to 64 and SEQ ID NO: 121 to 144 and SEQ ID NO:148 to 158 in which one or more residues have been conservatively substituted with a functionally similar residue and which displays the functional aspects of the antigen peptides comprising an amino acid sequence as set forth in SEQ ID NO:13 to 62, SEQ ID NO:121 to 144 or SEQ ID NO:148 to 158 as described here above, i.e. being still able to be efficiently processed by antigen presenting cells in substantially the same way as a peptide consisting of the given amino acid sequence.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a patient peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

Nucleic Acids, Vectors, Recombinant Host Cells and Uses Thereof

Another object of the invention relates to a nucleic acid sequence encoding a linker or an SLP according to the invention.

Another object of the invention relates to an expression vector comprising a nucleic acid sequence encoding an SLP according to the invention.

According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above.

According to the invention, examples of host cells that may be used are eukaryote cells, such as animal, plant, insect and yeast cells and prokaryotes cells, such as *E. coli*. The means by which the vector carrying the gene may be introduced into the cells include, but are not limited to, microinjection, electroporation, transduction, or transfection using DEAE-dextran, lipofection, calcium phosphate or other procedures known to one skilled in the art.

In a preferred embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC #CRL1573), T2 cells, dendritic cells, or monocytes.

Therapeutic Use

Another object of the invention relates to the SLP as described above, or to the nucleic acid sequence as described here above or to the vector as described here above or the host cell as described here above for use as a medicament.

In a particular embodiment, the invention relates to the SLP as described above, or to the nucleic acid sequence as described here above or to the vector as described here above or the host cell as described here above for use as a vaccine.

In one embodiment the SLP as described above, or to the nucleic acid sequence as described here above or to the vector as described here above or the host cell as described here above may be used in the treatment of cancer, infectious diseases, inflammatory diseases or auto-immune diseases.

Thus, in another embodiment, the SLP according to the invention relates to an SLP as described above, or to the nucleic acid sequence as described here above or to the vector as described here above or the host cell as described here above for use in the treatment of cancers, infectious diseases, inflammatory diseases or auto-immune diseases in a patient in need thereof.

Particularly, the SLP as described above, or to the nucleic acid sequence as described here above or to the vector as described here above or the host cell as described here above may be used in the treatment of a cancer in a patient in need thereof.

In one embodiment, the cancer may be a cancer selected from the group consisting in adrenal cortical cancer, anal cancer, bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma,), vaginal cancer, vulvar cancer, and uterine cancer (e.g. uterine leiomyosarcoma).

The inventors particularly tested some SLP in melanoma context but also in colon, lung, kidney cancer.

Thus, in a particular embodiment, the cancer is a colon, lung or kidney cancer or a melanoma.

The term "melanoma" as used herein includes, but is not limited to, all types of melanocytes cancers at all stages of progression like metastatic melanocytes cancer.

As used herein, the term "patient" denotes a mammal, such as a rodent, a feline, a canine, and a primate. Particularly a patient according to the invention is a human.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

A "therapeutically effective amount" as used herein is intended for a minimal amount of active agent which is necessary to impart therapeutic benefit to a patient. For example, a "therapeutically effective amount of the active agent" to a patient is an amount of the active agent that induces, ameliorates or causes an improvement in the pathological symptoms, disease progression, or physical conditions associated with the disease affecting the patient.

In a particular embodiment, the invention relates a method for treating or preventing cancer, infectious diseases, inflammatory diseases or auto-immune diseases by administrating to a patient in need thereof a SLP as described above, or a nucleic acid sequence as described above or a vector as described above or a host cell as described above.

In one embodiment, a SLP as described above, or a nucleic acid sequence as described here above or a vector as described here above or a host cell as described here above can be administered in combination with a classical treatment of cancer, infectious diseases, inflammatory diseases or auto-immune diseases.

Thus, the invention also refers to a method for treating cancer, infectious diseases, inflammatory diseases or auto-immune diseases in a patient in need thereof comprising administering to said patient i) a therapeutically effective amount of a SLP according to the invention and ii) a classical treatment.

In other word, the invention refers to i) a SLP according to the invention and ii) a classical treatment for use in the treatment of cancer, infectious diseases, inflammatory diseases or auto-immune diseases.

As used herein, the term "classical treatment" refers to any compound, natural or synthetic, used for the treatment of cancer, infectious diseases, inflammatory diseases or auto-immune diseases.

In a particular embodiment, the classical treatment refers to radiation therapy, immunotherapy or chemotherapy.

As used herein, the term "chemotherapy" refers to use of chemotherapeutic agents to treat a subject. As used herein, the term "chemotherapeutic agent" refers to chemical compounds that are effective in inhibiting tumor growth.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a carnptothecin (including the synthetic analogue topotecan); a bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33: 183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERER, Rhone-Poulenc Rorer, Antony, France); chlorambucil; gemcitabine; 6-thioguanine; mercaptopurine; methotrexate; platinum analogs such as cisp latin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As used herein, the term "radiation therapy" or "radiotherapy" have their general meaning in the art and refers the treatment of cancer with ionizing radiation. Ionizing radiation deposits energy that injures or destroys cells in the area being treated (the target tissue) by damaging their genetic material, making it impossible for these cells to continue to grow. One type of radiation therapy commonly used involves photons, e.g. X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons produce x-rays of increasingly greater energy. The use of machines to focus radiation (such as x-rays) on a cancer site is called external beam radiation therapy. Gamma rays are another form of photons used in radiation therapy. Gamma rays are produced spontaneously as certain elements (such as radium, uranium, and cobalt 60) release radiation as they decompose, or decay. In some embodiments, the radiation therapy is external radiation therapy. Examples of external radiation therapy include, but are not limited to, conventional external beam radiation therapy; three-dimensional conformal radiation therapy (3D-CRT), which delivers shaped beams to closely fit the shape of a tumor from different directions; intensity modulated radiation therapy (IMRT), e.g., helical tomotherapy, which shapes the radiation beams to closely fit the shape of a tumor and also alters the radiation dose according to the shape of the tumor; conformal proton beam radiation therapy; image-guided radiation therapy (IGRT), which combines scanning and radiation technologies to provide real time images of a tumor to guide the radiation treatment; intraoperative radiation therapy (IORT), which delivers radiation directly to a tumor during surgery; stereotactic radiosurgery, which delivers a large, precise radiation dose to a small tumor area in a single session; hyperfractionated radiation therapy, e.g., continuous hyperfractionated accelerated radiation therapy (CHART), in which more than one treatment (fraction) of radiation therapy are given to a subject per day; and hypofractionated radiation therapy, in which larger doses of radiation therapy per fraction is given but fewer fractions.

As used herein, the term "immune checkpoint inhibitor" refers to molecules that totally or partially reduce, inhibit, interfere with or modulate one or more immune checkpoint proteins. As used herein, the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489). Examples of stimulatory checkpoint include CD27 CD28 CD40, CD122, CD137, OX40, GITR, and ICOS. Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because adenosine in the immune microenvironment, leading to the activation of the A2a receptor, is negative immune feedback loop and the tumor microenvironment has relatively high concentrations of adenosine. B7-H3, also called CD276, was originally understood to be a co-stimulatory molecule but is now regarded as co-inhibitory. B7-H4, also called VTCNI, is expressed by tumor cells and tumor-associated macrophages and plays a role in tumour escape. B and T Lymphocyte Attenuator (BTLA) and also called CD272, has HVEM (Herpesvirus Entry Mediator) as its ligand. Surface expression of BTLA is gradually downregulated during differentiation of human CD8+ T cells from the naive to effector cell phenotype, however tumor-specific human CD8+ T cells express high levels of BTLA. CTLA-4, Cytotoxic T-Lymphocyte-Associated protein 4 and also called CD152. Expression of CTLA-4 on Treg cells serves to control T cell proliferation. IDO, Indoleamine 2,3-dioxygenase, is a tryptophan catabolic enzyme. A related immune-inhibitory enzymes. Another important molecule is TDO, tryptophan 2,3-dioxygenase. IDO is known to suppress T and NK cells, generate and activate Tregs and myeloid-derived suppressor cells, and promote tumour angiogenesis. KIR, Killer-cell Immunoglobulin-like Receptor, is a receptor for MHC Class I molecules on Natural Killer cells. LAG3, Lymphocyte Activation Gene-3, works to suppress an immune response by action to Tregs as well as direct effects on CD8+ T cells. PD-1, Programmed Death 1 (PD-1) receptor, has two ligands, PD-L1 and PD-L2. This checkpoint is the target of Merck & Co.'s melanoma drug Keytruda, which gained FDA approval in September 2014. An advantage of targeting PD-1 is that it can restore immune function in the tumor microenvironment. TIM-3, short for T-cell Immunoglobulin domain and Mucin domain 3, expresses on activated human CD4+ T cells and regulates Th1 and Th17 cytokines. TIM-3 acts as a negative regulator of Th1/Tel function by triggering cell death upon interaction with its ligand, galectin-9. VISTA, Short for V-domain Ig suppressor of T cell activation, VISTA is primarily expressed on hematopoietic cells so that consistent expression of VISTA on leukocytes within tumors may allow VISTA blockade to be effective across a broad range of solid tumors. Tumor cells often take advantage of these checkpoints to escape detection by the immune system. Thus, inhibiting a checkpoint protein on the immune system may enhance the anti-tumor T-cell response.

In some embodiments, an immune checkpoint inhibitor refers to any compound inhibiting the function of an immune checkpoint protein. Inhibition includes reduction of function and full blockade. In some embodiments, the immune checkpoint inhibitor could be an antibody, synthetic or native sequence peptides, small molecules or aptamers which bind to the immune checkpoint proteins and their ligands.

In a particular embodiment, the immune checkpoint inhibitor is an antibody.

As used herein, the terms "combined treatment", "combined therapy" or "therapy combination" refer to a treatment that uses more than one medication. The combined therapy may be dual therapy or bi-therapy.

The medications used in the combined treatment according to the invention are administered to the subject simultaneously, separately or sequentially.

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different.

Vaccine Composition and Uses Thereof

The inventors test several SLP for anti-tumor vaccination but this vaccinal strategy may be useful and effective to prevent and treat lot of disease and especially infections and cancers. In any case, the idea is to induce a prolonged and potent CD4+ and CD8+ T-cell response against antigens express by tumors or pathogenic microorganisms like bacteria and virus.

Thus, another aspect of the invention relates to a vaccine composition comprising an SLP according to the invention.

In one embodiment, the vaccine composition is useful to prevent or treat cancers, infectious diseases, an inflammatory diseases or an auto-immune diseases.

In a particular embodiment, the disease is an infectious disease induces by a bacteria, a fungus or a virus.

In another particular embodiment, the disease is a cancer as described above. Particularly, the cancer is a melanoma.

The prophylactic administration of the vaccine composition of the invention should serve to prevent or attenuate disease like cancers, infectious diseases, an inflammatory diseases or an auto-immune diseases in a mammal. In a particularly embodiment, the prophylactic administration of the vaccine composition of the invention should serve to prevent or attenuate melanoma in a mammal. In a particular embodiment mammals, particularly human, at high risk for melanoma are prophylactically treated with the immunising composition of the invention. Examples of such mammals include, but are not limited to, humans with a family history of melanoma.

When provided therapeutically, the vaccine composition of the invention is provided to enhance the patient's own immune response to the melanoma antigen present on the melanoma or metastatic melanoma.

Thus, in one embodiment, the vaccine composition may be used as a therapeutic or prophylactic vaccine.

In one embodiment of the invention, the peptides of the invention may be conjugated with lipoprotein or administered in liposomal form or with adjuvant.

As used herein, the term "adjuvant" as used herein refers to a compound or a mixture that may be non-immunogenic when administered in the host alone, but that augments the host's immune response to an antigen when administered conjointly with that antigen.

In one embodiment, said vaccine composition is a pharmaceutical composition.

In such embodiment, said vaccine composition, for human use, comprises at least one antigen peptide as described here above or at least one antibody as described here above, together with one or more pharmaceutically acceptable carriers and, optionally, other therapeutic ingredients. The carrier(s) must be "acceptable" in the sense of being compatible with the other ingredients of the composition and not deleterious to the recipient thereof. The vaccine compositions may conveniently be presented in unit dosage form and may be prepared by any method well-known in the pharmaceutical art.

Vaccine compositions suitable for intravenous, intradermal, intramuscular, subcutaneous, or intraperitoneal administration conveniently comprise sterile aqueous solutions of the active agent with solutions which are particularly isotonic with the blood of the recipient. Such compositions may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The vaccine compositions of the invention may incorporate a stabilizer. Illustrative stabilizers are polyethylene glycol, proteins, saccharides, amino acids, inorganic acids, and organic acids which may be used either on their own or as admixtures. These stabilizers are particularly incorporated in an amount of 0.11-10,000 parts by weight per part by weight of active agent. If two or more stabilizers are to be used, their total amount is particularly within the range specified above. These stabilizers are used in aqueous solutions at the appropriate concentration and pH. The specific osmotic pressure of such aqueous solutions is generally in the range of 0.1-3.0 osmoles, particularly in the range of 0.8-1.2. The pH of the aqueous solution is adjusted to be within the range of 5.0-9.0, particularly within the range of 6-8.

Additional pharmaceutical methods may be employed to control the duration of action. Controlled release preparations may be achieved through the use of polymer to complex or absorb the peptides of the invention. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the antigen peptides of the invention into particles of a polymeric material such as polyesters, polyamino acids, hydrogels, poly(lactic acid) or ethylene vinylaceiate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Vaccination of a patient with the vaccine composition of the invention can be conducted by conventional methods, for example, in the presence of conventional adjuvants. Examples of conventional adjuvant include, but are not limited to, metal salts, oil in water emulsions, Toll like receptors agonists, saponins, lipid A, alkyl glucosaminide phosphate, Freund's adjuvant, keyhole limpet haemocyanin (KLH), mannan, BCG, alum, cytokines such as IL-1, IL-2, macrophage colony stimulating factor, and tumor necrosis factor; and other substances that act as immunostimulating agents such as muramyl peptides or bacterial cell wall components, toxins, toxoids and TLR ligands.

The vaccine composition can be administered by any route appropriate such as intravenous, intraperitoneal, intramuscular, subcutaneous, intra-dermic and the like. The immunising composition may be administered once or at periodic intervals until a significant immune response is obtained (for example the apparition, after vaccination, of lymphocytes T CD4 and CD8 specific of the vaccine peptides used).

If the patient to be immunized is already afflicted with cancer or metastatic cancer, the vaccine composition of the invention can be administered in conjunction with other therapeutic treatments. Examples of other therapeutic treatments includes, but are not limited to, adoptive T cell immunotherapy, coadministration of cytokines or other therapeutic drugs for cancer.

The dose of SLP of the invention to be administered to a patient may be adjusted as appropriate depending on, for example, the disease to be treated, the age and the body weight of said patient. Ranges of antigen peptides of the invention that may be administered are about 0.001 to about 100 mg per patient, preferred doses are about 0.01 to about 10 mg per patient.

The vaccine composition of the invention may be evaluated first in animal models, initially rodents, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, cancer patients can be tested. Conventional methods would be used to evaluate the immune response of the patient to determine the efficiency of the immunising composition.

Lymphocytes T and Uses Thereof

Another object of the invention relates to a T lymphocyte that recognizes specifically SLP of the invention.

In one embodiment of the invention, said T lymphocyte is a T CD4 or T CD8 lymphocyte.

In another embodiment of the invention, said T lymphocyte is a T cell clone.

In another embodiment, said T lymphocyte is a genetically modified T lymphocyte that expresses a TCR that recognizes specifically the SLP of the invention.

Another object of the invention is a composition for adoptive therapy comprising said T lymphocytes as described here above that recognizes specifically SLP of the invention.

In the case of melanoma, it has been observed that an adoptive immunotherapy wherein intratumoral T cell infiltrate taken from the patient to be treated are cultured ex vivo in large quantities, and then returned into the patient achieves a therapeutic gain.

In a particular embodiment, the T cells are contained in physiological saline, phosphate buffered saline (PBS), culture medium, or the like in order to their stable maintain. Administration may be achieved, for example, intravenously or intra-tumoraly. By returning the T cells that recognizes specifically the antigen peptide of the invention into the patient's body, the toxicity of said T cells, or the stimulation of CD8 cytotoxic T cells by said cells towards tumor cells is enhanced in the patient who is positive for the melanoma antigen peptide of the invention. The tumor cells are destroyed and thereby the treatment of tumor is achieved.

Examples of where T-lymphocytes can be isolated, include but are not limited to, peripheral blood cells lymphocytes (PBL), lymph nodes, or tumor infiltrating lymphocytes (TIL).

Such lymphocytes can be isolated from tumor or peripheral blood of the individual to be treated by methods known in the art and cultured in vitro. Lymphocytes are cultured in media such as RPMI or RPMI 1640 for 2-5 weeks, particularly for 2-3 weeks. Viability is assessed by trypan blue dye exclusion assay. The lymphocytes are exposed to the antigen peptide of the invention for all of the culture duration.

In a preferred embodiment the lymphocytes are exposed to the melanoma antigen peptide of the invention at a concentration of about 1 to about 10 micrograms (µg)/ml for all the duration of lymphocyte culture. Cytokines may be added to the lymphocyte culture such as IL-2.

The SLP of the invention may be added to the culture in presence of antigen presenting cells such as dendritic cells or allogeneic irradiated cancer cell line cells.

After being sensitized to the peptide, the T-lymphocytes are administered to the patient in need of such treatment.

Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the patient being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

Another object of the invention is a method for producing T lymphocytes that recognize specifically SLP of the invention, said method comprising the steps of:
(a) stimulating peripheral blood mononuclear cells (PBMCs) or tumor infiltrating lymphocytes (TIL) obtained from a patient with at least one SLP of the invention,
(b) enriching the population of T lymphocytes specific for the SLP used in (a),
(c) optionally cloning said population of T lymphocytes specific for the SLP used in (a).

Enrichment and/or cloning may be carried out by using an MHC/peptide multimer as described here above. Cloning may also be carried out by conventional methods.

Stimulation of PBMCs may be carried out with at least one SLP of the invention alone, or presented by an antigen presenting cell such as dendritic cells or allogeneic irradiated cancer cell line cells. Typically, cytokines such as IL-2 may also be added to the culture.

Another object of the invention is a composition for adoptive therapy that comprises lymphocytes that recognizes specifically a SLP of the invention for preventing or treating disease like cancers, infectious diseases, an inflammatory diseases or an auto-immune diseases and particularly melanoma in a patient in need thereof, wherein said T lymphocytes are to be re-administrated to the patient.

The invention will be further illustrated by the following figures and examples. However, these examples and figures should not be interpreted in any way as limiting the scope of the present invention.

FIGURES

According to the FIGS. 2 to 7 of the patent application, all the number of the peptidic sequences indicated in these figures correspond to the number of the peptidic sequences of the linker tested.

FIG. 1. Panel A. Representation of MELOE-1 antigen. MELOE-1 is a 46 aa antigen containing multiple class II epitopes presented in various HLA context and a HLA A*0201 restricted class I epitope. Depicted here are the epitopes used in this study. Panel B. Schematic representation of the Synthetic Long Peptide (SLP) used in this study. The designed SLP comprises a class II epitope in N-ter fused to a class I epitope via a cathepsin-sensitive linker. The SLP ranges from 30-35 amino acid length.

FIG. 2. Panel A. Titration curve of TNF-a production (intra-cellular staining and flow cytometry analysis) by a MELOE-1, HLA DRb1*11 restricted CD4 T cell clone activated by mature MO-DC loaded with relevant SLP (TSMELOE-1$_{24-37}$ xxxxMELOE-1$_{36-44}$ SL). Panel B. Titration curve of TNF-a production (intra-cellular staining and flow cytometry analysis) by a MELOE-1, HLA A*0201 restricted CD8 T cell clone activated by mature MO-DC loaded with relevant SLP (TSMELOE-1$_{24-37}$xxxxMELOE-1$_{36-44}$ SL).

Figure 3:
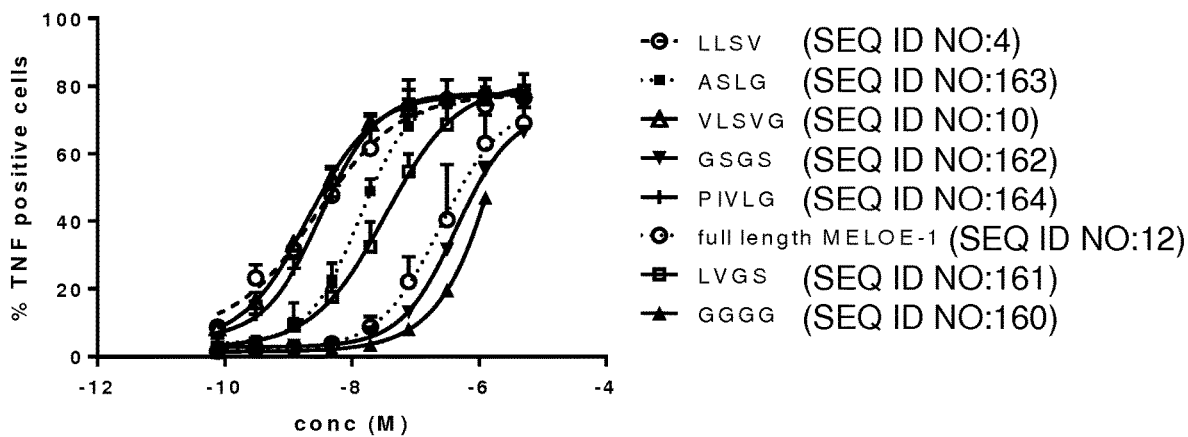

FIG. 3. Titration curve of TNF-a production (intra-cellular staining and flow cytometry analysis) by a MELOE-1, HLA A*0201 restricted CD8 T cell clone activated by mature MO-DC loaded with relevant SLP (TSMELOE-1$_{11-23}$xxxx-MELOE-1$_{36-44}$ SL).

Figure 4:
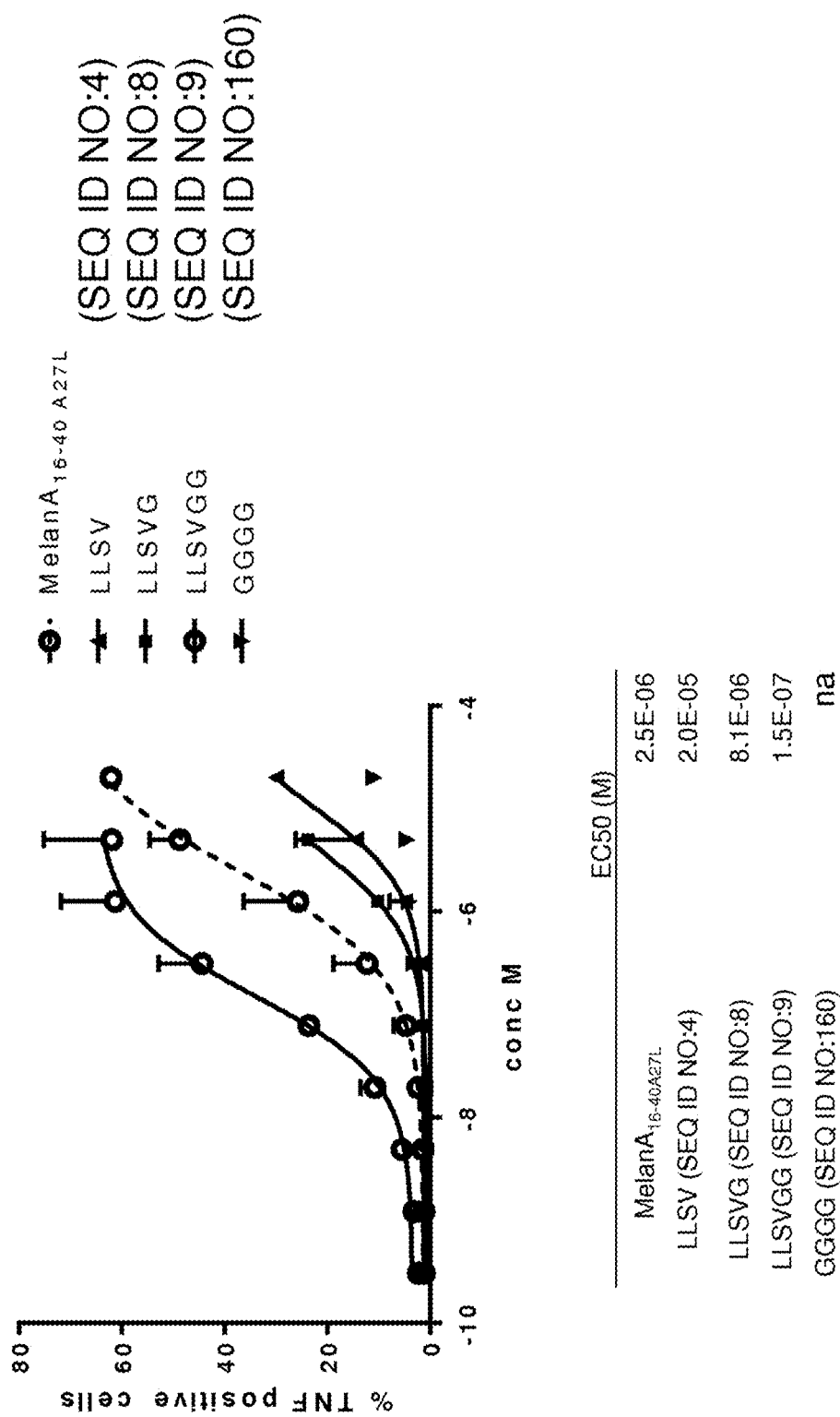

FIG. 4. Titration curve of TNF-a production (intra-cellular staining and flow cytometry analysis) by a MelanA, HLA A*0201 restricted CD8 T cell clone activated by mature MO-DC loaded with relevant SLP (TSMELOE-1$_{13-27}$xxxx-MelanA$_{26-35}$A27LIL).

Figure 5:
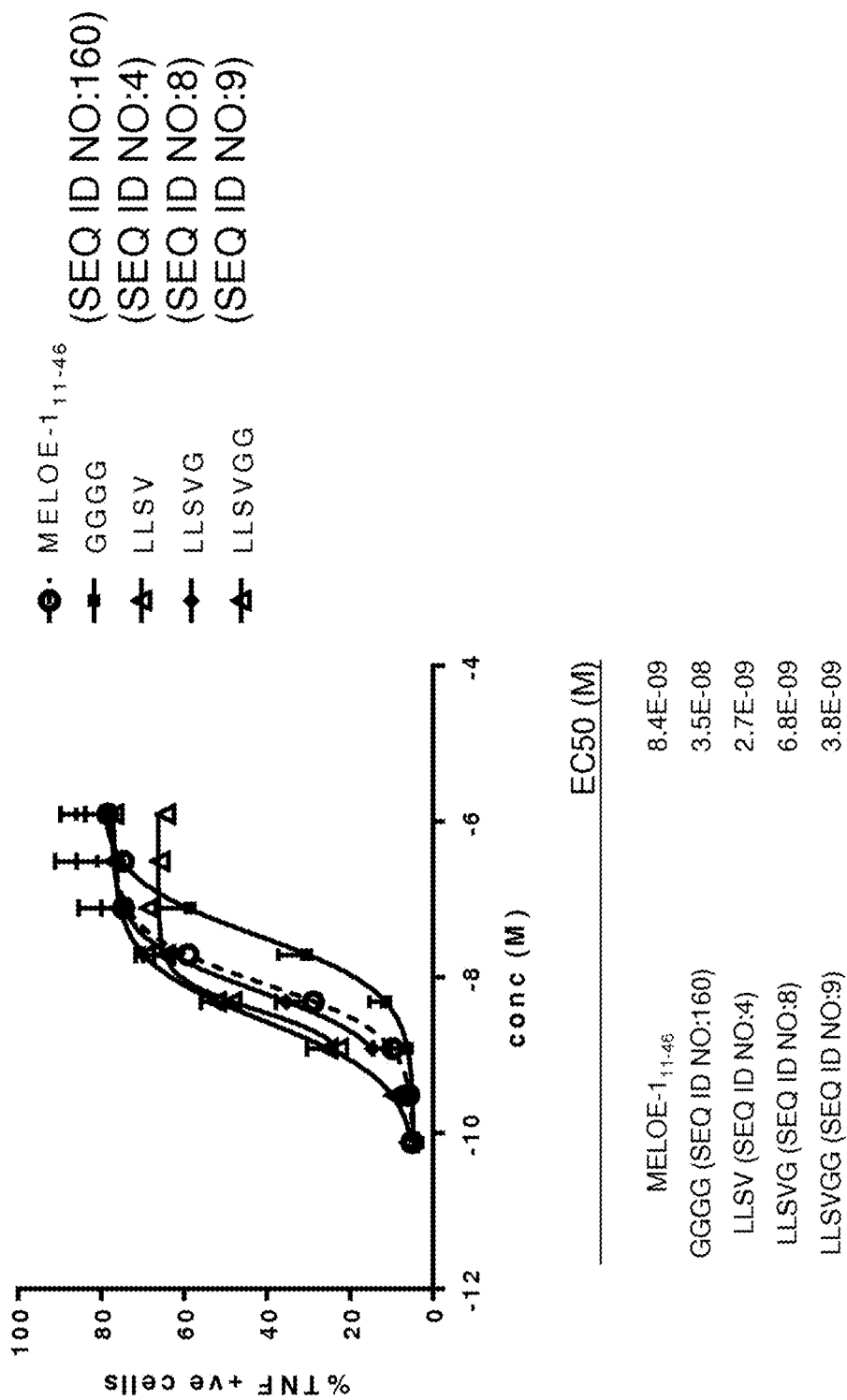

FIG. 5. Titration curve of TNF-a production (intra-cellular staining and flow cytometry analysis) by a MELOE-1, HLA DRB1*01 restricted CD4 T cell clone activated by mature MO-DC loaded with relevant SLP (TSMELOE-1$_{13-27}$xxxx-MELOE-1$_{36-44}$ SL).

FIG. 6. Panel A. in vitro PBMC stimulation with MELOE-1 SLP (TSMELOE-1$_{13-27}$xxxxMELOE-1$_{36-44}$ SL). Panel B. in vitro PBMC stimulation with MELOE-1 SLP (MELOE-1$_{13-27}$xxxxMELOE-1$_{36-44}$) containing various linkers or the native MELOE-1$_{11-46}$. Assessment of CD8 responses (number of positive microcultures and frequency of positive tetramer+/CD8+ lymphocytes per well) on a representative healthy donor (HD1). PBMC were stimulated in 96 well plates with cytokines cocktail and SLP (5 µM) for 21 days. Microcultures were screened by tetramer and CD8 double staining (cut off 0.5% of total). Panel C. Comparison of in vitro stimulation with the same aSLP as in panel B containing either the linker GGGG or the linker LLSVGG with PBMC from six healthy donors (black circle) and one melanoma patient (open triangle). **p=0.004, paired t-test. Panel D. in vitro PBMC stimulation with MelanA SLP (TSMELOE-1$_{13-27}$xxxxMelanA$_{26-35,A27L}$IL). Assessment of CD8 responses. PBMC from a healthy donor were stimulated and analysed as described above.

Figure 7A:
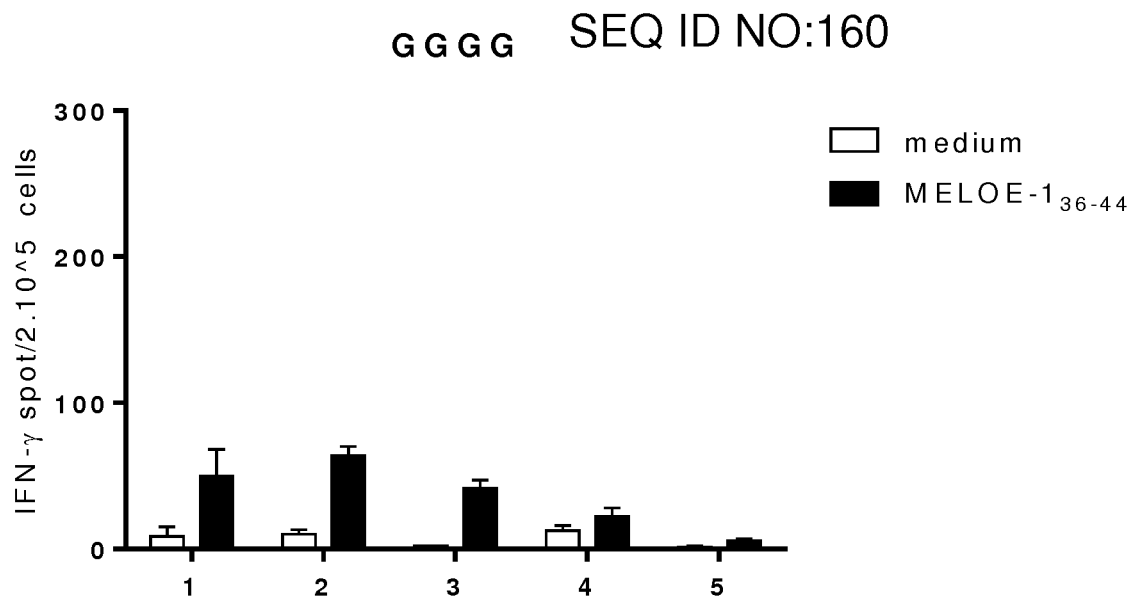
Figure 7B:
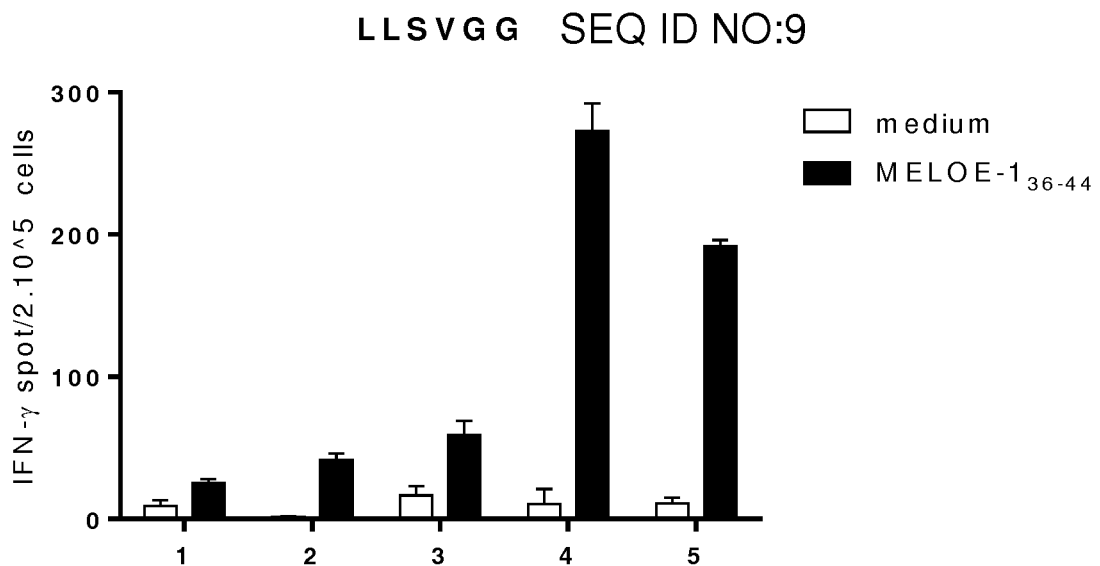

FIG. 7. Immunisation of HLA DRB1*01xHLA A*0201 transgenic mice with 2 SLP (TSMELOE-1$_{13-27}$xxxx-MELOE-1$_{36-44}$ SL). Mice received a prime injection of 100 µg of SLP followed by 2 boosts of 50 µg. SLP were emulsified in Incomplete Freund Adjuvant and administered with 50 µg of PolyI:C. Panel A. linker GGGG (SEQ ID NO:160). Panel B and C. linker LLSVGG (SEQ ID NO:9). At day 28 splenocytes were harvested, CD8+ T cells (panel A and B) or CD4+ T cells (panel C) were sorted and stimulated ex vivo with (black bars) or without (white bars) MELOE-1$_{36-44}$ peptide (panel A and B) or MELOE-1$_{13-27}$ (panel C). IFN-g production was assessed by ELISPOT.

FIG. 8. Panel A. Comparison of tumor sizes at day 36 in the three groups of mice, vaccinated with PBS, or adjuvant alone or aSLP containing the LLSVGG linker. Bars indicate median of each group. Panel B and C. Monitoring of the growth of subcutaneous SARC-A2-MELO-1 cells (2×105 cells) in PBS-treated mice (panel B) or vaccinated mice (panel C). Prime vaccination and boost are indicated by arrows.

TABLE 1

Evaluation of different linkers to promote cross-presentation of the SLP MELOE-1$_{13-27}$ xxxx MELOE-1$_{36-44}$

| Codes linkers | Sequence Linkers | Codes SLP | Fold change[a] | N[b] |
|---|---|---|---|---|
| MELOE-1$_{13-27}$ xxxx MELOE-1$_{36-44}$ | | | | |
| SEQ ID NO: 160 | GGGG | SEQ ID NO 173 | <0, 1 | 5 |
| SEQ ID NO: 4 | LLSV | SEQ ID NO: 64 | 6-14 | 4 |
| SEQ ID NO: 10 | VLSVG | SEQ ID NO: 71 | 3-13 | 2 |
| SEQ ID NO: 8 | LLSVG | SEQ ID NO: 89 | 10-20 | 3 |
| SEQ ID NO: 175 | PLSVII | SEQ ID NO: 79 | 2.3-10 | 2 |
| SEQ ID NO: 9 | LLSVGG | SEQ ID NO: 87 | 12-56 | 3 |
| SEQ ID NO: 11 | VLSVGG | SEQ ID NO: 69 | 1.5-2 | 2 |
| SEQ ID NO: 176 | GLSVGG | SEQ ID NO: 81 | 1 | |
| SEQ ID NO: 177 | GLSVVV | SEQ ID NO: 85 | 1 | |
| SEQ ID NO: 178 | SLSVAA | SEQ ID NO: 73 | 7-8 | |
| SEQ ID NO: 179 | SLSVGG | SEQ ID NO: 75 | 1-8 | |
| SEQ ID NO: 180 | ALSVGG | SEQ ID NO: 77 | 1-3 | |

[a]Fold change is calculated as EC50 (M) of MELOE-1$_{11-46}$/EC50 (M) SLP. EC50 were determined by the TNF-a response curves of a MELOE-1$_{11-46}$ specific CD8 T cell clone to SLP-loaded DC.
[b]number of independent experiments

TABLE 2

Assessement of CD8 responses in 5 healthy donors after PBMC stimulation in vitro with the SLP MELOE-1$_{13-27}$ xxxx MELOE-1$_{36-44}$

| Linkers | Codes SLP | HD1 | HD2 | HD3 | HD4 | HD5 |
|---|---|---|---|---|---|---|
| GGGG (SEQ ID NO: 160) | SEQ ID NO: 173 | 21/96 | 8/96 | 0/96 | 3/96 | |
| LLSV (SEQ ID NO: 4) | SEQ ID NO: 64 | 38/96* | 27/96** | 4/96 | 5/96 | |
| LLSVGG (SEQ ID NO: 9) | SEQ ID NO: 87 | | | | | 16/96 |
| Meloe-1$_{11-46}$ | / | | 18/96 | | | 8/96 |

TABLE 3

CD8 responses in HLA-DRB1*0101/HLA-A*0201 transgenic mice following immunization with SLP MELOE-1$_{13-27}$ xxxx MELOE-1$_{36-44}$.

| | Codes SLP | Exp#1 | Exp#2 | Exp#3 |
|---|---|---|---|---|
| MELOE-1$_{11-46}$ | / | | 0/5 | |
| Linker GGGG (SEQ ID NO: 160 | SEQ ID NO: 173 | 1/3 | | 3/5 |
| Linker LLSV (SEQ ID NO: 4) | SEQ ID NO: 64 | 2/3 | | |

TABLE 3-continued

CD8 responses in HLA-DRB1*0101/HLA-A*0201
transgenic mice following immunization with SLP MELOE-
$1_{13\text{-}27}$ xxxx MELOE-$1_{36\text{-}44}$.

|  | Codes SLP | Exp#1 | Exp#2 | Exp#3 |
|---|---|---|---|---|
| Linker LLSVG (SEQ ID NO: 8) | SEQ ID NO: 89 |  | 2/5 |  |
| Linker LLSVGG (SEQ ID NO: 9) | SEQ ID NO: 87 |  |  | 5/5 |

CD8+ splenocytes from immunized mice were tested by INFg-ELIspot following restimulation with the short epitope MELOE-$1_{36\text{-}44}$. Mice were considered positive if the number of spots after restimulation were more than twice the background level and above ten spots.

EXAMPLE

Material & Methods

Peptide Synthesis

Designed peptides were purchased at >90% purity (Protogenix, Genecust). Lyophilised powder was resuspended at 10 mM stock in DMSO and stored at −80° C. Purity was assessed by HPLC and precise quantification was calculated based on protein content analysis.

Mice

HLA-DRB1*0101/HLA-A*0201 transgenic mice (A2/DR1 mice) have been previously described (Pajot et al Eur. J. Immunol 2004, Dosset et al Clin Cancer Res, 2012, Rangan et al Oncotarget, 2017). Mice were bred and housed at Animalerie centrale UFC/UFR "SMP" Besançon. Female mice 6-10 weeks old were used in the experiments. All experiments were performed according to the good laboratory practices after agreement #58 by the local ethical committee.

Tumor Cell Line

The SARC-L1 cell line which spontaneously occurred in A2/DR1 mice was genetically modified to over-express HLA-A*0201 as previously described (Rangan et al Oncotarget, 2017). SARC-A2 cells were then transduced with a gammaretroviral dicistronic vector encoding the whole MELOE-1 antigen and, downstream of an IRES element, a puromycin N-acetyltransferase allowing selection of the transduced cells with puromycin (5 μg/mL). HLA-A*0201 expression was checked by flow cytometry. The capacity of the MELOE-1-transduced SARC-A2 (SARC-A2-MELOE-1) cells to present the A2-restricted MELOE-1 epitope was confirmed by their recognition by an HLA-A*0201-restricted T cell clone (data not shown).

Monocyte-Derived Dendritic Cells (MO-DC) Generation

Monocytes were purified from PBMC of HLA-A*0201 and/or HLA-DRB1*0101 healthy donors (Etablissement Français du Sang, Nantes, France) by negative selection using magnetic sorting (Stem Cell). Immature dendritic cells were generated by culturing monocytes in RPMI supplemented with 2% albumin, 1000 IU/mL of GM-CSF and 200 IU/mL of IL-4 (Cellgenix, Freiburg, Germany) for 5 days. Then, DC were pulsed with a concentration range of the various SLP tested and matured with 20 ng/ml of TNF-a and 50 μg/mL of PolyI:C (Sigma-Aldrich, France) for 16 h at 37° C.

T Cell Clone Assay

Once loaded and matured, MO-DC were washed twice in RPMI-2% albumin before being co-cultivated with T cell clones at a 1:1 ratio for 5 h in presence of brefeldinA (Sigma-Aldrich, 10 μg/ml). Intra-cellular TNF production was assessed by flow cytometry after 4% paraformaldehyde fixation and 0.1% saponin permeabilization (clone Mab11, 5 μg/ml, Biolegend, San Diego, USA). The percentage of TNF positive cells was assessed amongst CD8+(clone RPA-T8, BioLegend) or CD4+ cells (clone RPA-T4, BioLegend). Curve fitting and EC50 analysis were performed with GraphPad Prism v6.01 (log (agonist) vs. response, 4 parameters).

In Vitro Stimulation

At day 0, PBMCs were plated in 96 wells at $2\times10^5$ cells/wells in RMPI 1640 medium containing 8% human serum, 50 IU/mL II-2 (Proleukin, Novartis) and stimulated with 5-10 μM of various SLP tested. Medium was supplemented following the acDC protocol (Martinuzzi et al., 2011) by addition of 1000 U/mL of GM-CSF (CellGenix) and 500 UI/ml of II-4 (CellGenix). After 24 hours TNF-a (1000 IU/mL), IL-1β (10 ng/mL) and prostaglandin $E_2$ (1 μM) (R&D Systems, Minneapolis, USA) were added as DC maturation agents. After 21 days, the percentage of microcultures containing specific CD8+ T cells was evaluated by surface staining with anti-CD8 mAb and tetramer staining (HLA A*0201-MELOE-$1_{36\text{-}44}$ (SEQ ID NO:31) or MelanA$_{427L26\text{-}35}$. SEQ ID NO:64) (recombinant protein facility, P2 R, Nantes). Comparison of a number of positive microcultures after stimulation with aSLP in each subject was evaluated by Fisher's exact test and as a group using paired t-test (α=0.5%).

Mice and Immunization

HLA-DRB1*0101/HLA-A*0201 transgenic mice (A2/DR1 mice) were used to evaluate immunogenicity of peptides. Group of 5 female A2/DR1 mice (6 to 10 weeks) were immunized subcutaneously with 100 μg of each peptides emulsified in incomplete Freund adjuvant (v/v) plus 50 μg of polyI:C. At day 14 and day 28 boost vaccinations were performed with 50 μg of each peptide along with the same adjuvants. All experiments were carried out according to the good laboratory practices defined by the animal experimentation Rules in France.

ELISpot

Specific immune responses were evaluated 10 days after the last boost by ELISpot-IFN-g (Diaclone, France). Briefly, freshly isolated splenocytes or CD8 positive T cells from spleen (CD8+ T Cell Isolation Kit, Miltenyi Biotec) were incubated (2.105 cells per well) during 15-20 hours in ELISpot plate in the presence of the class I MELOE-1 epitope (5 μg/ml final) or medium (X-vivo, as negative control) or PMA-ionomycin (positive control). Ex vivo CD4 T cell responses were evaluated on the CD8 negative fraction as above with the HLA-DRB1*0101-restricted epitope MELOE-$1_{13\text{-}27}$. Spots were revealed according to the supplier's recommendations. Spot-forming cells were counted using the «C.T.L. Immunospot» system (Cellular Technology Ltd). Results were considered positive when the ELISPOT counts were >10 spots and above 2× the background (medium). (Dosset et al Clin Cancer Res, 2012)

Anti-Tumor Vaccination

A2/DR1 mice were subcutaneously injected with 2×105 SARC-A2-MELOE-1 cells in 100 μl in the right flank. The first vaccination with aSLP (100 μg in IFA, as above) or adjuvant alone or PBS started when tumor became detectable (around 10 mm2). A boost vaccination with 50 μg of aSLP was performed at day 20. Tumor growth was evaluated twice a week using a caliper and mice were euthanized when Results Design of SLP Our aim was to design SLP of 25-35aa long that could be efficiently processed by DC to generate both defined class I and class II restricted T cell epitopes. The rationale for designing our SLPs was as follows: we decided to place the class II-restricted epitope first, then the protease sensitive linker and then the class I-restricted epitope (FIG. 1B). We figured that with this design, even if protease cleavage generated a class I epitope elongated at the N-terminus, the trimming necessary for loading into HLA class I molecules would be performed by the physiological ERAD system in DC (Serwold, Nature 2002). On the other hand, the production of a slightly elongated class II-restricted epitope should not prevent its loading into class II molecules since class II HLA are much more permissive in terms of epitope length than class I HLA (O'Brien, Immunome Res 2008ref). The next critical choice which constitutes the core of this work was the amino-sequence of the linker peptide. Considering that SLP are internalized and processed by DC through the endosomal route ( ) the main enzymes involved in initial processing of SLP are cathepsins. They represent a large family with multiple cathepsins involved in antigen processing by DC among which the main endopeptidases are cathepsins S, L and D (for review, Chapman, 2006). Using the MEROPS on-line data base (merops@ebi.ac.uk, Rawlings Nucleic Acids Res 2016 ref), we designed our linker sequences so that they could presumably be cut by at least one of these three cathepsins.

Separating Overlapping Epitopes Increases DC Presentation

The first situation that we wanted to explore was the case of an overlap between a class II epitope and a class I epitope i.e. where the processing of the class II epitope should result in the destruction of the class I epitope. In our MELOE-1 antigen, this is precisely the case between the DRB01*11-restricted epitope CPPWHPSERISSTL (SEQ ID NO:26) and the HLA-A*0201-restricted TLNDECWPA (SEQ ID NO:31) (FIG. 1A). We figured that the competition for processing between the two epitopes could possibly be alleviated by separating these two epitopes in a synthetic long peptide. We designed two such SLP (31aa) where the two epitopes where linked either with a control GGGG linker (SEQ ID NO:160) or with a potential cathepsin-sensitive linker LVGS (SEQ ID NO:161) (SLP control: AACPPWHPSERISSTLGGGGTLNDECWPASL (SEQ ID NO:171).

We then assessed the efficiency of DC processing and presentation of these SLP at various concentrations by measuring the dose-dependent activation of a DRB01*11-restricted specific T cell clone through classical presentation (FIG. 2A) and the dose-dependent activation of a CD8 HLA-A*0201-restricted specific T cell clone (FIG. 2B) through cross-presentation. This was compared to DC loaded with either full length MELOE-1 (46 aa) or a 31 aa-long peptide that contains the native overlapping epitopes (data not shown).

Figure 2A:
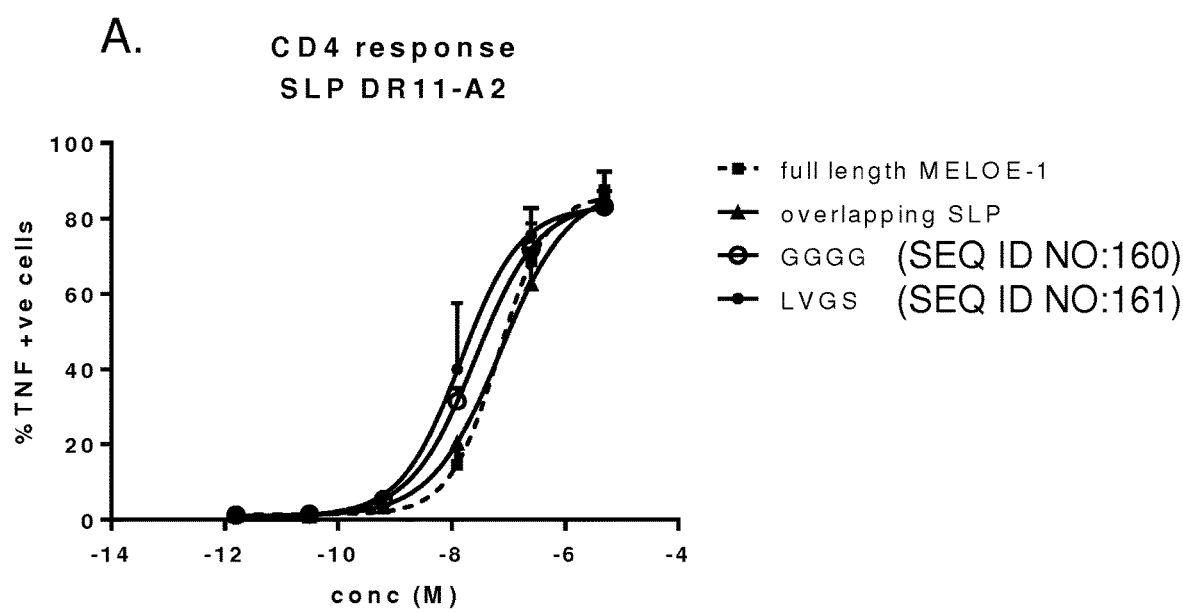

For the presentation of the DRB01*11-restricted epitope, there was no difference of efficacy between the full length MELOE-1 and the 31aa-long native long peptide (EC50 around $7\times10^{-8}$M for both). The presentation was improved when the two epitopes were separated by the GGGG linker (SEQ ID NO:160) (EC50=$2.6\times10^{-8}$M) and further improved with the LVGS linker (SEQ ID NO:161) ($1.4\times10^{-8}$M) (FIG. 2A).

Figure 2B:
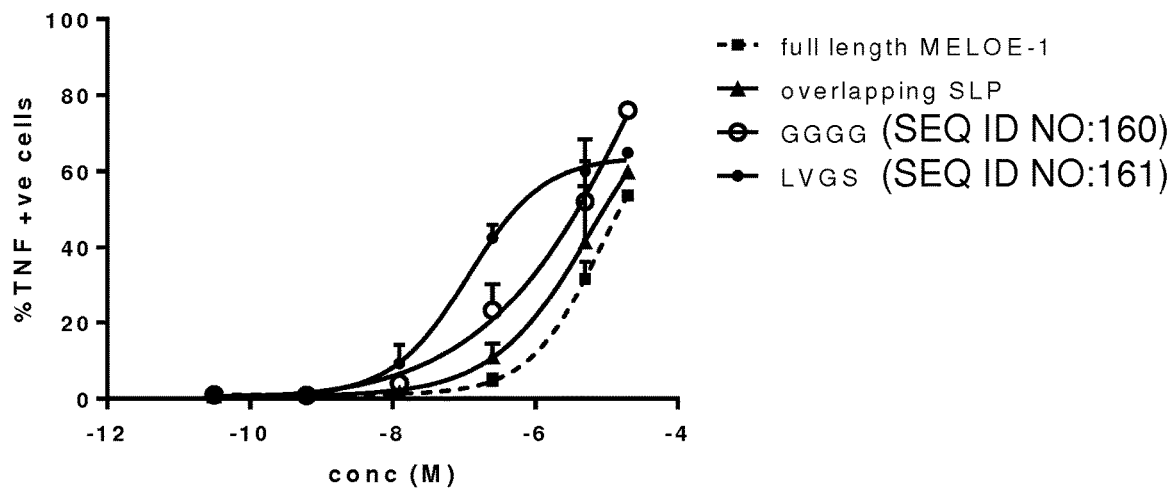

For the cross-presentation of the HLA-A0201-epitope, differences between SLP were more striking. In fact, full length MELOE-1 and the natural long peptide did not differ significantly in terms of cross-presentation ($7.9\times10^{-6}$M vs $5.9\times106$M respectively) while separating the two epitopes with the GGGG linker (SEQ ID NO:160) improved cross presentation ($1.9\times10^{-6}$M). The linker LVGS (SEQ ID NO:161), designed as a target for cathepsins, markedly improved cross-presentation ($1.1\times10^{-7}$M) (FIG. 2B). This observation prompted us to test a variety of linkers for their ability to favor cross-presentation.

Strong Influence of the Linker on Cross Presentation of the HLA Class I Epitope

To assess the influence of the linker sequence on cross-presentation, we designed another serie of SLP containing the previously described DRB1*0101-restricted epitope MELOE-1$_{11-23}$ (SEQ ID NO:24) linked to the HLA-A*0201-restricted MELOE-1 epitope. The choice of a DRB1*0101-restricted epitope was motivated by the fact that this HLA haplotype is frequent in the population and DRB1*0101 transgenic mice are available for in vivo studies. As presented in FIG. 3, we first focused on cross-presentation and observed major differences in the presentation of the HLA-A*0201-restricted MELOE-1 epitope depending on the linker used. In three independent experiments, using full length MELOE-1 as reference (EC50=$2.5\times10^{-7}$M), we observed that some linkers induced poorer cross-presentation (GGGG (SEQ ID NO:160), $1.2\times10^{-6}$M and GSGS (SEQ ID NO:162), $4.3\times10^{-7}$M), ten fold better presentation (ASLG (SEQ ID NO:163), $1.2\times10^{-8}$M and the previously tested LVGS (SEQ ID NO:161), $3.4\times10^{-8}$M) or hundred fold better (PIVLG (SEQ ID NO:164), $3.2\times10^{-9}$M; LLSV (SEQ ID NO:4), $2.8\times10^{-9}$ M; VLSVG (SEQ ID NO:10), $2.1\times10^{-9}$ M) (SLP control: AATSREQFLPSEGAACPPWGGGGTLNDECWPA (SEQ ID NO:172)).

In the next serie of experiments, we designed SLP with a newly identified DRB1*0101-restricted epitope, MELOE-1$_{13-27}$ (SEQ ID NO:21) (FIG. 1A), obtained after in vitro T cell stimulation and cloning from a DRB1*0101 blood donor (data not shown). We wanted to assess the effect of changing the C-terminus of the class II epitope on SLP cross presentation i.e. how it may affect processing at the level of the linker. According to the MEROPS data base, the C-terminus of MELOE-1$_{13-27}$ (PPW, SEQ ID NO: 165) should be less favorable for cutting at the linker level than the C-terminus of MELOE-1$_{11-23}$ (AAC, SEQ ID NO:166). Indeed, when we tested the two linkers previously identified as the most favorable for cross presentation (LLSV (SEQ ID NO:4) and VLSVG (SEQ ID NO:10)) with this new epitope MELOE-1$_{13-27}$ (SEQ ID NO:21), they were still better than full length MELOE-1 but only ten fold so instead of hundred fold (Table 1). This suggested than the aminoacid sequence contributed by the C terminus of the class II epitope could affect processing efficiency at the linker level. Considering this observation, we decided to lengthen the linker to 6 aa and explored variations in the aa sequence around the LSV (SEQ ID NO:167) core that was favorable for processing. SLP containing the linker LLSVGG (SEQ ID NO:9) was the most efficiently processed and cross-presented in this experiment (SLP control: TSREQFLPSEGAACPPWGGGGTLNDECWPASL (SEQ ID NO:173)). The different SLP designed have a sequence of SEQ ID NO:65 to SEQ ID NO:120).

In the same line of thought, we wanted to check whether the linkers defined as favorable for cross presentation of the HLA-A*0201-restricted MELOE-1 would remain so if we changed the class I epitope. We replace the MELOE-1$_{36-44}$ (SEQ ID NO:31) epitope by the HLA-A*0201-restricted Melan-A$_{A27L}$ epitope (ELAGIGILTV, SEQ ID NO:64), thus changing the aa dowstream of the linker from TLND (SEQ ID NO:169) to ELAG (SEQ ID NO:171) and assessed DC cross presentation to a Melan-A/A*0201 specific T cell clone. The long peptide Melan-A$_{16-40\ A27L}$ that can cross present the HLA-A*0201-restricted Melan-A$_{A27L}$ epitope (SEQ ID NO:64) was used as reference in these experiments. As shown on FIG. 4, this epitope replacement resulted in dramatic changes in terms of linker efficiency to promote cross-presentation. SLP containing the linker LLSV (SEQ ID NO:4) became one of the worst in terms of cross presentation (EC50=2.0×10$^{-5}$M) suggesting that cleavage downstream of the linker was favored and thus destroyed the Melan-A epitope. With an additional G, the linker LLSVG (SEQ ID NO:8) did slightly better (8.1×10$^{-6}$M) but was less efficient than the native Melan-A sequence (2.5×10$^{-6}$M). Finally, with the longer linker LLSVGG (SEQ ID NO:9), very efficient cross presentation was restored (1.5×10$^{-7}$M) suggesting that with this longer sequence, cleavage was favored within the linker (SLP control REQFLPSEGAACPPWGGGGELAGIGILTV (SEQ ID NO:174)).

No Strong Influence of the Linker on CD4 Antigen Presentation

In parallel, SLP containing MELOE-1$_{13-27}$ (SEQ ID NO:21) and MELOE-1$_{36-44}$ (SEQ ID NO:31) with linkers LLSV (SEQ ID NO:4), LLSVG (SEQ ID NO:8) or LLSVGG (SEQ ID NO:9) were tested for presentation to a CD4 MELOE-1$_{13-27}$-specific T cell clone to assess the influence of the linker sequence on HLA class II presentation by DC. MELOE-1$_{11-46}$ native long peptide and SLP with the linker GGGG (SEQ ID NO:160) were used as controls. As shown on FIG. 5, the SLP with linker GGGG (SEQ ID NO:160) was poorly presented in comparison to the native long peptide (EC50: 3.5×10$^{-8}$M vs 8.4×10$^{-9}$M) whereas all the other linkers tested were as efficient (LLSVG (SEQ ID NO:8), 6.8×10$^{-9}$M) or slightly better (LLSV (SEQ ID NO:4), 2.7×10$^{-9}$M) than the native sequence in terms of processing for class II presentation.

T Cell Specific Expansion In Vitro is Increased

Figure 6A:
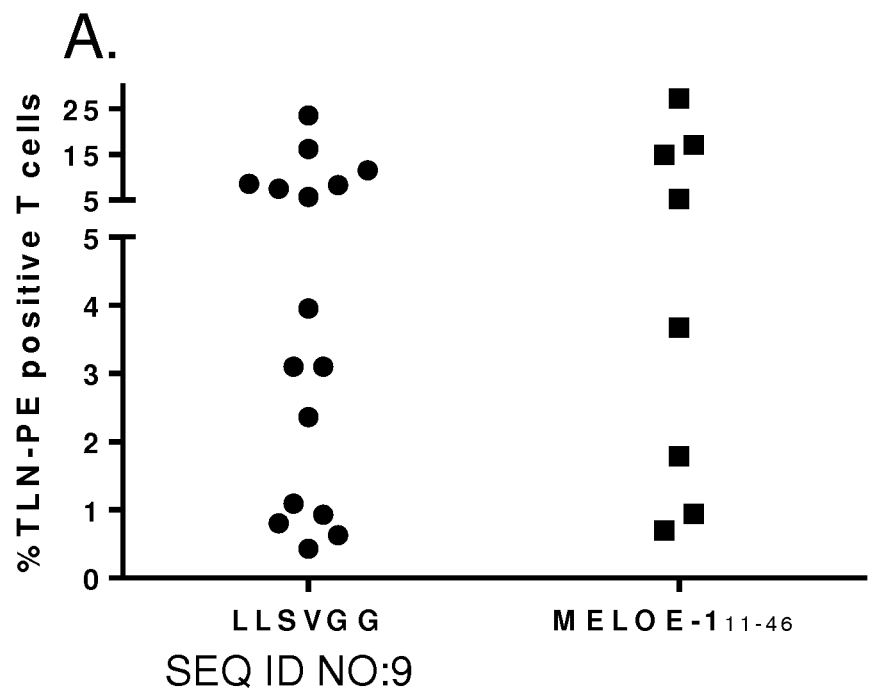
Figure 6B:
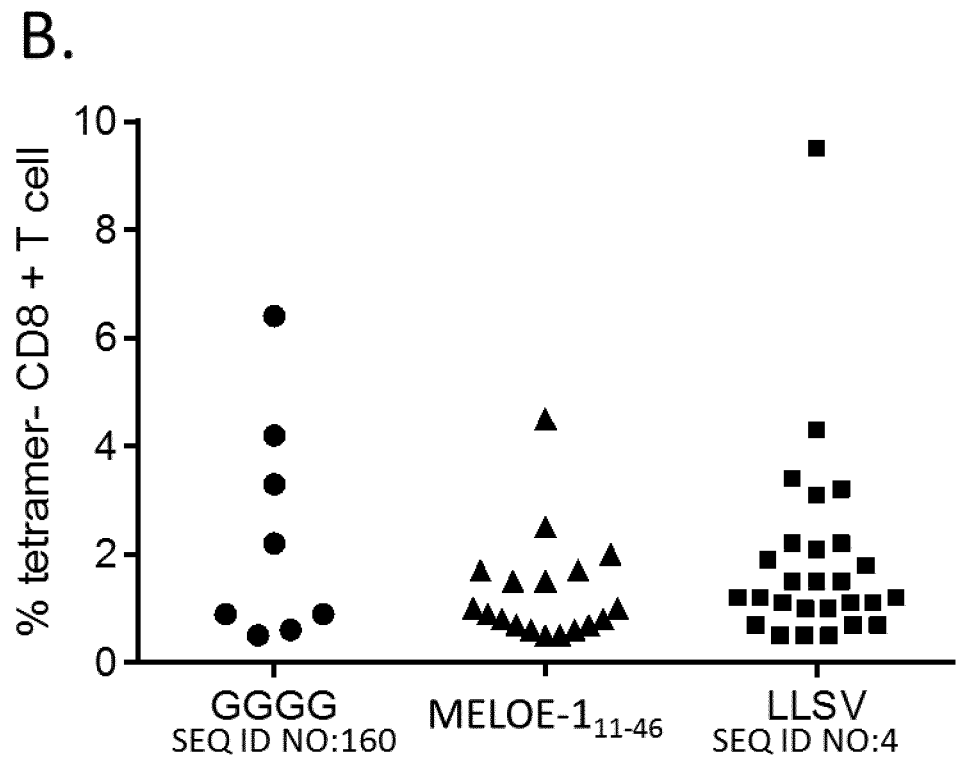
Figure 6C:
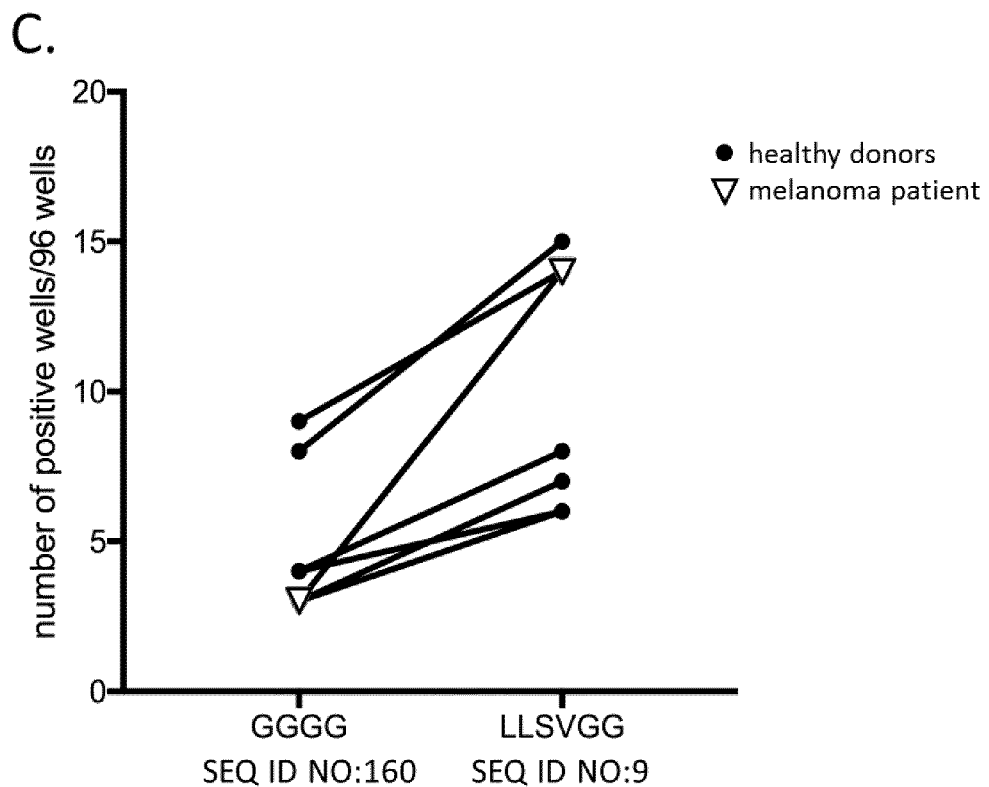
Figure 6D:
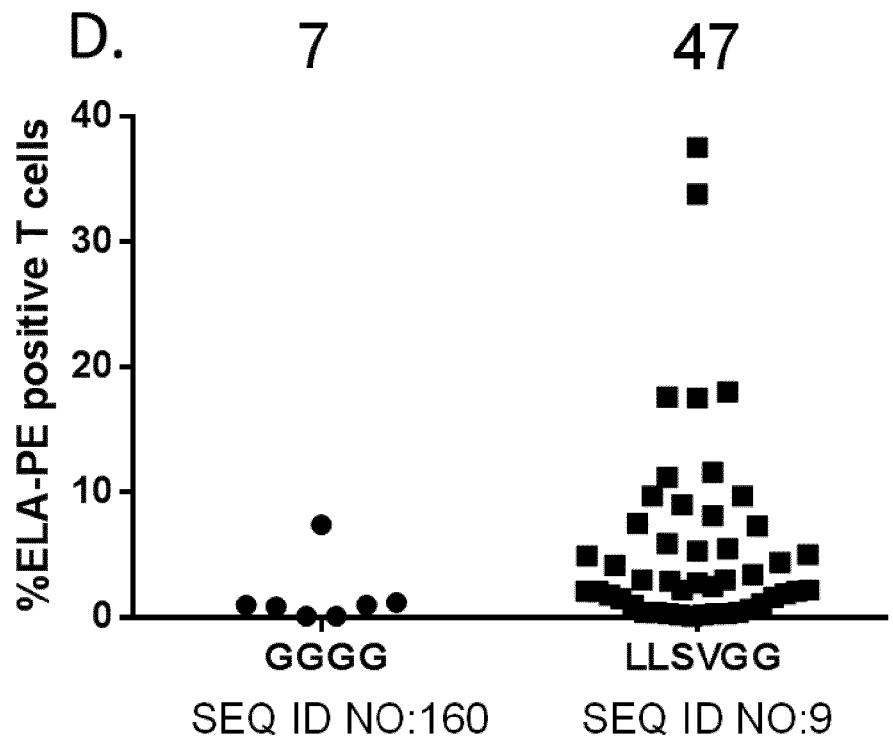

We next tested the ability of SLP containing MELOE-1$_{13-27}$ (SEQ ID NO:21) and MELOE-1$_{36-44}$ (SEQ ID NO:31) with linkers GGGG (SEQ ID NO:160), LLSV (SEQ ID NO:4), or LLSVGG (SEQ ID NO:9) to reactivate and expand CD8 specific T cells within PBMC from HLA-A*0201 healthy donors in vitro. For this purpose, PBMC were treated for 24 h with GMCSF and IL-4 to accelerate the differentiation of monocytes into DC together with SLP at 5 μM and then TNF-a, IL-1b and PGE$_2$ were added as maturation agents as previously described (see M&M). After 21 days, the percentage of CD8 specific T cells in each microculture was assessed by tetramer staining. Results of a typical experiment is presented in FIGS. 6A and 6B showing the number of positive wells (threshold set at 0.5% of tetramer positive CD8 T cells) and the percentages of positive cells following stimulation with either the SLP containing the most efficient linker LLSVGG (SEQ ID NO:9), LLSV (SEQ ID NO:4, the linker GGGG (SEQ ID NO:160) or the native MELOE-1 sequence. Stimulation and in vitro expansion was more efficient with the SLP containing LLSVGG then with the native sequence (16/96 vs 8/96 positive wells, respectively). Stimulation and in vitro expansion of MELOE-1$_{36-44}$-specific T cells with the aSLP containing LLSV was more efficient than with the aSLP containing the GGGG linker (27/96 vs 8/96, p<0.01) and also than the native sequence MELOE-1$_{11-46}$ (27/96 vs 18/96) although not significantly so. The summary of all the experiments performed is presented on table 2. Two donors (HD3 and HD4) displayed few positive microcultures reflecting low frequencies of circulating CD8 MELOE-1 specific cells and thus differences in SLP cross-presentation according to the linker used could not be considered. With the three other healthy donors who showed higher frequencies of T cell responses, the optimal linker LLSV (SEQ ID NO:4) or the latest LLSVGG (SEQ ID NO:9) always increased cross-presentation when compared to either the control linker GGGG (SEQ ID NO:160) or the native sequence. We next assessed our optimal linker LLSVGG using PBMC from seven healthy donors and two melanoma patients. Within this group, one healthy donor and one patient were excluded from the analysis for lack of any T cell response against MELOE-1. With the remaining six donors and one patient, we showed that stimulation with aSLP containing the linker LLSVGG reactivated significantly more specific responses then aSLP containing the linker GGGG (p=0.004, paired t-test) (FIG. 6C). To further confirm this observation, we tested the cross presentation of the SLP containing Melan-A A271. (SEQ ID NO:64) epitope instead of MELOE-1$_{36-44}$ (SEQ ID NO:31) with linkers GGGG (SEQ ID NO:160) or LLSVGG (SEQ ID NO:9). The linker LLSVGG (SEQ ID NO:9) significantly increased in vitro cross-presentation of the Melan-A epitope as compared to GGGG (SEQ ID NO:160) (47/96 vs 7/96 positive wells respectively, p<0.0001) (FIG. 6D).

In Vivo Immunogenicity is Increased

Figure 7C:
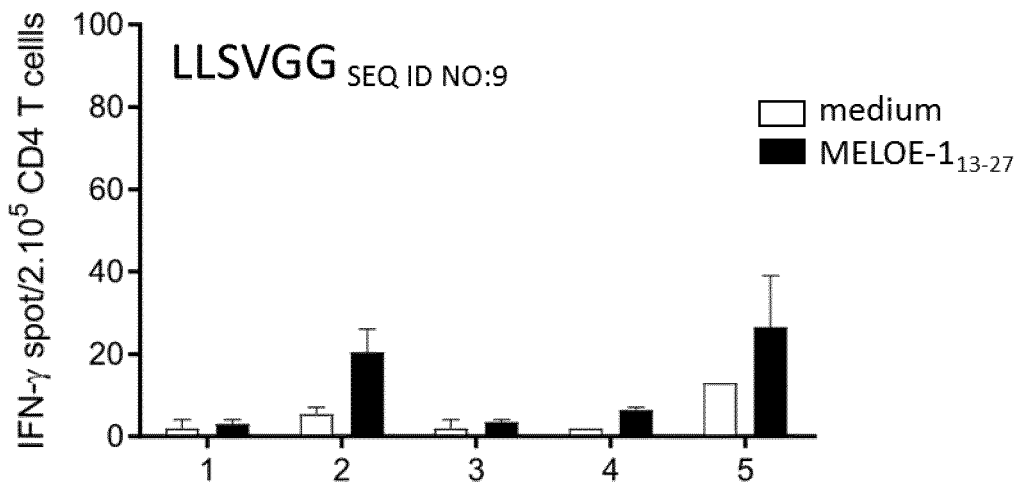

Finally, we explored the immunogenicity of our SLP in vivo in HLA-DRB1*0101/HLA-A*0201 transgenic mice. Mice were immunized subcutaneously with 100 μg of SLP in IFA and poly I:C and boosted at D14 and D28 with 50 μg of SLP with the same adjuvants (see M&M). We focused on cross-presentation and thus assessed CD8 T cell responses by ELISpot-IFN-g after re-stimulation with the short MELOE-11$_{36-44}$ epitope (SEQ ID NO:31) or with medium alone. A mouse was considered responder when ELIspots were above 10 and at least twice about background. A typical experiment is presented in FIG. 7 comparing immunization with SLP containing MELOE-1$_{13-27}$ (SEQ ID NO:21) and MELOE-1$_{36-44}$ (SEQ ID NO:31) with linker GGGG (SEQ ID NO:160) or LLSVGG (SEQ ID NO:9). Immunization with SLP containing GGGG (SEQ ID NO:160) generated moderate CD8 responses in 3 out of five mice while immunization with SLP with LLSVGG (SEQ ID NO:9) was efficient in all 5 mice with two mice showing robust CD8 responses. Previous experiments performed with the shorter linkers LLSV (SEQ ID NO:4) or LLSVG (SEQ ID NO:8) also supported the hypothesis that our synthetic linkers favored cross-presentation when compared to either the linker GGGG or the native sequence (Table 4). In contrast, CD4 responses evaluated ex vivo towards the HLA-DRB1*0101 epitope were very low (FIG. 7C). This suggested that the mouse T cell repertoire against this epitope is scarce as compared to the human T cell repertoire and thus T cell help may not have contributed much to the CD8 responses in those mice.

Antitumor Effect In Vivo Triggered by aSLP Vaccination

Figure 8A:
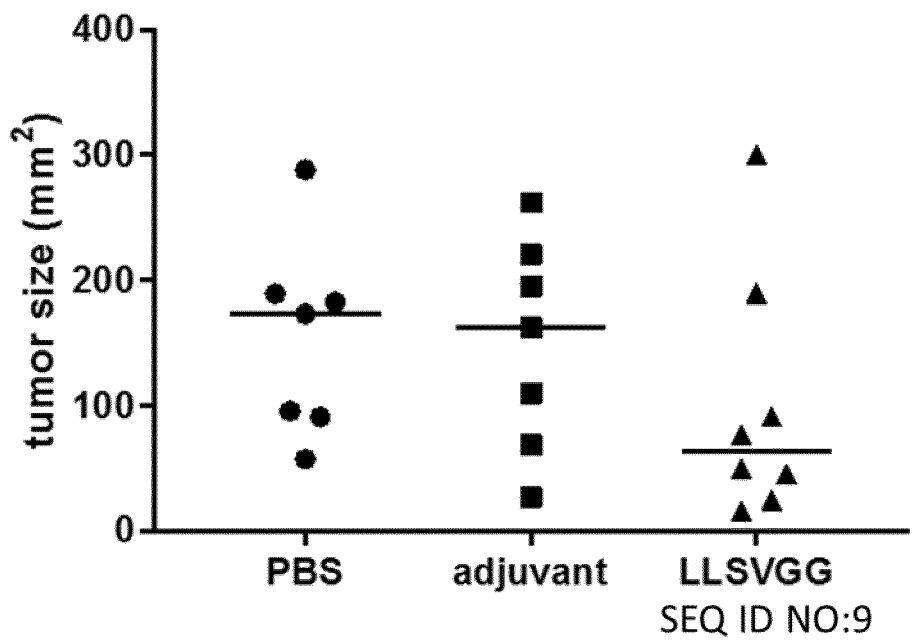
Figure 8B:
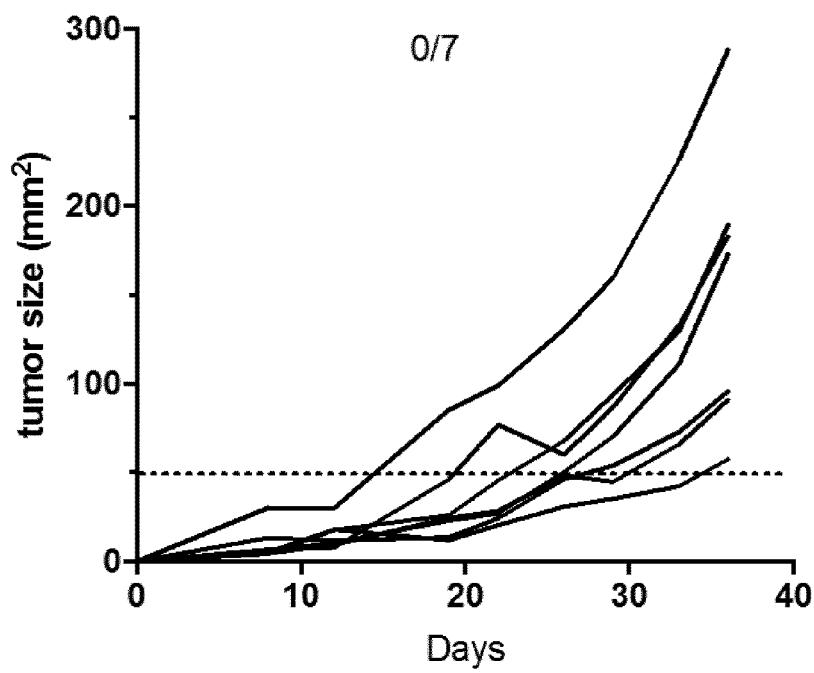
Figure 8C:
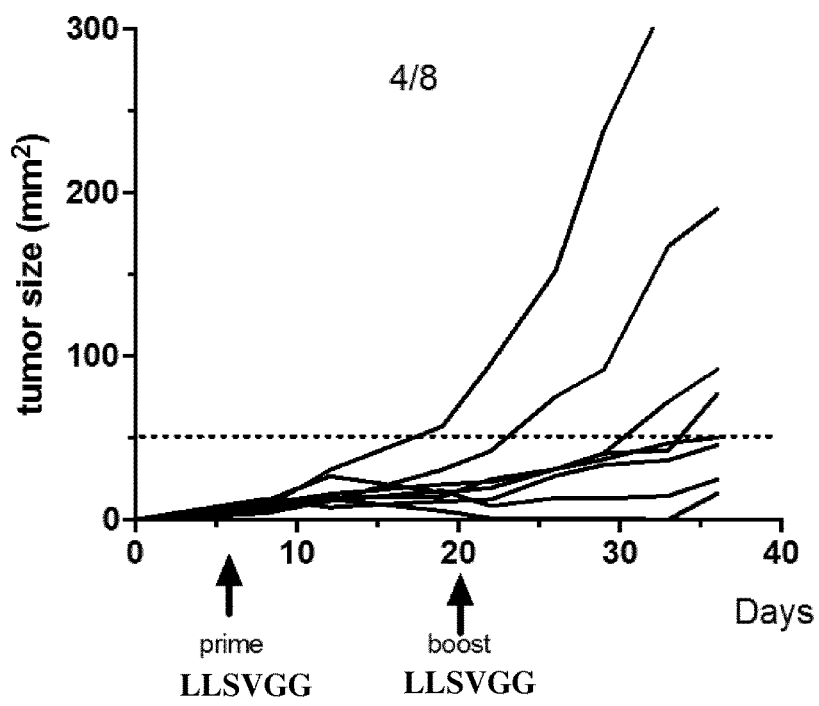

To evaluate the anti-tumor potential of vaccination with aSLP, we used the previously described SARC-A2 cell line transduced with a cDNA encoding the whole MELOE-1 antigen. The ability of this transduced cell line to present the HLAA* 0201-restricted MELOE-1$_{36-44}$ epitope was confirmed in vitro by its ability to stimulate a MELOE-1 specific CD8 T cell clone (data not shown). Following tumor engraftment, mice were vaccinated at day 6 by a prime injection of 100 µg of aSLP with the LLSVGG linker plus adjuvant, or adjuvant alone or PBS, followed by a boost 14 days later. Mice were monitored until the end point at day 36. Comparison of median tumor sizes at endpoint in the three groups of mice is shown in FIG. 8A. At that time, setting the threshold at 50 mm$^2$, all tumors were growing in the seven untreated mice despite variability in tumor size while tumor growth was inhibited in four out of eight mice (0/7 vs 4/8, p=0.0513, Fisher's exact test) (FIGS. 8B and 8C).

CONCLUSION

To determine the optimal linker sequence for cross presentation, we tested a number of linker sequences predicted to be recognized by the endocathepsins present in DC endosomes i.e. mainly cathepsins L, S and D. Our results showed an unexpected wide range in cross-presentation efficiency among them with some aSLP being 100 fold more efficient then the native antigen sequence. In addition, we demonstrated that the aa sequences provided by the class II and class I epitopes upstream and downstream of the linker could critically affect the processing. The most striking example was the abrogation of cross-presentation of the Melan-AA27L epitope when short linkers where used. We thus decided to extend the linker to a 6 aa length to favor cleavage within the linker sequence. A few selected aSLP were then further evaluated for their ability to expand CD8-specific T cells from healthy donors in vitro. It should be pointed out that in those experiments, aSLP were used at high concentrations (5 µM) and persisted in the culture for many days. Therefore, extracellular partial digestion of the aSLP by surface or secreted proteases may have occurred and somewhat blurred differences between the different linkers. Nonetheless, even in those conditions, we confirmed that aSLP containing linkers LLSV and LLSVGG were more efficient than the native MELOE-111-46 or the aSLP with a GGGG linker to expand MELOE-136-44 specific CD8 T lymphocytes. In addition, we confirmed in vivo in transgenic mice that vaccination with aSLP designed with cathepsin-sensitive linkers were the most efficient to trigger CD8+ specific T cell responses. However, our data showed that mouse CD4 T cell responses against the HLA-DRB1*0101-restricted MELOE-1 epitope were weak and thus probably provided little help to the CD8 T cell responses. Such differences in T cell repertoire between those HLA-DRB1*0101/HLA-A*0201 transgenic mice and humans have been previously reported before by some of us: in fact among the four HLA-DRB1*0101-restricted epitopes derived from telomerase reverse transcriptase (hTERT) that are immunogenic in humans (coined UCP 1, 2, 3 and 4), only UCP2 and UCP3 triggered significant CD4 T cell responses and provided help for the CD8 responses in those mice. 13 Thus, we reckon that with our aSLPs in this mouse model, we mainly assessed the linker-dependent efficiency of in vivo cross-presentation of the class I epitope with little influence of the class II epitope. Finally, vaccination with our optimal aSLP inhibited the growth of transplanted SARC-A2 tumors expressing MELOE-1 antigen. Although vaccination inhibited tumor growth in only four out of eight mice, we believe that the vaccination protocol could be further improved in the future. Indeed, in the recent publication of Ott et al. (Ott et al (2017) Nature; 547:217-21) showing impressive clinical results in melanoma patients following vaccination with long peptides, priming consisted in five injections followed by two boosts while we only injected our mice twice. In conclusion, our data provide evidence that (i) designing aSLPs with defined class II and class I epitopes connected by a cathepsin-sensitive linker is a valid approach to allow presentation of both CD4 and CD8 epitopes by DCs and (ii) choosing the optimal linker can significantly enhance cross-presentation to CD8+ T cells and (iii) vaccination with such aSLP can trigger an anti-tumor response in vivo. This approach should now be evaluated in vaccination trials in cancer patients.

REFERENCES

Throughout this application, various references describe the state of the art to which this invention pertains. The disclosures of these references are hereby incorporated by reference into the present disclosure.

1. Melief C J M, van Hall T, Arens R, Ossendorp F, van der Burg S H. Therapeutic cancer vaccines. J Clin Invest 2015; 125:3401-12.
2. Pol J, Bloy N, Buqué A, Eggermont A, Cremer I, Sautès-Fridman C, Galon J, Tartour E, Zitvogel L, Kroemer G, et al. Trial Watch: Peptide-based anticancer vaccines. Oncoimmunology 2015; 4:e974411-3.
3. Bijker M S, van den Eeden S J F, Franken K L, Melief C J M, Offringa R, van der Burg S H. CD8+ CTL priming by exact peptide epitopes in incomplete Freund's adjuvant induces a vanishing CTL response, whereas long peptides induce sustained CTL reactivity. J Immunol 2007; 179: 5033-40.
4. Rosalia R A, Quakkelaar E D, Redeker A, Khan S, Camps M, Drijfhout J W, Silva A L, Jiskoot W, van Hall T, van Veelen P A, et al. Dendritic cells process synthetic long peptides better than whole protein, improving antigen presentation and T-cell activation. Eur J Immunol 2013; 43:2554-65.
5. Wada H, Isobe M, Kakimi K, Mizote Y, Eikawa S, Sato E, Takigawa N, Kiura K, Tsuji K, Iwatsuki K, et al. Vaccination with NY-ESO-1 overlapping peptides mixed with Picibanil O K-432 and montanide ISA-51 in patients with cancers expressing the NY-ESO-1 antigen. J Immunother 2014; 37:84-92.
6. Kenter G G, Welters M J P, Valentijn A R P M, Lowik M J G, Berends-van der Meer D M A, Vloon A P G, Essahsah F, Fathers L M, Offringa R, Drijfhout J W, et al. Vaccination against HPV-16 oncoproteins for vulvar intraepithelial neoplasia. N Engl J Med 2009; 361:1838-47.
7. Ott P A, Hu Z, Keskin D B, Shukla S A, Sun J, Bozym D J, Zhang W, Luoma A, Giobbie-Hurder A, Peter L, et al. An immunogenic personal neoantigen vaccine for patients with melanoma. Nature 2017; 547:217-21.
8. Masuko K, Wakita D, Togashi Y, Kita T, Kitamura H, Nishimura T. Artificially synthesized helper/killer-hybrid epitope long peptide (H/K-HELP): Preparation and immunological analysis of vaccine efficacy. Immunology Letters 2015; 163:102-12.
9. Daftarian P, Mansour M, Benoit A C, Pohajdak B, Hoskin D W, Brown R G, Kast W M. Eradication of established HPV 16-expressing tumors by a single administration of a vaccine composed of a liposome-encapsulated CTL-T helper fusion peptide in a water-in-oil emulsion. Vaccine 2006; 24:5235-44.
10. Dosset M, Godet Y, Vauchy C, Beziaud L, Lone Y C, Sedlik C, Liard C, Levionnois E, Clerc B, Sandoval F, et al. Universal Cancer Peptide-Based Therapeutic Vaccine Breaks Tolerance against Telomerase and Eradicates Established Tumor. Clinical Cancer Research 2012; 18:6284-95.
11. Godet Y, Moreau-Aubry A, Guilloux Y, Vignard V, Khammari A, Dreno B, Jotereau F, Labarriere N. MELOE-1 is a new antigen overexpressed in melanomas and involved in adoptive T cell transfer efficiency. J Exp Med 2008; 205:2673-82.
12. Bobinet M, Vignard V, Florenceau L, Lang F, Labarriere N, Moreau-Aubry A. Overexpression of Meloe Gene in Melanomas Is Controlled Both by Specific Transcription Factors and Hypomethylation. PLOS ONE 2013; 8:e75421.
13. Carbonnelle D, Vignard V, Sehedic D, Moreau-Aubry A, Florenceau L, Charpentier M, Mikulits W, Labarriere N, Lang F. The Melanoma Antigens MELOE-1 and MELOE-2 Are Translated from a Bona Fide Polycistronic mRNA Containing Functional IRES Sequences. PLOS ONE 2013; 8.
14. Rogel A, Vignard V, Bobinet M, Labarriere N, Lang F. A long peptide from MELOE-1 contains multiple HLA class II T cell epitopes in addition to the HLA-A*0201 epitope: an attractive candidate for melanoma vaccination. Cancer Immunol Immunother 2011; 60:327-37.
15. Bobinet M, Vignard V, Rogel A, Khammari A, Dreno B, Lang F, Labarriere N. MELOE-1 antigen contains multiple HLA class II T cell epitopes recognized by Th1 CD4+ T cells from melanoma patients. PLOS ONE 2012; 7:e51716.
16. Godet Y, Desfrancois J, Vignard V, Schadendorf D, Khammari A, Dreno B, Jotereau F, Labarriere N. Frequent occurrence of high affinity T cells against MELOE-1 makes this antigen an attractive target for melanoma immunotherapy. Eur J Immunol 2010; 40:1786-94.
17. Ohtake J, Ohkuri T, Togashi Y, Kitamura H, Okuno K, Nishimura T.
Identification of novel helper epitope peptides of Survivin cancer-associated antigen applicable to developing helper/killer-hybrid epitope long peptide cancer vaccine. Immunology Letters 2014; 161:20-30.
18. Pajot A, Michel M-L, Fazilleau N, Pancré V, Auriault C, Ojcius D M, Lemonnier F A, Lone Y C. A mouse model of human adaptive immune functions: HLA-A2.1-/HLA-DR1-transgenic H-2 class I-/class II-knockout mice. Eur J Immunol 2004; 34:3060-9.
Serwold, T., Gonzalez, F., Kim, J., Jacob, R. & Shastri, N. ERAAP customizes peptides for MHC class I molecules in the endoplasmic reticulum. Nature 419, 480-483 (2002).
O'Brien, C., Flower, D. R. & Feighery, C. Peptide length significantly influences in vitro affinity for MHC class II molecules. Immunome Res 4, 6-7 (2008).
Rawlings, N. D., Barrett, A. J. & Finn, R. Twenty years of the MEROPSdatabase of proteolytic enzymes, their substrates and inhibitors. Nucleic Acids Res. 44, D343-D350 (2016).
Rangan, L, Galaine J, Boidot R, Hamieh M, Dosset M, Francoual J, Beziaud L,

The invention claimed is:

1. A synthetic long peptide (SLP) comprising a CD4 class II peptide linked to a CD8 class I peptide by a peptidic linker,
   wherein the peptidic linker is selected from the group consisting of the amino acid sequences LLSVG (SEQ ID NO:8), LLSVGG (SEQ ID NO:9) and LLSVGA (SEQ ID NO:191), and
   wherein the CD4 class II peptide is linked at its C-terminal position to the peptidic linker and the CD8 class I peptide is linked at its N-terminal position to the peptidic linker, and
   wherein the CD4 class II peptide and/or the CD8 class I peptide consists of a contiguous amino acid sequence selected from the group consisting of: SEQ ID NO:15 to 64, SEQ ID NO: 121 to 144 and SEQ ID NO:148 to 158.

2. A nucleic acid sequence encoding an SLP according to claim 1.

3. A vaccine composition comprising an SLP according to claim 1.

4. A T lymphocyte that recognizes specifically a SLP according to claim 1.

5. A method for treating cancer, infectious diseases, inflammatory diseases or auto-immune diseases by in a patient in need thereof comprising,
   administering to the patient the SLP according to claim 1 or a nucleic acid encoding the SLP.

6. The method of claim 5, wherein the SLP is administered in a vaccine composition.

7. The method of claim 5, wherein the cancer is melanoma.

8. The SLP of claim 1, wherein the peptidic linker is SEQ ID NO:8.

9. The SLP of claim 1, wherein the peptidic linker is SEQ ID NO:9.

10. The SLP of claim 1, wherein the peptidic linker is SEQ ID NO:191.

11. A synthetic long peptide (SLP) comprising a CD4 class II peptide linked to a CD8 class I peptide by a peptidic linker, wherein the peptidic linker is selected from the group consisting of the amino acid sequences LLSV (SEQ ID NO:4), LLSVG (SEQ ID NO:8) and LLSVGG (SEQ ID NO:9), and wherein the CD4 class II peptide is linked at its C-terminal position to the peptidic linker and the CD8 class I peptide is linked at its N-terminal position to the peptidic linker, and wherein the SLP has an amino acid sequence selected from the group consisting of SEQ ID NO:68, SEQ ID NO:87, SEQ ID NO: 181 and SEQ ID NO: 182.

12. A synthetic long peptide (SLP) comprising a CD4 class II peptide linked to a CD8 class I peptide by a peptidic linker having the amino acid sequence identity of LLSVGG (SEQ ID NO:9), and wherein the CD4 class II peptide is linked at its C-terminal position to the peptidic linker and the CD8 class I peptide is linked at its N-terminal position to the peptidic linker, and wherein the SLP has an amino acid sequence selected from the group consisting of SEQ ID NO:68, SEQ ID NO:87, SEQ ID NO:96, SEQ ID NO: 181 and SEQ ID NO: 182.

* * * * *

SEQUENCE LISTING

```
<160> NUMBER OF SEQ ID NOS: 191

<210> SEQ ID NO 1
<211> LENGTH: 6
<212> TYPE: PRT
<213> ORGANISM: Artificial
<220> FEATURE:
<223> OTHER INFORMATION: Synthetic Linker
<220> FEATURE:
<221> NAME/KEY: MISC_FEATURE
<222> LOCATION: (1)..(1)
<223> OTHER INFORMATION: A, L, V, S or G
<220> FEATURE:
<221> NAME/KEY: MISC_FEATURE
<222> LOCATION: (5)..(6)
<223> OTHER INFORMATION: A, L, V, G or no amino acid

<400> SEQUENCE: 1

Xaa Leu Ser Val Xaa Xaa
1               5

<210> SEQ ID NO 2
<211> LENGTH: 4
<212> TYPE: PRT
<213> ORGANISM: Artificial
<220> FEATURE:
<223> OTHER INFORMATION: Synthetic Linker
<220> FEATURE:
<221> NAME/KEY: MISC_FEATURE
<222> LOCATION: (1)..(1)
<223> OTHER INFORMATION: A, L, V, S or G

<400> SEQUENCE: 2

Xaa Leu Ser Val
1

<210> SEQ ID NO 3
```

```
<211> LENGTH: 5
<212> TYPE: PRT
<213> ORGANISM: Artificial
<220> FEATURE:
<223> OTHER INFORMATION: Synthetic Linker
<220> FEATURE:
<221> NAME/KEY: MISC_FEATURE
<222> LOCATION: (1)..(1)
<223> OTHER INFORMATION: A, L, V, S or G
<220> FEATURE:
<221> NAME/KEY: MISC_FEATURE
<222> LOCATION: (5)..(5)
<223> OTHER INFORMATION: A, L, V or G

<400> SEQUENCE: 3

Xaa Leu Ser Val Xaa
1               5

<210> SEQ ID NO 4
<211> LENGTH: 4
<212> TYPE: PRT
<213> ORGANISM: Artificial
<220> FEATURE:
<223> OTHER INFORMATION: Synthetic Linker

<400> SEQUENCE: 4

Leu Leu Ser Val
1

<210> SEQ ID NO 5
<211> LENGTH: 4
<212> TYPE: PRT
<213> ORGANISM: Artificial
<220> FEATURE:
<223> OTHER INFORMATION: Synthetic Linker

<400> SEQUENCE: 5

Val Leu Ser Val
1

<210> SEQ ID NO 6
<211> LENGTH: 4
<212> TYPE: PRT
<213> ORGANISM: Artificial
<220> FEATURE:
<223> OTHER INFORMATION: Synthetic Linker

<400> SEQUENCE: 6

Ser Leu Ser Val
1

<210> SEQ ID NO 7
<211> LENGTH: 4
<212> TYPE: PRT
<213> ORGANISM: Artificial
<220> FEATURE:
<223> OTHER INFORMATION: Synthetic Linker

<400> SEQUENCE: 7

Gly Leu Ser Val
1

<210> SEQ ID NO 8
<211> LENGTH: 5
<212> TYPE: PRT
<213> ORGANISM: Artificial
<220> FEATURE:
<223> OTHER INFORMATION: Synthetic Linker
```

```
<400> SEQUENCE: 8

Leu Leu Ser Val Gly
1               5

<210> SEQ ID NO 9
<211> LENGTH: 6
<212> TYPE: PRT
<213> ORGANISM: Artificial
<220> FEATURE:
<223> OTHER INFORMATION: Synthetic Linker

<400> SEQUENCE: 9

Leu Leu Ser Val Gly Gly
1               5

<210> SEQ ID NO 10
<211> LENGTH: 5
<212> TYPE: PRT
<213> ORGANISM: Artificial
<220> FEATURE:
<223> OTHER INFORMATION: Synthetic Linker

<400> SEQUENCE: 10

Val Leu Ser Val Gly
1               5

<210> SEQ ID NO 11
<211> LENGTH: 6
<212> TYPE: PRT
<213> ORGANISM: Artificial
<220> FEATURE:
<223> OTHER INFORMATION: Synthetic Linker

<400> SEQUENCE: 11

Val Leu Ser Val Gly Gly
1               5

<210> SEQ ID NO 12
<211> LENGTH: 46
<212> TYPE: PRT
<213> ORGANISM: Artificial
<220> FEATURE:
<223> OTHER INFORMATION: Synthetic Meloe-1

<400> SEQUENCE: 12

Met Ser Cys Val Gly Tyr Pro Asp Glu Ala Thr Ser Arg Glu Gln Phe
1               5                   10                  15

Leu Pro Ser Glu Gly Ala Ala Cys Pro Pro Trp His Pro Ser Glu Arg
            20                  25                  30

Ile Ser Ser Thr Leu Asn Asp Glu Cys Trp Pro Ala Ser Leu
        35                  40                  45

<210> SEQ ID NO 13
<211> LENGTH: 39
<212> TYPE: PRT
<213> ORGANISM: Artificial
<220> FEATURE:
<223> OTHER INFORMATION: Synthetic Meloe-2

<400> SEQUENCE: 13

Met Ser Glu Asn Ala Gly Gly Ala Val Ala Arg Thr Ala Thr Ala Phe
1               5                   10                  15

Cys Ala Leu Val Ser Pro Thr Pro Gln Pro Arg Cys Pro Pro Lys Pro
            20                  25                  30
```

Pro Leu Ala Ala Leu Cys Gln
        35

<210> SEQ ID NO 14
<211> LENGTH: 118
<212> TYPE: PRT
<213> ORGANISM: Artificial
<220> FEATURE:
<223> OTHER INFORMATION: Synthetic Melan-A

<400> SEQUENCE: 14

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 15
<211> LENGTH: 10
<212> TYPE: PRT
<213> ORGANISM: Artificial
<220> FEATURE:
<223> OTHER INFORMATION: Synthetic Melan-A peptides general formula
<220> FEATURE:
<221> NAME/KEY: MISC_FEATURE
<222> LOCATION: (2)..(2)
<223> OTHER INFORMATION: L, A, M, V, I or Q

<400> SEQUENCE: 15

Glu Xaa Ala Gly Ile Gly Ile Leu Thr Val
1               5                   10

<210> SEQ ID NO 16
<211> LENGTH: 9
<212> TYPE: PRT
<213> ORGANISM: Artificial
<220> FEATURE:
<223> OTHER INFORMATION: Synthetic Meloe-1 peptides general formula
<220> FEATURE:
<221> NAME/KEY: MISC_FEATURE
<222> LOCATION: (2)..(2)
<223> OTHER INFORMATION: L, M, V, I or Q
<220> FEATURE:
<221> NAME/KEY: MISC_FEATURE
<222> LOCATION: (9)..(9)
<223> OTHER INFORMATION: A, V or L

<400> SEQUENCE: 16

Thr Xaa Asn Asp Glu Cys Trp Pro Xaa
1               5

<210> SEQ ID NO 17
<211> LENGTH: 9
<212> TYPE: PRT

<213> ORGANISM: Artificial
<220> FEATURE:
<223> OTHER INFORMATION: Synthetic Meloe-2 peptides general formula
<220> FEATURE:
<221> NAME/KEY: MISC_FEATURE
<222> LOCATION: (2)..(2)
<223> OTHER INFORMATION: C, L, M, V, I or Q
<220> FEATURE:
<221> NAME/KEY: MISC_FEATURE
<222> LOCATION: (9)..(9)
<223> OTHER INFORMATION: A, V or L

<400> SEQUENCE: 17

Arg Xaa Pro Pro Lys Pro Pro Leu Xaa
1               5

<210> SEQ ID NO 18
<211> LENGTH: 13
<212> TYPE: PRT
<213> ORGANISM: Artificial
<220> FEATURE:
<223> OTHER INFORMATION: Synthetic Meloe-1 CD4 class II peptide

<400> SEQUENCE: 18

Arg Ile Ser Ser Thr Leu Asn Asp Glu Cys Trp Pro Ala
1               5                   10

<210> SEQ ID NO 19
<211> LENGTH: 14
<212> TYPE: PRT
<213> ORGANISM: Artificial
<220> FEATURE:
<223> OTHER INFORMATION: Synthetic Meloe-1 CD4 class II peptide

<400> SEQUENCE: 19

Glu Arg Ile Ser Ser Thr Leu Asn Asp Glu Cys Trp Pro Ala
1               5                   10

<210> SEQ ID NO 20
<211> LENGTH: 11
<212> TYPE: PRT
<213> ORGANISM: Artificial
<220> FEATURE:
<223> OTHER INFORMATION: Synthetic Meloe-1 CD4 class II peptide

<400> SEQUENCE: 20

Pro Asp Glu Ala Thr Ser Arg Glu Gln Phe Leu
1               5                   10

<210> SEQ ID NO 21
<211> LENGTH: 15
<212> TYPE: PRT
<213> ORGANISM: Artificial
<220> FEATURE:
<223> OTHER INFORMATION: Synthetic Meloe-1 CD4 class II peptide

<400> SEQUENCE: 21

Arg Glu Gln Phe Leu Pro Ser Glu Gly Ala Ala Cys Pro Pro Trp
1               5                   10                  15

<210> SEQ ID NO 22
<211> LENGTH: 14
<212> TYPE: PRT
<213> ORGANISM: Artificial
<220> FEATURE:
<223> OTHER INFORMATION: Synthetic Meloe-1 CD4 class II peptide

<400> SEQUENCE: 22

```
Glu Gln Phe Leu Pro Ser Glu Gly Ala Ala Cys Pro Pro Trp
1               5                   10
```

<210> SEQ ID NO 23
<211> LENGTH: 13
<212> TYPE: PRT
<213> ORGANISM: Artificial
<220> FEATURE:
<223> OTHER INFORMATION: Synthetic Meloe-1 CD4 class II peptide

<400> SEQUENCE: 23

```
Gln Phe Leu Pro Ser Glu Gly Ala Ala Cys Pro Pro Trp
1               5                   10
```

<210> SEQ ID NO 24
<211> LENGTH: 13
<212> TYPE: PRT
<213> ORGANISM: Artificial
<220> FEATURE:
<223> OTHER INFORMATION: Synthetic Meloe-1 CD4 class II peptide

<400> SEQUENCE: 24

```
Thr Ser Arg Glu Gln Phe Leu Pro Ser Glu Gly Ala Ala
1               5                   10
```

<210> SEQ ID NO 25
<211> LENGTH: 13
<212> TYPE: PRT
<213> ORGANISM: Artificial
<220> FEATURE:
<223> OTHER INFORMATION: Synthetic Meloe-1 CD4 class II peptide

<400> SEQUENCE: 25

```
Ser Arg Glu Gln Phe Leu Pro Ser Glu Gly Ala Ala Cys
1               5                   10
```

<210> SEQ ID NO 26
<211> LENGTH: 14
<212> TYPE: PRT
<213> ORGANISM: Artificial
<220> FEATURE:
<223> OTHER INFORMATION: Synthetic Meloe-1 CD4 class II peptide

<400> SEQUENCE: 26

```
Cys Pro Pro Trp His Pro Ser Glu Arg Ile Ser Ser Thr Leu
1               5                   10
```

<210> SEQ ID NO 27
<211> LENGTH: 13
<212> TYPE: PRT
<213> ORGANISM: Artificial
<220> FEATURE:
<223> OTHER INFORMATION: Synthetic Meloe-1 CD4 class II peptide

<400> SEQUENCE: 27

```
Cys Pro Pro Trp His Pro Ser Glu Arg Ile Ser Ser Thr
1               5                   10
```

<210> SEQ ID NO 28
<211> LENGTH: 12
<212> TYPE: PRT
<213> ORGANISM: Artificial
<220> FEATURE:
<223> OTHER INFORMATION: Synthetic Melan-A CD4 class II peptide

<400> SEQUENCE: 28

```
Glu Glu Leu Ala Gly Ile Gly Ile Leu Thr Val Ile
```

```
<210> SEQ ID NO 29
<211> LENGTH: 15
<212> TYPE: PRT
<213> ORGANISM: Artificial
<220> FEATURE:
<223> OTHER INFORMATION: Synthetic Melan-A CD4 class II peptide

<400> SEQUENCE: 29

Glu Leu Ala Gly Ile Gly Ile Leu Thr Val Ile Leu Gly Val Leu
1               5                   10                  15

<210> SEQ ID NO 30
<211> LENGTH: 20
<212> TYPE: PRT
<213> ORGANISM: Artificial
<220> FEATURE:
<223> OTHER INFORMATION: Synthetic Melan-A CD4 class II peptide

<400> SEQUENCE: 30

Met Pro Arg Glu Asp Ala His Phe Ile Tyr Gly Tyr Pro Lys Lys Gly
1               5                   10                  15

His Gly His Ser
            20

<210> SEQ ID NO 31
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 31

Thr Leu Asn Asp Glu Cys Trp Pro Ala
1               5

<210> SEQ ID NO 32
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 32

Thr Met Asn Asp Glu Cys Trp Pro Ala
1               5

<210> SEQ ID NO 33
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 33

Thr Val Asn Asp Glu Cys Trp Pro Ala
1               5

<210> SEQ ID NO 34
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 34
```

Thr Ile Asn Asp Glu Cys Trp Pro Ala
1               5

<210> SEQ ID NO 35
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 35

Thr Gln Asn Asp Glu Cys Trp Pro Ala
1               5

<210> SEQ ID NO 36
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 36

Thr Leu Asn Asp Glu Cys Trp Pro Val
1               5

<210> SEQ ID NO 37
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 37

Thr Met Asn Asp Glu Cys Trp Pro Val
1               5

<210> SEQ ID NO 38
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 38

Thr Val Asn Asp Glu Cys Trp Pro Val
1               5

<210> SEQ ID NO 39
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 39

Thr Ile Asn Asp Glu Cys Trp Pro Val
1               5

<210> SEQ ID NO 40
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 40

Thr Gln Asn Asp Glu Cys Trp Pro Val
1               5

<210> SEQ ID NO 41
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 41

Thr Leu Asn Asp Glu Cys Trp Pro Leu
1               5

<210> SEQ ID NO 42
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 42

Thr Met Asn Asp Glu Cys Trp Pro Leu
1               5

<210> SEQ ID NO 43
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 43

Thr Val Asn Asp Glu Cys Trp Pro Leu
1               5

<210> SEQ ID NO 44
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 44

Thr Ile Asn Asp Glu Cys Trp Pro Leu
1               5

<210> SEQ ID NO 45
<211> LENGTH: 9
<212> TYPE: PRT
<213> ORGANISM: Artificial
<220> FEATURE:
<223> OTHER INFORMATION: Synthetic Meloe-1 CD8 class I peptide

<400> SEQUENCE: 45

Thr Gln Asn Asp Glu Cys Trp Pro Leu
1               5

<210> SEQ ID NO 46
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 46

Arg Cys Pro Pro Lys Pro Pro Leu Ala

-continued

```
1               5

<210> SEQ ID NO 47
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 47

Arg Leu Pro Pro Lys Pro Pro Leu Ala
1               5

<210> SEQ ID NO 48
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 48

Arg Met Pro Pro Lys Pro Pro Leu Ala
1               5

<210> SEQ ID NO 49
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 49

Arg Val Pro Pro Lys Pro Pro Leu Ala
1               5

<210> SEQ ID NO 50
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 50

Arg Ile Pro Pro Lys Pro Pro Leu Ala
1               5

<210> SEQ ID NO 51
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 51

Arg Gln Pro Pro Lys Pro Pro Leu Ala
1               5

<210> SEQ ID NO 52
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 52

Arg Cys Pro Pro Lys Pro Pro Leu Val
1               5
```

```
<210> SEQ ID NO 53
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 53

Arg Leu Pro Pro Lys Pro Pro Leu Val
1               5

<210> SEQ ID NO 54
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 54

Arg Met Pro Pro Lys Pro Pro Leu Val
1               5

<210> SEQ ID NO 55
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 55

Arg Val Pro Pro Lys Pro Pro Leu Val
1               5

<210> SEQ ID NO 56
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 56

Arg Ile Pro Pro Lys Pro Pro Leu Val
1               5

<210> SEQ ID NO 57
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 57

Arg Gln Pro Pro Lys Pro Pro Leu Val
1               5

<210> SEQ ID NO 58
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 58

Arg Cys Pro Pro Lys Pro Pro Leu Leu
1               5
```

<210> SEQ ID NO 59
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 59

Arg Leu Pro Pro Lys Pro Pro Leu Leu
1               5

<210> SEQ ID NO 60
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 60

Arg Met Pro Pro Lys Pro Pro Leu Leu
1               5

<210> SEQ ID NO 61
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 61

Arg Val Pro Pro Lys Pro Pro Leu Leu
1               5

<210> SEQ ID NO 62
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 62

Arg Ile Pro Pro Lys Pro Pro Leu Leu
1               5

<210> SEQ ID NO 63
<211> LENGTH: 9
<212> TYPE: PRT
<213> ORGANISM: Artificial
<220> FEATURE:
<223> OTHER INFORMATION: Synthetic Meloe-2 CD8 class I peptide

<400> SEQUENCE: 63

Arg Gln Pro Pro Lys Pro Pro Leu Leu
1               5

<210> SEQ ID NO 64
<211> LENGTH: 10
<212> TYPE: PRT
<213> ORGANISM: Artificial
<220> FEATURE:
<223> OTHER INFORMATION: Synthetic Melan-A CD8 class I peptide

<400> SEQUENCE: 64

Glu Leu Ala Gly Ile Gly Ile Leu Thr Val
1               5                   10

```
<210> SEQ ID NO 65
<211> LENGTH: 32
<212> TYPE: PRT
<213> ORGANISM: Artificial
<220> FEATURE:
<223> OTHER INFORMATION: Synthetic SLP

<400> SEQUENCE: 65

Thr Ser Arg Glu Gln Phe Leu Pro Ser Glu Gly Ala Ala Cys Pro Pro
1               5                   10                  15

Trp Leu Leu Ser Val Thr Leu Asn Asp Glu Cys Trp Pro Ala Ser Leu
            20                  25                  30

<210> SEQ ID NO 66
<211> LENGTH: 27
<212> TYPE: PRT
<213> ORGANISM: Artificial
<220> FEATURE:
<223> OTHER INFORMATION: Synthetic SLP

<400> SEQUENCE: 66

Arg Glu Gln Phe Leu Pro Ser Glu Gly Ala Ala Cys Pro Pro Trp Leu
1               5                   10                  15

Leu Ser Val Thr Leu Asn Asp Glu Cys Trp Pro
            20                  25

<210> SEQ ID NO 67
<211> LENGTH: 30
<212> TYPE: PRT
<213> ORGANISM: Artificial
<220> FEATURE:
<223> OTHER INFORMATION: Synthetic SLP

<400> SEQUENCE: 67

Arg Glu Gln Phe Leu Pro Ser Glu Gly Ala Ala Cys Pro Pro Trp Val
1               5                   10                  15

Leu Ser Val Gly Gly Thr Leu Asn Asp Glu Cys Trp Pro Ala
            20                  25                  30

<210> SEQ ID NO 68
<211> LENGTH: 30
<212> TYPE: PRT
<213> ORGANISM: Artificial
<220> FEATURE:
<223> OTHER INFORMATION: Synthetic SLP

<400> SEQUENCE: 68

Arg Glu Gln Phe Leu Pro Ser Glu Gly Ala Ala Cys Pro Pro Trp Leu
1               5                   10                  15

Leu Ser Val Gly Gly Thr Leu Asn Asp Glu Cys Trp Pro Ala
            20                  25                  30

<210> SEQ ID NO 69
<211> LENGTH: 34
<212> TYPE: PRT
<213> ORGANISM: Artificial
<220> FEATURE:
<223> OTHER INFORMATION: Synthetic SLP

<400> SEQUENCE: 69

Thr Ser Arg Glu Gln Phe Leu Pro Ser Glu Gly Ala Ala Cys Pro Pro
1               5                   10                  15

Trp Val Leu Ser Val Gly Gly Thr Leu Asn Asp Glu Cys Trp Pro Ala
            20                  25                  30
```

Ser Leu

<210> SEQ ID NO 70
<211> LENGTH: 30
<212> TYPE: PRT
<213> ORGANISM: Artificial
<220> FEATURE:
<223> OTHER INFORMATION: Synthetic SLP

<400> SEQUENCE: 70

Arg Glu Gln Phe Leu Pro Ser Glu Gly Ala Ala Cys Pro Pro Trp Val
1               5                   10                  15

Leu Ser Val Gly Ala Thr Leu Asn Asp Glu Cys Trp Pro Ala
            20                  25                  30

<210> SEQ ID NO 71
<211> LENGTH: 33
<212> TYPE: PRT
<213> ORGANISM: Artificial
<220> FEATURE:
<223> OTHER INFORMATION: Synthetic SLP

<400> SEQUENCE: 71

Thr Ser Arg Glu Gln Phe Leu Pro Ser Glu Gly Ala Ala Cys Pro Pro
1               5                   10                  15

Trp Val Leu Ser Val Gly Thr Leu Asn Asp Glu Cys Trp Pro Ala Ser
            20                  25                  30

Leu

<210> SEQ ID NO 72
<211> LENGTH: 29
<212> TYPE: PRT
<213> ORGANISM: Artificial
<220> FEATURE:
<223> OTHER INFORMATION: Synthetic SLP

<400> SEQUENCE: 72

Arg Glu Gln Phe Leu Pro Ser Glu Gly Ala Ala Cys Pro Pro Trp Val
1               5                   10                  15

Leu Ser Val Gly Thr Leu Asn Asp Glu Cys Trp Pro Ala
            20                  25

<210> SEQ ID NO 73
<211> LENGTH: 34
<212> TYPE: PRT
<213> ORGANISM: Artificial
<220> FEATURE:
<223> OTHER INFORMATION: Synthetic SLP

<400> SEQUENCE: 73

Thr Ser Arg Glu Gln Phe Leu Pro Ser Glu Gly Ala Ala Cys Pro Pro
1               5                   10                  15

Trp Ser Leu Ser Val Ala Ala Thr Leu Asn Asp Glu Cys Trp Pro Ala
            20                  25                  30

Ser Leu

<210> SEQ ID NO 74
<211> LENGTH: 30
<212> TYPE: PRT
<213> ORGANISM: Artificial
<220> FEATURE:
<223> OTHER INFORMATION: Synthetic SLP

<400> SEQUENCE: 74

-continued

Arg Glu Gln Phe Leu Pro Ser Glu Gly Ala Ala Cys Pro Pro Trp Ser
1               5                   10                  15

Leu Ser Val Ala Ala Thr Leu Asn Asp Glu Cys Trp Pro Ala
            20                  25                  30

<210> SEQ ID NO 75
<211> LENGTH: 34
<212> TYPE: PRT
<213> ORGANISM: Artificial
<220> FEATURE:
<223> OTHER INFORMATION: Synthetic SLP

<400> SEQUENCE: 75

Thr Ser Arg Glu Gln Phe Leu Pro Ser Glu Gly Ala Ala Cys Pro Pro
1               5                   10                  15

Trp Ser Leu Ser Val Gly Gly Thr Leu Asn Asp Glu Cys Trp Pro Ala
            20                  25                  30

Ser Leu

<210> SEQ ID NO 76
<211> LENGTH: 30
<212> TYPE: PRT
<213> ORGANISM: Artificial
<220> FEATURE:
<223> OTHER INFORMATION: Synthetic SLP

<400> SEQUENCE: 76

Arg Glu Gln Phe Leu Pro Ser Glu Gly Ala Ala Cys Pro Pro Trp Ser
1               5                   10                  15

Leu Ser Val Gly Gly Thr Leu Asn Asp Glu Cys Trp Pro Ala
            20                  25                  30

<210> SEQ ID NO 77
<211> LENGTH: 34
<212> TYPE: PRT
<213> ORGANISM: Artificial
<220> FEATURE:
<223> OTHER INFORMATION: Synthetic SLP

<400> SEQUENCE: 77

Thr Ser Arg Glu Gln Phe Leu Pro Ser Glu Gly Ala Ala Cys Pro Pro
1               5                   10                  15

Trp Ala Leu Ser Val Gly Gly Thr Leu Asn Asp Glu Cys Trp Pro Ala
            20                  25                  30

Ser Leu

<210> SEQ ID NO 78
<211> LENGTH: 30
<212> TYPE: PRT
<213> ORGANISM: Artificial
<220> FEATURE:
<223> OTHER INFORMATION: Synthetic SLP

<400> SEQUENCE: 78

Arg Glu Gln Phe Leu Pro Ser Glu Gly Ala Ala Cys Pro Pro Trp Ala
1               5                   10                  15

Leu Ser Val Gly Gly Thr Leu Asn Asp Glu Cys Trp Pro Ala
            20                  25                  30

<210> SEQ ID NO 79
<211> LENGTH: 34
<212> TYPE: PRT

```
<213> ORGANISM: Artificial
<220> FEATURE:
<223> OTHER INFORMATION: Synthetic SLP

<400> SEQUENCE: 79

Thr Ser Arg Glu Gln Phe Leu Pro Ser Glu Gly Ala Ala Cys Pro Pro
1               5                   10                  15

Trp Pro Leu Ser Val Ile Ile Thr Leu Asn Asp Glu Cys Trp Pro Ala
            20                  25                  30

Ser Leu

<210> SEQ ID NO 80
<211> LENGTH: 30
<212> TYPE: PRT
<213> ORGANISM: Artificial
<220> FEATURE:
<223> OTHER INFORMATION: Synthetic SLP

<400> SEQUENCE: 80

Arg Glu Gln Phe Leu Pro Ser Glu Gly Ala Ala Cys Pro Pro Trp Pro
1               5                   10                  15

Leu Ser Val Ile Ile Thr Leu Asn Asp Glu Cys Trp Pro Ala
            20                  25                  30

<210> SEQ ID NO 81
<211> LENGTH: 34
<212> TYPE: PRT
<213> ORGANISM: Artificial
<220> FEATURE:
<223> OTHER INFORMATION: Synthetic SLP

<400> SEQUENCE: 81

Thr Ser Arg Glu Gln Phe Leu Pro Ser Glu Gly Ala Ala Cys Pro Pro
1               5                   10                  15

Trp Gly Leu Ser Val Gly Gly Thr Leu Asn Asp Glu Cys Trp Pro Ala
            20                  25                  30

Ser Leu

<210> SEQ ID NO 82
<211> LENGTH: 30
<212> TYPE: PRT
<213> ORGANISM: Artificial
<220> FEATURE:
<223> OTHER INFORMATION: Synthetic SLP

<400> SEQUENCE: 82

Arg Glu Gln Phe Leu Pro Ser Glu Gly Ala Ala Cys Pro Pro Trp Gly
1               5                   10                  15

Leu Ser Val Gly Gly Thr Leu Asn Asp Glu Cys Trp Pro Ala
            20                  25                  30

<210> SEQ ID NO 83
<211> LENGTH: 31
<212> TYPE: PRT
<213> ORGANISM: Artificial
<220> FEATURE:
<223> OTHER INFORMATION: Synthetic SLP

<400> SEQUENCE: 83

Thr Ser Arg Glu Gln Phe Leu Pro Ser Glu Gly Ala Ala Cys Pro Pro
1               5                   10                  15

Trp Leu Ser Val Thr Leu Asn Asp Glu Cys Trp Pro Ala Ser Leu
            20                  25                  30
```

<210> SEQ ID NO 84
<211> LENGTH: 27
<212> TYPE: PRT
<213> ORGANISM: Artificial
<220> FEATURE:
<223> OTHER INFORMATION: Synthetic SLP

<400> SEQUENCE: 84

Arg Glu Gln Phe Leu Pro Ser Glu Gly Ala Ala Cys Pro Pro Trp Leu
1               5                   10                  15

Ser Val Thr Leu Asn Asp Glu Cys Trp Pro Ala
            20                  25

<210> SEQ ID NO 85
<211> LENGTH: 34
<212> TYPE: PRT
<213> ORGANISM: Artificial
<220> FEATURE:
<223> OTHER INFORMATION: Synthetic SLP

<400> SEQUENCE: 85

Thr Ser Arg Glu Gln Phe Leu Pro Ser Glu Gly Ala Ala Cys Pro Pro
1               5                   10                  15

Trp Gly Leu Ser Val Val Val Thr Leu Asn Asp Glu Cys Trp Pro Ala
            20                  25                  30

Ser Leu

<210> SEQ ID NO 86
<211> LENGTH: 30
<212> TYPE: PRT
<213> ORGANISM: Artificial
<220> FEATURE:
<223> OTHER INFORMATION: Synthetic SLP

<400> SEQUENCE: 86

Arg Glu Gln Phe Leu Pro Ser Glu Gly Ala Ala Cys Pro Pro Trp Gly
1               5                   10                  15

Leu Ser Val Val Val Thr Leu Asn Asp Glu Cys Trp Pro Ala
            20                  25                  30

<210> SEQ ID NO 87
<211> LENGTH: 34
<212> TYPE: PRT
<213> ORGANISM: Artificial
<220> FEATURE:
<223> OTHER INFORMATION: Synthetic SLP

<400> SEQUENCE: 87

Thr Ser Arg Glu Gln Phe Leu Pro Ser Glu Gly Ala Ala Cys Pro Pro
1               5                   10                  15

Trp Leu Leu Ser Val Gly Gly Thr Leu Asn Asp Glu Cys Trp Pro Ala
            20                  25                  30

Ser Leu

<210> SEQ ID NO 88
<211> LENGTH: 30
<212> TYPE: PRT
<213> ORGANISM: Artificial
<220> FEATURE:
<223> OTHER INFORMATION: Synthetic SLP

<400> SEQUENCE: 88

```
Arg Glu Gln Phe Leu Pro Ser Glu Gly Ala Ala Cys Pro Pro Trp Leu
1               5                   10                  15
Leu Ser Val Gly Ala Thr Leu Asn Asp Glu Cys Trp Pro Ala
            20                  25                  30
```

<210> SEQ ID NO 89
<211> LENGTH: 33
<212> TYPE: PRT
<213> ORGANISM: Artificial
<220> FEATURE:
<223> OTHER INFORMATION: Synthetic SLP

<400> SEQUENCE: 89

```
Thr Ser Arg Glu Gln Phe Leu Pro Ser Glu Gly Ala Ala Cys Pro Pro
1               5                   10                  15
Trp Leu Leu Ser Val Gly Thr Leu Asn Asp Glu Cys Trp Pro Ala Ser
            20                  25                  30
Leu
```

<210> SEQ ID NO 90
<211> LENGTH: 29
<212> TYPE: PRT
<213> ORGANISM: Artificial
<220> FEATURE:
<223> OTHER INFORMATION: Synthetic SLP

<400> SEQUENCE: 90

```
Arg Glu Gln Phe Leu Pro Ser Glu Gly Ala Ala Cys Pro Pro Trp Leu
1               5                   10                  15
Leu Ser Val Gly Thr Leu Asn Asp Glu Cys Trp Pro Ala
            20                  25
```

<210> SEQ ID NO 91
<211> LENGTH: 34
<212> TYPE: PRT
<213> ORGANISM: Artificial
<220> FEATURE:
<223> OTHER INFORMATION: Synthetic SLP

<400> SEQUENCE: 91

```
Tyr Arg Lys Ser Val Trp Ser Lys Leu Gln Ser Ile Gly Ile Arg Gln
1               5                   10                  15
His Ser Leu Ser Val Ala Ala Thr Leu Asn Asp Glu Cys Trp Pro Ala
            20                  25                  30
Ser Leu
```

<210> SEQ ID NO 92
<211> LENGTH: 30
<212> TYPE: PRT
<213> ORGANISM: Artificial
<220> FEATURE:
<223> OTHER INFORMATION: Synthetic SLP

<400> SEQUENCE: 92

```
Lys Ser Val Trp Ser Lys Leu Gln Ser Ile Gly Ile Arg Gln His Ser
1               5                   10                  15
Leu Ser Val Ala Ala Thr Leu Asn Asp Glu Cys Trp Pro Ala
            20                  25                  30
```

<210> SEQ ID NO 93
<211> LENGTH: 33
<212> TYPE: PRT
<213> ORGANISM: Artificial

```
<220> FEATURE:
<223> OTHER INFORMATION: Synthetic SLP

<400> SEQUENCE: 93

Thr Ser Arg Glu Gln Phe Leu Pro Ser Glu Gly Ala Ala Cys Pro Pro
1               5                   10                  15

Trp Leu Leu Ser Val Glu Leu Ala Gly Ile Gly Ile Leu Thr Val Ile
            20                  25                  30

Leu

<210> SEQ ID NO 94
<211> LENGTH: 29
<212> TYPE: PRT
<213> ORGANISM: Artificial
<220> FEATURE:
<223> OTHER INFORMATION: Synthetic SLP

<400> SEQUENCE: 94

Arg Glu Gln Phe Leu Pro Ser Glu Gly Ala Ala Cys Pro Pro Trp Leu
1               5                   10                  15

Leu Ser Val Glu Leu Ala Gly Ile Gly Ile Leu Thr Val
            20                  25

<210> SEQ ID NO 95
<211> LENGTH: 31
<212> TYPE: PRT
<213> ORGANISM: Artificial
<220> FEATURE:
<223> OTHER INFORMATION: Synthetic SLP

<400> SEQUENCE: 95

Arg Glu Gln Phe Leu Pro Ser Glu Gly Ala Ala Cys Pro Pro Trp Leu
1               5                   10                  15

Leu Ser Val Gly Gly Glu Leu Ala Gly Ile Gly Ile Leu Thr Val
            20                  25                  30

<210> SEQ ID NO 96
<211> LENGTH: 35
<212> TYPE: PRT
<213> ORGANISM: Artificial
<220> FEATURE:
<223> OTHER INFORMATION: Synthetic SLP

<400> SEQUENCE: 96

Thr Ser Arg Glu Gln Phe Leu Pro Ser Glu Gly Ala Ala Cys Pro Pro
1               5                   10                  15

Trp Leu Leu Ser Val Gly Gly Glu Leu Ala Gly Ile Gly Ile Leu Thr
            20                  25                  30

Val Ile Leu
        35

<210> SEQ ID NO 97
<211> LENGTH: 31
<212> TYPE: PRT
<213> ORGANISM: Artificial
<220> FEATURE:
<223> OTHER INFORMATION: Synthetic SLP

<400> SEQUENCE: 97

Arg Glu Gln Phe Leu Pro Ser Glu Gly Ala Ala Cys Pro Pro Trp Leu
1               5                   10                  15

Leu Ser Val Gly Ala Glu Leu Ala Gly Ile Gly Ile Leu Thr Val
            20                  25                  30
```

<210> SEQ ID NO 98
<211> LENGTH: 33
<212> TYPE: PRT
<213> ORGANISM: Artificial
<220> FEATURE:
<223> OTHER INFORMATION: Synthetic SLP

<400> SEQUENCE: 98

Thr Ser Arg Glu Gln Phe Leu Pro Ser Glu Gly Ala Ala Cys Pro Pro
1               5                   10                  15

Trp Val Leu Ser Val Gly Gly Glu Leu Ala Gly Ile Gly Ile Leu Thr
            20                  25                  30

Val

<210> SEQ ID NO 99
<211> LENGTH: 29
<212> TYPE: PRT
<213> ORGANISM: Artificial
<220> FEATURE:
<223> OTHER INFORMATION: Synthetic SLP

<400> SEQUENCE: 99

Arg Glu Gln Phe Leu Pro Ser Glu Gly Ala Ala Cys Pro Pro Trp Val
1               5                   10                  15

Leu Ser Val Gly Gly Glu Leu Ala Gly Ile Gly Ile Leu
            20                  25

<210> SEQ ID NO 100
<211> LENGTH: 32
<212> TYPE: PRT
<213> ORGANISM: Artificial
<220> FEATURE:
<223> OTHER INFORMATION: Synthetic SLP

<400> SEQUENCE: 100

Thr Ser Arg Glu Gln Phe Leu Pro Ser Glu Gly Ala Ala Cys Pro Pro
1               5                   10                  15

Trp Leu Ser Val Glu Leu Ala Gly Ile Gly Ile Leu Thr Val Ile Leu
            20                  25                  30

<210> SEQ ID NO 101
<211> LENGTH: 28
<212> TYPE: PRT
<213> ORGANISM: Artificial
<220> FEATURE:
<223> OTHER INFORMATION: Synthetic SLP

<400> SEQUENCE: 101

Arg Glu Gln Phe Leu Pro Ser Glu Gly Ala Ala Cys Pro Pro Trp Leu
1               5                   10                  15

Ser Val Glu Leu Ala Gly Ile Gly Ile Leu Thr Val
            20                  25

<210> SEQ ID NO 102
<211> LENGTH: 34
<212> TYPE: PRT
<213> ORGANISM: Artificial
<220> FEATURE:
<223> OTHER INFORMATION: Synthetic SLP

<400> SEQUENCE: 102

Thr Ser Arg Glu Gln Phe Leu Pro Ser Glu Gly Ala Ala Cys Pro Pro
1               5                   10                  15

Trp Leu Leu Ser Val Gly Glu Leu Ala Gly Ile Gly Ile Leu Thr Val
            20                  25                  30

Ile Leu

<210> SEQ ID NO 103
<211> LENGTH: 34
<212> TYPE: PRT
<213> ORGANISM: Artificial
<220> FEATURE:
<223> OTHER INFORMATION: Synthetic SLP

<400> SEQUENCE: 103

Thr Ser Arg Glu Gln Phe Leu Pro Ser Glu Gly Ala Ala Cys Pro Pro
1               5                   10                  15

Trp Val Leu Ser Val Gly Glu Leu Ala Gly Ile Gly Ile Leu Thr Val
            20                  25                  30

Ile Leu

<210> SEQ ID NO 104
<211> LENGTH: 30
<212> TYPE: PRT
<213> ORGANISM: Artificial
<220> FEATURE:
<223> OTHER INFORMATION: Synthetic SLP

<400> SEQUENCE: 104

Arg Glu Gln Phe Leu Pro Ser Glu Gly Ala Ala Cys Pro Pro Trp Val
1               5                   10                  15

Leu Ser Val Gly Glu Leu Ala Gly Ile Gly Ile Leu Thr Val
            20                  25                  30

<210> SEQ ID NO 105
<211> LENGTH: 35
<212> TYPE: PRT
<213> ORGANISM: Artificial
<220> FEATURE:
<223> OTHER INFORMATION: Synthetic SLP

<400> SEQUENCE: 105

Thr Ser Arg Glu Gln Phe Leu Pro Ser Glu Gly Ala Ala Cys Pro Pro
1               5                   10                  15

Trp Ser Leu Ser Val Ala Ala Glu Leu Ala Gly Ile Gly Ile Leu Thr
            20                  25                  30

Val Ile Leu
        35

<210> SEQ ID NO 106
<211> LENGTH: 31
<212> TYPE: PRT
<213> ORGANISM: Artificial
<220> FEATURE:
<223> OTHER INFORMATION: Synthetic SLP

<400> SEQUENCE: 106

Arg Glu Gln Phe Leu Pro Ser Glu Gly Ala Ala Cys Pro Pro Trp Ser
1               5                   10                  15

Leu Ser Val Ala Ala Glu Leu Ala Gly Ile Gly Ile Leu Thr Val
            20                  25                  30

<210> SEQ ID NO 107
<211> LENGTH: 35
<212> TYPE: PRT

<213> ORGANISM: Artificial
<220> FEATURE:
<223> OTHER INFORMATION: Synthetic SLP

<400> SEQUENCE: 107

Thr Ser Arg Glu Gln Phe Leu Pro Ser Glu Gly Ala Ala Cys Pro Pro
1               5                   10                  15

Trp Ser Leu Ser Val Gly Gly Glu Leu Ala Gly Ile Gly Ile Leu Thr
            20                  25                  30

Val Ile Leu
        35

<210> SEQ ID NO 108
<211> LENGTH: 31
<212> TYPE: PRT
<213> ORGANISM: Artificial
<220> FEATURE:
<223> OTHER INFORMATION: Synthetic SLP

<400> SEQUENCE: 108

Arg Glu Gln Phe Leu Pro Ser Glu Gly Ala Ala Cys Pro Pro Trp Ser
1               5                   10                  15

Leu Ser Val Gly Gly Glu Leu Ala Gly Ile Gly Ile Leu Thr Val
            20                  25                  30

<210> SEQ ID NO 109
<211> LENGTH: 35
<212> TYPE: PRT
<213> ORGANISM: Artificial
<220> FEATURE:
<223> OTHER INFORMATION: Synthetic SLP

<400> SEQUENCE: 109

Thr Ser Arg Glu Gln Phe Leu Pro Ser Glu Gly Ala Ala Cys Pro Pro
1               5                   10                  15

Trp Ala Leu Ser Val Gly Gly Glu Leu Ala Gly Ile Gly Ile Leu Thr
            20                  25                  30

Val Ile Leu
        35

<210> SEQ ID NO 110
<211> LENGTH: 31
<212> TYPE: PRT
<213> ORGANISM: Artificial
<220> FEATURE:
<223> OTHER INFORMATION: Synthetic SLP

<400> SEQUENCE: 110

Arg Glu Gln Phe Leu Pro Ser Glu Gly Ala Ala Cys Pro Pro Trp Ala
1               5                   10                  15

Leu Ser Val Gly Gly Glu Leu Ala Gly Ile Gly Ile Leu Thr Val
            20                  25                  30

<210> SEQ ID NO 111
<211> LENGTH: 35
<212> TYPE: PRT
<213> ORGANISM: Artificial
<220> FEATURE:
<223> OTHER INFORMATION: Synthetic SLP

<400> SEQUENCE: 111

Thr Ser Arg Glu Gln Phe Leu Pro Ser Glu Gly Ala Ala Cys Pro Pro
1               5                   10                  15

```
Trp Pro Leu Ser Val Ile Ile Glu Leu Ala Gly Ile Gly Ile Leu Thr
            20                  25                  30

Val Ile Leu
        35

<210> SEQ ID NO 112
<211> LENGTH: 31
<212> TYPE: PRT
<213> ORGANISM: Artificial
<220> FEATURE:
<223> OTHER INFORMATION: Synthetic SLP

<400> SEQUENCE: 112

Arg Glu Gln Phe Leu Pro Ser Glu Gly Ala Ala Cys Pro Pro Trp Pro
1               5                   10                  15

Leu Ser Val Ile Ile Glu Leu Ala Gly Ile Gly Ile Leu Thr Val
            20                  25                  30

<210> SEQ ID NO 113
<211> LENGTH: 35
<212> TYPE: PRT
<213> ORGANISM: Artificial
<220> FEATURE:
<223> OTHER INFORMATION: Synthetic SLP

<400> SEQUENCE: 113

Thr Ser Arg Glu Gln Phe Leu Pro Ser Glu Gly Ala Ala Cys Pro Pro
1               5                   10                  15

Trp Gly Leu Ser Val Gly Gly Glu Leu Ala Gly Ile Gly Ile Leu Thr
            20                  25                  30

Val Ile Leu
        35

<210> SEQ ID NO 114
<211> LENGTH: 31
<212> TYPE: PRT
<213> ORGANISM: Artificial
<220> FEATURE:
<223> OTHER INFORMATION: Synthetic SLP

<400> SEQUENCE: 114

Arg Glu Gln Phe Leu Pro Ser Glu Gly Ala Ala Cys Pro Pro Trp Gly
1               5                   10                  15

Leu Ser Val Gly Gly Glu Leu Ala Gly Ile Gly Ile Leu Thr Val
            20                  25                  30

<210> SEQ ID NO 115
<211> LENGTH: 35
<212> TYPE: PRT
<213> ORGANISM: Artificial
<220> FEATURE:
<223> OTHER INFORMATION: Synthetic SLP

<400> SEQUENCE: 115

Thr Ser Arg Glu Gln Phe Leu Pro Ser Glu Gly Ala Ala Cys Pro Pro
1               5                   10                  15

Trp Gly Leu Ser Val Val Val Glu Leu Ala Gly Ile Gly Ile Leu Thr
            20                  25                  30

Val Ile Leu
        35

<210> SEQ ID NO 116
<211> LENGTH: 31
```

```
<212> TYPE: PRT
<213> ORGANISM: Artificial
<220> FEATURE:
<223> OTHER INFORMATION: Synthetic SLP

<400> SEQUENCE: 116

Arg Glu Gln Phe Leu Pro Ser Glu Gly Ala Ala Cys Pro Pro Trp Gly
1               5                   10                  15

Leu Ser Val Val Val Glu Leu Ala Gly Ile Gly Ile Leu Thr Val
            20                  25                  30

<210> SEQ ID NO 117
<211> LENGTH: 35
<212> TYPE: PRT
<213> ORGANISM: Artificial
<220> FEATURE:
<223> OTHER INFORMATION: Synthetic SLP

<400> SEQUENCE: 117

Thr Ser Arg Glu Gln Phe Leu Pro Ser Glu Gly Ala Ala Cys Pro Pro
1               5                   10                  15

Trp Leu Leu Ser Val Gly Ala Glu Leu Ala Gly Ile Gly Ile Leu Thr
            20                  25                  30

Val Ile Leu
        35

<210> SEQ ID NO 118
<211> LENGTH: 30
<212> TYPE: PRT
<213> ORGANISM: Artificial
<220> FEATURE:
<223> OTHER INFORMATION: Synthetic SLP

<400> SEQUENCE: 118

Arg Glu Gln Phe Leu Pro Ser Glu Gly Ala Ala Cys Pro Pro Trp Leu
1               5                   10                  15

Leu Ser Val Gly Glu Leu Ala Gly Ile Gly Ile Leu Thr Val
            20                  25                  30

<210> SEQ ID NO 119
<211> LENGTH: 35
<212> TYPE: PRT
<213> ORGANISM: Artificial
<220> FEATURE:
<223> OTHER INFORMATION: Synthetic SLP

<400> SEQUENCE: 119

Tyr Arg Lys Ser Val Trp Ser Lys Leu Gln Ser Ile Gly Ile Arg Gln
1               5                   10                  15

His Ser Leu Ser Val Ala Ala Glu Leu Ala Gly Ile Gly Ile Leu Thr
            20                  25                  30

Val Ile Leu
        35

<210> SEQ ID NO 120
<211> LENGTH: 31
<212> TYPE: PRT
<213> ORGANISM: Artificial
<220> FEATURE:
<223> OTHER INFORMATION: Synthetic SLP

<400> SEQUENCE: 120

Lys Ser Val Trp Ser Lys Leu Gln Ser Ile Gly Ile Arg Gln His Ser
1               5                   10                  15
```

```
Leu Ser Val Ala Ala Glu Leu Ala Gly Ile Gly Ile Leu Thr Val
         20                  25                  30

<210> SEQ ID NO 121
<211> LENGTH: 15
<212> TYPE: PRT
<213> ORGANISM: Artificial
<220> FEATURE:
<223> OTHER INFORMATION: Synthetic hTERT peptide

<400> SEQUENCE: 121

Lys Ser Val Trp Ser Lys Leu Gln Ser Ile Gly Ile Arg Gln His
1               5                   10                  15

<210> SEQ ID NO 122
<211> LENGTH: 15
<212> TYPE: PRT
<213> ORGANISM: Artificial
<220> FEATURE:
<223> OTHER INFORMATION: Synthetic hTERT peptide

<400> SEQUENCE: 122

Gly Thr Ala Phe Val Gln Met Pro Ala His Gly Leu Phe Pro Trp
1               5                   10                  15

<210> SEQ ID NO 123
<211> LENGTH: 15
<212> TYPE: PRT
<213> ORGANISM: Artificial
<220> FEATURE:
<223> OTHER INFORMATION: Synthetic hTERT peptide

<400> SEQUENCE: 123

Ser Leu Cys Tyr Ser Ile Leu Lys Ala Lys Asn Ala Gly Met Ser
1               5                   10                  15

<210> SEQ ID NO 124
<211> LENGTH: 15
<212> TYPE: PRT
<213> ORGANISM: Artificial
<220> FEATURE:
<223> OTHER INFORMATION: Synthetic hTERT peptide

<400> SEQUENCE: 124

Pro Ala Ala Phe Arg Ala Leu Val Ala Gln Cys Leu Val Cys Val
1               5                   10                  15

<210> SEQ ID NO 125
<211> LENGTH: 9
<212> TYPE: PRT
<213> ORGANISM: Artificial
<220> FEATURE:
<223> OTHER INFORMATION: Synthetic hTERT peptide

<400> SEQUENCE: 125

Met Pro Arg Ala Pro Arg Cys Arg Ala
1               5

<210> SEQ ID NO 126
<211> LENGTH: 10
<212> TYPE: PRT
<213> ORGANISM: Artificial
<220> FEATURE:
<223> OTHER INFORMATION: Synthetic hTERT peptide

<400> SEQUENCE: 126
```

Ala Pro Arg Cys Arg Ala Val Arg Ser Leu
1               5                   10

<210> SEQ ID NO 127
<211> LENGTH: 10
<212> TYPE: PRT
<213> ORGANISM: Artificial
<220> FEATURE:
<223> OTHER INFORMATION: Synthetic hTERT peptide

<400> SEQUENCE: 127

Ala Pro Ser Phe Arg Gln Val Ser Cys Leu
1               5                   10

<210> SEQ ID NO 128
<211> LENGTH: 9
<212> TYPE: PRT
<213> ORGANISM: Artificial
<220> FEATURE:
<223> OTHER INFORMATION: Synthetic hTERT peptide

<400> SEQUENCE: 128

Arg Pro Ala Glu Glu Ala Thr Ser Leu
1               5

<210> SEQ ID NO 129
<211> LENGTH: 9
<212> TYPE: PRT
<213> ORGANISM: Artificial
<220> FEATURE:
<223> OTHER INFORMATION: Synthetic hTERT peptide

<400> SEQUENCE: 129

Arg Pro Ser Phe Leu Leu Ser Ser Leu
1               5

<210> SEQ ID NO 130
<211> LENGTH: 10
<212> TYPE: PRT
<213> ORGANISM: Artificial
<220> FEATURE:
<223> OTHER INFORMATION: Synthetic hTERT peptide

<400> SEQUENCE: 130

Arg Pro Ser Leu Thr Gly Ala Arg Arg Leu
1               5                   10

<210> SEQ ID NO 131
<211> LENGTH: 9
<212> TYPE: PRT
<213> ORGANISM: Artificial
<220> FEATURE:
<223> OTHER INFORMATION: Synthetic hTERT peptide

<400> SEQUENCE: 131

Asp Pro Arg Arg Leu Val Gln Leu Leu
1               5

<210> SEQ ID NO 132
<211> LENGTH: 9
<212> TYPE: PRT
<213> ORGANISM: Artificial
<220> FEATURE:
<223> OTHER INFORMATION: Synthetic hTERT peptide

<400> SEQUENCE: 132

Phe Val Arg Ala Cys Leu Arg Arg Leu

```
1               5
```

<210> SEQ ID NO 133
<211> LENGTH: 9
<212> TYPE: PRT
<213> ORGANISM: Artificial
<220> FEATURE:
<223> OTHER INFORMATION: Synthetic hTERT peptide

<400> SEQUENCE: 133

```
Ala Gly Arg Asn Met Arg Arg Lys Leu
1               5
```

<210> SEQ ID NO 134
<211> LENGTH: 9
<212> TYPE: PRT
<213> ORGANISM: Artificial
<220> FEATURE:
<223> OTHER INFORMATION: Synthetic hTERT peptide

<400> SEQUENCE: 134

```
Leu Pro Gly Thr Thr Leu Thr Ala Leu
1               5
```

<210> SEQ ID NO 135
<211> LENGTH: 9
<212> TYPE: PRT
<213> ORGANISM: Artificial
<220> FEATURE:
<223> OTHER INFORMATION: Synthetic hTERT peptide

<400> SEQUENCE: 135

```
Leu Pro Ser Pro Lys Phe Thr Ile Leu
1               5
```

<210> SEQ ID NO 136
<211> LENGTH: 10
<212> TYPE: PRT
<213> ORGANISM: Artificial
<220> FEATURE:
<223> OTHER INFORMATION: Synthetic hTERT peptide

<400> SEQUENCE: 136

```
Arg Pro Ser Leu Thr Gly Ala Arg Arg Leu
1               5                   10
```

<210> SEQ ID NO 137
<211> LENGTH: 10
<212> TYPE: PRT
<213> ORGANISM: Artificial
<220> FEATURE:
<223> OTHER INFORMATION: Synthetic hTERT peptide

<400> SEQUENCE: 137

```
Ala Pro Ser Phe Arg Gln Val Ser Cys Leu
1               5                   10
```

<210> SEQ ID NO 138
<211> LENGTH: 10
<212> TYPE: PRT
<213> ORGANISM: Artificial
<220> FEATURE:
<223> OTHER INFORMATION: Synthetic hTERT peptide

<400> SEQUENCE: 138

```
Ala Pro Arg Cys Arg Ala Val Arg Ser Leu
1               5                   10
```

```
<210> SEQ ID NO 139
<211> LENGTH: 9
<212> TYPE: PRT
<213> ORGANISM: Artificial
<220> FEATURE:
<223> OTHER INFORMATION: Synthetic hTERT peptide

<400> SEQUENCE: 139

Asp Pro Arg Arg Leu Val Gln Leu Leu
1               5

<210> SEQ ID NO 140
<211> LENGTH: 9
<212> TYPE: PRT
<213> ORGANISM: Artificial
<220> FEATURE:
<223> OTHER INFORMATION: Synthetic hTERT peptide

<400> SEQUENCE: 140

Phe Val Arg Ala Cys Leu Arg Arg Leu
1               5

<210> SEQ ID NO 141
<211> LENGTH: 9
<212> TYPE: PRT
<213> ORGANISM: Artificial
<220> FEATURE:
<223> OTHER INFORMATION: Synthetic hTERT peptide

<400> SEQUENCE: 141

Ala Gly Arg Asn Met Arg Arg Lys Leu
1               5

<210> SEQ ID NO 142
<211> LENGTH: 9
<212> TYPE: PRT
<213> ORGANISM: Artificial
<220> FEATURE:
<223> OTHER INFORMATION: Synthetic hTERT peptide

<400> SEQUENCE: 142

Leu Pro Gly Thr Thr Leu Thr Ala Leu
1               5

<210> SEQ ID NO 143
<211> LENGTH: 9
<212> TYPE: PRT
<213> ORGANISM: Artificial
<220> FEATURE:
<223> OTHER INFORMATION: Synthetic hTERT peptide

<400> SEQUENCE: 143

Leu Pro Ser Pro Lys Phe Thr Ile Leu
1               5

<210> SEQ ID NO 144
<211> LENGTH: 9
<212> TYPE: PRT
<213> ORGANISM: Artificial
<220> FEATURE:
<223> OTHER INFORMATION: Synthetic NY-ESO-1 peptide

<400> SEQUENCE: 144

Ser Leu Leu Met Trp Ile Thr Gln Cys
1               5
```

```
<210> SEQ ID NO 145
<211> LENGTH: 30
<212> TYPE: PRT
<213> ORGANISM: Artificial
<220> FEATURE:
<223> OTHER INFORMATION: Synthetic NY-ESO-1 hTERT SLP

<400> SEQUENCE: 145

Lys Ser Val Trp Ser Lys Leu Gln Ser Ile Gly Ile Arg Gln His Gly
1               5                   10                  15

Leu Ser Val Gly Gly Ser Leu Leu Met Trp Ile Thr Gln Cys
            20                  25                  30

<210> SEQ ID NO 146
<211> LENGTH: 30
<212> TYPE: PRT
<213> ORGANISM: Artificial
<220> FEATURE:
<223> OTHER INFORMATION: Synthetic NY-ESO-1 hTERT SLP

<400> SEQUENCE: 146

Lys Ser Val Trp Ser Lys Leu Gln Ser Ile Gly Ile Arg Gln His Ser
1               5                   10                  15

Leu Ser Val Ala Ala Ser Leu Leu Met Trp Ile Thr Gln Cys
            20                  25                  30

<210> SEQ ID NO 147
<211> LENGTH: 30
<212> TYPE: PRT
<213> ORGANISM: Artificial
<220> FEATURE:
<223> OTHER INFORMATION: Synthetic NY-ESO-1 hTERT SLP

<400> SEQUENCE: 147

Lys Ser Val Trp Ser Lys Leu Gln Ser Ile Gly Ile Arg Gln His Leu
1               5                   10                  15

Leu Ser Val Gly Gly Ser Leu Leu Met Trp Ile Thr Gln Cys
            20                  25                  30

<210> SEQ ID NO 148
<211> LENGTH: 9
<212> TYPE: PRT
<213> ORGANISM: Artificial
<220> FEATURE:
<223> OTHER INFORMATION: Synthetic GP100 CD8 class I peptide

<400> SEQUENCE: 148

Lys Thr Trp Gly Gln Tyr Trp Gln Val
1               5

<210> SEQ ID NO 149
<211> LENGTH: 9
<212> TYPE: PRT
<213> ORGANISM: Artificial
<220> FEATURE:
<223> OTHER INFORMATION: Synthetic GP100 CD8 class I peptide

<400> SEQUENCE: 149

Met Leu Gly Thr His Thr Met Glu Val
1               5

<210> SEQ ID NO 150
<211> LENGTH: 9
<212> TYPE: PRT
<213> ORGANISM: Artificial
```

```
<220> FEATURE:
<223> OTHER INFORMATION: Synthetic GP100 CD8 class I peptide

<400> SEQUENCE: 150

Tyr Leu Glu Pro Gly Pro Val Thr Ala
1               5

<210> SEQ ID NO 151
<211> LENGTH: 9
<212> TYPE: PRT
<213> ORGANISM: Artificial
<220> FEATURE:
<223> OTHER INFORMATION: Synthetic GP100 CD8 class I peptide

<400> SEQUENCE: 151

Ala Leu Leu Ala Val Gly Ala Thr Lys
1               5

<210> SEQ ID NO 152
<211> LENGTH: 9
<212> TYPE: PRT
<213> ORGANISM: Artificial
<220> FEATURE:
<223> OTHER INFORMATION: Synthetic GP100 CD8 class I peptide

<400> SEQUENCE: 152

Arg Ser Tyr Val Pro Leu Ala His Arg
1               5

<210> SEQ ID NO 153
<211> LENGTH: 9
<212> TYPE: PRT
<213> ORGANISM: Artificial
<220> FEATURE:
<223> OTHER INFORMATION: Synthetic GP100 CD8 class I peptide

<400> SEQUENCE: 153

Ala Leu Asn Phe Pro Gly Ser Gln Lys
1               5

<210> SEQ ID NO 154
<211> LENGTH: 10
<212> TYPE: PRT
<213> ORGANISM: Artificial
<220> FEATURE:
<223> OTHER INFORMATION: Synthetic GP100 CD8 class I peptide

<400> SEQUENCE: 154

Val Pro Leu Asp Cys Val Leu Tyr Arg Tyr
1               5                   10

<210> SEQ ID NO 155
<211> LENGTH: 13
<212> TYPE: PRT
<213> ORGANISM: Artificial
<220> FEATURE:
<223> OTHER INFORMATION: Synthetic GP100 CD8 class I peptide

<400> SEQUENCE: 155

Ser Arg Glu Gln Phe Leu Pro Ser Glu Gly Ala Ala Cys
1               5                   10

<210> SEQ ID NO 156
<211> LENGTH: 16
<212> TYPE: PRT
<213> ORGANISM: Artificial
<220> FEATURE:
```

<223> OTHER INFORMATION: Synthetic GP100 CD4 class II peptide

<400> SEQUENCE: 156

Trp Asn Arg Gln Leu Tyr Pro Glu Trp Thr Glu Ala Gln Arg Leu Asp
1               5                   10                  15

<210> SEQ ID NO 157
<211> LENGTH: 18
<212> TYPE: PRT
<213> ORGANISM: Artificial
<220> FEATURE:
<223> OTHER INFORMATION: Synthetic GP100 CD4 class II peptide

<400> SEQUENCE: 157

Thr Thr Glu Trp Val Glu Thr Thr Ala Arg Glu Leu Pro Ile Pro Glu
1               5                   10                  15

Pro Glu

<210> SEQ ID NO 158
<211> LENGTH: 15
<212> TYPE: PRT
<213> ORGANISM: Artificial
<220> FEATURE:
<223> OTHER INFORMATION: Synthetic GP100 CD4 class II peptide

<400> SEQUENCE: 158

Gly Arg Ala Met Leu Gly Thr His Thr Met Glu Val Thr Val Tyr
1               5                   10                  15

<210> SEQ ID NO 159
<211> LENGTH: 34
<212> TYPE: PRT
<213> ORGANISM: Artificial
<220> FEATURE:
<223> OTHER INFORMATION: Synthetic hTERT Meloe-1 SLP

<400> SEQUENCE: 159

Tyr Arg Lys Ser Val Trp Ser Lys Leu Gln Ser Ile Gly Ile Arg Gln
1               5                   10                  15

His Ser Leu Ser Val Ala Ala Thr Leu Asn Asp Glu Cys Trp Pro Ala
            20                  25                  30

Ser Leu

<210> SEQ ID NO 160
<211> LENGTH: 4
<212> TYPE: PRT
<213> ORGANISM: Artificial
<220> FEATURE:
<223> OTHER INFORMATION: Synthetic Linker

<400> SEQUENCE: 160

Gly Gly Gly Gly
1

<210> SEQ ID NO 161
<211> LENGTH: 4
<212> TYPE: PRT
<213> ORGANISM: Artificial
<220> FEATURE:
<223> OTHER INFORMATION: Synthetic Linker

<400> SEQUENCE: 161

Leu Val Gly Ser
1

<210> SEQ ID NO 162
<211> LENGTH: 4
<212> TYPE: PRT
<213> ORGANISM: Artificial
<220> FEATURE:
<223> OTHER INFORMATION: Synthetic Linker

<400> SEQUENCE: 162

Gly Ser Gly Ser
1

<210> SEQ ID NO 163
<211> LENGTH: 4
<212> TYPE: PRT
<213> ORGANISM: Artificial
<220> FEATURE:
<223> OTHER INFORMATION: Synthetic Linker

<400> SEQUENCE: 163

Ala Ser Leu Gly
1

<210> SEQ ID NO 164
<211> LENGTH: 5
<212> TYPE: PRT
<213> ORGANISM: Artificial
<220> FEATURE:
<223> OTHER INFORMATION: Synthetic Linker

<400> SEQUENCE: 164

Pro Ile Val Leu Gly
1               5

<210> SEQ ID NO 165
<211> LENGTH: 3
<212> TYPE: PRT
<213> ORGANISM: Artificial
<220> FEATURE:
<223> OTHER INFORMATION: Synthetic C-ter of Meloe-1 13-27

<400> SEQUENCE: 165

Pro Pro Trp
1

<210> SEQ ID NO 166
<211> LENGTH: 3
<212> TYPE: PRT
<213> ORGANISM: Artificial
<220> FEATURE:
<223> OTHER INFORMATION: Synthetic C-Ter of Meloe-1 11-23

<400> SEQUENCE: 166

Ala Ala Cys
1

<210> SEQ ID NO 167
<211> LENGTH: 3
<212> TYPE: PRT
<213> ORGANISM: Artificial
<220> FEATURE:
<223> OTHER INFORMATION: Synthetic Core linker

<400> SEQUENCE: 167

Leu Ser Val
1

-continued

```
<210> SEQ ID NO 168
<211> LENGTH: 30
<212> TYPE: PRT
<213> ORGANISM: Artificial
<220> FEATURE:
<223> OTHER INFORMATION: Synthetic hTERT Meloe-1 SLP

<400> SEQUENCE: 168

Lys Ser Val Trp Ser Lys Leu Gln Ser Ile Gly Ile Arg Gln His Ser
1               5                   10                  15

Leu Ser Val Ala Ala Thr Leu Asn Asp Glu Cys Trp Pro Ala
            20                  25                  30

<210> SEQ ID NO 169
<211> LENGTH: 4
<212> TYPE: PRT
<213> ORGANISM: Artificial
<220> FEATURE:
<223> OTHER INFORMATION: Synthetic Sequence aa

<400> SEQUENCE: 169

Thr Leu Asn Asp
1

<210> SEQ ID NO 170
<211> LENGTH: 4
<212> TYPE: PRT
<213> ORGANISM: Artificial
<220> FEATURE:
<223> OTHER INFORMATION: Synthetic sequence aa

<400> SEQUENCE: 170

Glu Leu Ala Gly
1

<210> SEQ ID NO 171
<211> LENGTH: 31
<212> TYPE: PRT
<213> ORGANISM: Artificial
<220> FEATURE:
<223> OTHER INFORMATION: Synthetic SLP control

<400> SEQUENCE: 171

Ala Ala Cys Pro Pro Trp His Pro Ser Glu Arg Ile Ser Ser Thr Leu
1               5                   10                  15

Gly Gly Gly Gly Thr Leu Asn Asp Glu Cys Trp Pro Ala Ser Leu
            20                  25                  30

<210> SEQ ID NO 172
<211> LENGTH: 32
<212> TYPE: PRT
<213> ORGANISM: Artificial
<220> FEATURE:
<223> OTHER INFORMATION: Synthetic SLP control

<400> SEQUENCE: 172

Ala Ala Thr Ser Arg Glu Gln Phe Leu Pro Ser Glu Gly Ala Ala Cys
1               5                   10                  15

Pro Pro Trp Gly Gly Gly Gly Thr Leu Asn Asp Glu Cys Trp Pro Ala
            20                  25                  30

<210> SEQ ID NO 173
<211> LENGTH: 32
<212> TYPE: PRT
<213> ORGANISM: Artificial
<220> FEATURE:
```

<223> OTHER INFORMATION: Synthetic SLP control

<400> SEQUENCE: 173

Thr Ser Arg Glu Gln Phe Leu Pro Ser Glu Gly Ala Ala Cys Pro Pro
1               5                   10                  15
Trp Gly Gly Gly Gly Thr Leu Asn Asp Glu Cys Trp Pro Ala Ser Leu
            20                  25                  30

<210> SEQ ID NO 174
<211> LENGTH: 29
<212> TYPE: PRT
<213> ORGANISM: Artificial
<220> FEATURE:
<223> OTHER INFORMATION: Synthetic SLP control

<400> SEQUENCE: 174

Arg Glu Gln Phe Leu Pro Ser Glu Gly Ala Ala Cys Pro Pro Trp Gly
1               5                   10                  15
Gly Gly Gly Glu Leu Ala Gly Ile Gly Ile Leu Thr Val
            20                  25

<210> SEQ ID NO 175
<211> LENGTH: 6
<212> TYPE: PRT
<213> ORGANISM: Artificial
<220> FEATURE:
<223> OTHER INFORMATION: Synthetic Linker

<400> SEQUENCE: 175

Pro Leu Ser Val Ile Ile
1               5

<210> SEQ ID NO 176
<211> LENGTH: 6
<212> TYPE: PRT
<213> ORGANISM: Artificial
<220> FEATURE:
<223> OTHER INFORMATION: Synthetic Linker

<400> SEQUENCE: 176

Gly Leu Ser Val Gly Gly
1               5

<210> SEQ ID NO 177
<211> LENGTH: 6
<212> TYPE: PRT
<213> ORGANISM: Artificial
<220> FEATURE:
<223> OTHER INFORMATION: Synthetic Linker

<400> SEQUENCE: 177

Gly Leu Ser Val Val Val
1               5

<210> SEQ ID NO 178
<211> LENGTH: 6
<212> TYPE: PRT
<213> ORGANISM: Artificial
<220> FEATURE:
<223> OTHER INFORMATION: Synthetic Linker

<400> SEQUENCE: 178

Ser Leu Ser Val Ala Ala
1               5

```
<210> SEQ ID NO 179
<211> LENGTH: 6
<212> TYPE: PRT
<213> ORGANISM: Artificial
<220> FEATURE:
<223> OTHER INFORMATION: Synthetic Linker

<400> SEQUENCE: 179

Ser Leu Ser Val Gly Gly
1               5

<210> SEQ ID NO 180
<211> LENGTH: 6
<212> TYPE: PRT
<213> ORGANISM: Artificial
<220> FEATURE:
<223> OTHER INFORMATION: Synthetic Linker

<400> SEQUENCE: 180

Ala Leu Ser Val Gly Gly
1               5

<210> SEQ ID NO 181
<211> LENGTH: 34
<212> TYPE: PRT
<213> ORGANISM: Artificial
<220> FEATURE:
<223> OTHER INFORMATION: Synthetic hTERT Meloe-1 SLP

<400> SEQUENCE: 181

Tyr Arg Lys Ser Val Trp Ser Lys Leu Gln Ser Ile Gly Ile Arg Gln
1               5                   10                  15

His Leu Leu Ser Val Gly Gly Thr Leu Asn Asp Glu Cys Trp Pro Ala
            20                  25                  30

Ser Leu

<210> SEQ ID NO 182
<211> LENGTH: 30
<212> TYPE: PRT
<213> ORGANISM: Artificial
<220> FEATURE:
<223> OTHER INFORMATION: Synthetic hTERT Meloe-1 SLP

<400> SEQUENCE: 182

Lys Ser Val Trp Ser Lys Leu Gln Ser Ile Gly Ile Arg Gln His Leu
1               5                   10                  15

Leu Ser Val Gly Gly Thr Leu Asn Asp Glu Cys Trp Pro Ala
            20                  25                  30

<210> SEQ ID NO 183
<211> LENGTH: 34
<212> TYPE: PRT
<213> ORGANISM: Artificial
<220> FEATURE:
<223> OTHER INFORMATION: Synthetic hTERT Meloe-1 SLP

<400> SEQUENCE: 183

Tyr Arg Lys Ser Val Trp Ser Lys Leu Gln Ser Ile Gly Ile Arg Gln
1               5                   10                  15

His Leu Leu Ser Val Gly Ala Thr Leu Asn Asp Glu Cys Trp Pro Ala
            20                  25                  30

Ser Leu

<210> SEQ ID NO 184
```

```
<211> LENGTH: 30
<212> TYPE: PRT
<213> ORGANISM: Artificial
<220> FEATURE:
<223> OTHER INFORMATION: Synthetic hTERT Meloe-1 SLP

<400> SEQUENCE: 184

Lys Ser Val Trp Ser Lys Leu Gln Ser Ile Gly Ile Arg Gln His Leu
1               5                   10                  15

Leu Ser Val Gly Ala Thr Leu Asn Asp Glu Cys Trp Pro Ala
            20                  25                  30

<210> SEQ ID NO 185
<211> LENGTH: 35
<212> TYPE: PRT
<213> ORGANISM: Artificial
<220> FEATURE:
<223> OTHER INFORMATION: Synthetic hTERT Melan-A SLP

<400> SEQUENCE: 185

Tyr Arg Lys Ser Val Trp Ser Lys Leu Gln Ser Ile Gly Ile Arg Gln
1               5                   10                  15

His Ser Leu Ser Val Ala Ala Glu Leu Ala Gly Ile Gly Ile Leu Thr
            20                  25                  30

Val Ile Leu
        35

<210> SEQ ID NO 186
<211> LENGTH: 31
<212> TYPE: PRT
<213> ORGANISM: Artificial
<220> FEATURE:
<223> OTHER INFORMATION: Synthetic hTERT Melan-A SLP

<400> SEQUENCE: 186

Lys Ser Val Trp Ser Lys Leu Gln Ser Ile Gly Ile Arg Gln His Ser
1               5                   10                  15

Leu Ser Val Ala Ala Glu Leu Ala Gly Ile Gly Ile Leu Thr Val
            20                  25                  30

<210> SEQ ID NO 187
<211> LENGTH: 35
<212> TYPE: PRT
<213> ORGANISM: Artificial
<220> FEATURE:
<223> OTHER INFORMATION: Synthetic hTERT Melan-A SLP

<400> SEQUENCE: 187

Tyr Arg Lys Ser Val Trp Ser Lys Leu Gln Ser Ile Gly Ile Arg Gln
1               5                   10                  15

His Leu Leu Ser Val Gly Gly Glu Leu Ala Gly Ile Gly Ile Leu Thr
            20                  25                  30

Val Ile Leu
        35

<210> SEQ ID NO 188
<211> LENGTH: 31
<212> TYPE: PRT
<213> ORGANISM: Artificial
<220> FEATURE:
<223> OTHER INFORMATION: Synthetic hTERT Melan-A SLP

<400> SEQUENCE: 188

Lys Ser Val Trp Ser Lys Leu Gln Ser Ile Gly Ile Arg Gln His Leu
```

```
                1               5                    10                  15
Leu Ser Val Gly Gly Glu Leu Ala Gly Ile Gly Ile Leu Thr Val
                        20                  25              30

<210> SEQ ID NO 189
<211> LENGTH: 35
<212> TYPE: PRT
<213> ORGANISM: Artificial
<220> FEATURE:
<223> OTHER INFORMATION: Synthetic hTERT Melan-A SLP

<400> SEQUENCE: 189

Tyr Arg Lys Ser Val Trp Ser Lys Leu Gln Ser Ile Gly Ile Arg Gln
1               5                   10                  15

His Leu Leu Ser Val Gly Ala Glu Leu Ala Gly Ile Gly Ile Leu Thr
                20                  25                  30

Val Ile Leu
        35

<210> SEQ ID NO 190
<211> LENGTH: 31
<212> TYPE: PRT
<213> ORGANISM: Artificial
<220> FEATURE:
<223> OTHER INFORMATION: Synthetic hTERT Melan-A SLP

<400> SEQUENCE: 190

Lys Ser Val Trp Ser Lys Leu Gln Ser Ile Gly Ile Arg Gln His Leu
1               5                   10                  15

Leu Ser Val Gly Ala Glu Leu Ala Gly Ile Gly Ile Leu Thr Val
                20                  25                  30

<210> SEQ ID NO 191
<211> LENGTH: 6
<212> TYPE: PRT
<213> ORGANISM: Artificial
<220> FEATURE:
<223> OTHER INFORMATION: Synthetic Linker

<400> SEQUENCE: 191

Leu Leu Ser Val Gly Ala
1               5
```